United States Patent
Robinson et al.

(10) Patent No.: US 11,059,883 B2
(45) Date of Patent: *Jul. 13, 2021

(54) ANTIBODY MOLECULES TO DENGUE VIRUS AND USES THEREOF

(71) Applicant: VISTERRA, INC., Waltham, MA (US)

(72) Inventors: Luke Robinson, Quincy, MA (US); Zachary Shriver, Winchester, MA (US); James R. Myette, Waltham, MA (US); Gregory Babcock, Marlborough, MA (US); Karthik Viswanathan, Acton, MA (US)

(73) Assignee: VISTERRA, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/173,678

(22) Filed: Oct. 29, 2018

(65) Prior Publication Data

US 2019/0153074 A1    May 23, 2019

Related U.S. Application Data

(62) Division of application No. 15/155,620, filed on May 16, 2016, now Pat. No. 10,155,806, which is a division of application No. 14/921,701, filed on Oct. 23, 2015, now Pat. No. 9,365,639, which is a division of application No. 14/600,306, filed on Jan. 20, 2015, now Pat. No. 9,212,217.

(60) Provisional application No. 62/046,379, filed on Sep. 5, 2014, provisional application No. 62/017,970, filed on Jun. 27, 2014, provisional application No. 61/938,646, filed on Feb. 11, 2014.

(51) Int. Cl.
| | |
|---|---|
| *C07K 16/10* | (2006.01) |
| *A61K 39/42* | (2006.01) |
| *G01N 33/569* | (2006.01) |
| *A61K 45/06* | (2006.01) |
| *A61K 39/00* | (2006.01) |

(52) U.S. Cl.
CPC .......... *C07K 16/1081* (2013.01); *A61K 39/42* (2013.01); *A61K 45/06* (2013.01); *G01N 33/56983* (2013.01); *A61K 2039/505* (2013.01); *A61K 2039/545* (2013.01); *C07K 2317/14* (2013.01); *C07K 2317/24* (2013.01); *C07K 2317/33* (2013.01); *C07K 2317/54* (2013.01); *C07K 2317/55* (2013.01); *C07K 2317/565* (2013.01); *C07K 2317/567* (2013.01); *C07K 2317/622* (2013.01); *C07K 2317/76* (2013.01); *C07K 2317/90* (2013.01); *C07K 2317/92* (2013.01); *C07K 2317/94* (2013.01); *G01N 2333/185* (2013.01); *Y02A 50/30* (2018.01)

(58) Field of Classification Search
None
See application file for complete search history.

(56) References Cited

U.S. PATENT DOCUMENTS

| | | |
|---|---|---|
| 7,473,424 B2 | 1/2009 | Burton et al. |
| 7,622,113 B2 | 11/2009 | Lai et al. |
| 7,943,134 B2 | 5/2011 | Hsieh et al. |
| 8,052,974 B2 | 11/2011 | Throsby et al. |
| 8,337,853 B2 | 12/2012 | Lai et al. |
| 8,337,854 B2 | 12/2012 | Goncalvez et al. |
| 8,460,669 B2 | 6/2013 | Hsieh et al. |
| 8,632,782 B2 | 1/2014 | Whitehead et al. |
| 8,637,035 B2 | 1/2014 | Wu et al. |
| 8,920,804 B2 | 12/2014 | Raychaudhuri et al. |
| 9,212,217 B2 | 12/2015 | Robinson et al. |
| 9,365,639 B2 | 6/2016 | Robinson et al. |
| 9,499,607 B2 | 11/2016 | Sasisekharan et al. |
| 9,880,167 B2 | 1/2018 | Sasisekharan et al. |
| 9,902,764 B2 | 2/2018 | Sasisekharan et al. |
| 10,155,806 B2 | 12/2018 | Robinson et al. |
| 10,519,220 B2 | 12/2019 | Sasisekharan et al. |
| 2004/0209244 A1 | 10/2004 | Burton et al. |
| 2005/0147614 A1 | 7/2005 | Begent et al. |
| 2009/0312190 A1 | 12/2009 | Chinea Santiago et al. |
| 2010/0150912 A1 | 6/2010 | Rappuoli |
| 2010/0239567 A1 | 9/2010 | Esue |
| 2011/0008256 A1 | 1/2011 | Lai et al. |
| 2011/0059079 A1 | 3/2011 | Babuka et al. |
| 2011/0212105 A1 | 9/2011 | Huerta Galindo et al. |
| 2012/0020957 A1 | 1/2012 | Lanzavecchia |
| 2013/0089543 A1 | 4/2013 | Lai et al. |
| 2013/0164734 A1 | 6/2013 | Raychaudhuri et al. |
| 2013/0259871 A1 | 10/2013 | Macary et al. |
| 2013/0344058 A1 | 12/2013 | Goncalvez et al. |
| 2014/0056913 A1 | 2/2014 | Sasisekharan et al. |

(Continued)

FOREIGN PATENT DOCUMENTS

| | | |
|---|---|---|
| CN | 104768574 A | 7/2015 |
| EP | 2651975 B1 | 10/2013 |

(Continued)

OTHER PUBLICATIONS

Chi, "Excipients and their Effects on the Quality of Biologics," (2012) downloaded from www2.aaps.org/uploadedFiles/Content/Sections_and_Groups/Sections/Formulation_Design_and_Development_Section/FDDTechCornerMay2012.pdf, 9 pages.

Daugherty et al., "Formulation and Delivery Issues for Monoclonal Antibody Therapeutics," in Current Trends in Monoclonal Antibody Development and Manufacturing, ed. Shire et al. (2010) Chapter 8, pp. 103-129, Springer, United States.

Goswani et al., "Developments and Challenges for mAb-based Therapeutics," Antibodies (2013) Vo. 2, pp. 452-500.

(Continued)

*Primary Examiner* — Stacy B Chen

(74) *Attorney, Agent, or Firm* — Lando & Anastasi, LLP

(57) ABSTRACT

Antibody molecules that specifically bind to dengue virus are disclosed. In certain embodiments, the antibody molecule bind to dengue virus serotypes DV-1, DV-2, DV-3, and DV-4. The antibody molecules can be used to treat, prevent, and/or diagnose dengue virus.

30 Claims, 33 Drawing Sheets

Specification includes a Sequence Listing.

(56) References Cited

U.S. PATENT DOCUMENTS

| | | |
|---|---|---|
| 2014/0349321 A1 | 11/2014 | Fink et al. |
| 2015/0086978 A1 | 3/2015 | Raychaudhuri et al. |
| 2015/0225474 A1 | 8/2015 | Robinson et al. |
| 2015/0368321 A1 | 12/2015 | Sasisekharan et al. |
| 2016/0046697 A1 | 2/2016 | Robinson et al. |
| 2016/0251413 A1 | 9/2016 | Robinson et al. |
| 2017/0089898 A1 | 3/2017 | Sasisekharan et al. |
| 2017/0274076 A1 | 9/2017 | Hay et al. |
| 2018/0237504 A1 | 8/2018 | Sasisekharan et al. |
| 2018/0246101 A1 | 8/2018 | Sasisekharan et al. |
| 2019/0153074 A1 | 5/2019 | Robinson et al. |
| 2020/0207841 A1 | 7/2020 | Sasisekharan et al. |
| 2020/0237913 A1 | 7/2020 | Hay et al. |
| 2020/0264176 A1 | 8/2020 | Sasisekharan et al. |

FOREIGN PATENT DOCUMENTS

| | | |
|---|---|---|
| WO | 2004067567 A3 | 8/2004 |
| WO | 2005056600 A2 | 6/2005 |
| WO | 2006120230 A2 | 11/2006 |
| WO | 2007059715 A2 | 5/2007 |
| WO | 2008125985 A2 | 10/2008 |
| WO | 2009120225 A1 | 10/2009 |
| WO | 2010043977 A2 | 4/2010 |
| WO | 2010093335 A1 | 8/2010 |
| WO | 2012082073 A1 | 6/2012 |
| WO | 2013035345 A2 | 3/2013 |
| WO | 2013089647 A1 | 6/2013 |
| WO | 2013151764 A1 | 10/2013 |
| WO | 2013173348 A1 | 11/2013 |
| WO | 2014025546 A2 | 2/2014 |
| WO | 2014110092 A1 | 7/2014 |
| WO | 2015122995 A1 | 8/2015 |
| WO | 2015123362 A1 | 8/2015 |
| WO | 2017165736 A1 | 9/2017 |

OTHER PUBLICATIONS

International Search Report and Written Opinion issued in PCT/US2017/023973, dated Jun. 14, 2017.

Ohtake et al., "Interactions of formulation excipients with proteins in solution and in the dried state," Advanced Drug Delivery Reviews (2011) vol. 63, pp. 1053-1073.

Razinkov et al., "Accelerated Formulation Development of Monoclonal Antibodies (mAbs) and mAb-Based Modalities: Review of Methods and Tools," Journal of Biomolecular Screening (2015) vol. 20, No. 4, pp. 468-483.

Wang et al., "Antibody Structure, Instability, and Formulation," Journal of Pharmaceutical Sciences (2007) vol. 96, pp. 1-26.

Warne, "Development of high concentration protein biopharmaceuticals: The use of platform approaches in formulation development," European Journal of Pharmaceutics and Biopharmaceutics (2011) vol. 78, No. 2, pp. 208-212.

Balsitis, S.J. et al., "Lethal Antibody Enhancement of Dengue Disease in Mice is Prevented by Fc Modification", PLOS Pathogens, vol. 6, Issue 2, e1000790, Feb. 2010.

Bedouelle et al., "Diversity and Junction Residues as Hotspots of Binding Energy in an Antibody Neutralizing the Dengue Virus", The FEBS Journal, 273 (2006) 34-46.

Beltramello et al., "The Human Immune Response to Dengue Virus Is Dominated by Highly Cross-Reactive Antibodies Endowed with Neutralizing and Enhancing Activity", Cell Host Microbe, 8(3), pp. 271-283, Sep. 16, 2010.

Brien, J.D. et al., "Protection by Immunoglobulin Dual-Affinity Retargeting Antibodies against Dengue Virus", Journal of Virology, vol. 87, No. 13, pp. 7747-7753, May 8, 2013.

Budigi et al., "Neutralization of antibody-enhanced dengue infection by VIS513, a pan serotype reactive monoclonal antibody targeting domain III of the dengue E protein," PLoS Negl Trop Dis (2018) vol. 12, No. 2, Article e0006209.

Chambers et al., "Yellow Fever Virus/Dengue-2 Virus and Yellow Fever Virus/Dengue-4 Virus Chimeras: Biological Characterization, Immunogenicity, and Protection Against Dengue Encephalitis in the Mouse Model", Journal of Virology, Mar. 2003, 77(6):3655-68.

Cockburn et al., "Mechanism of Dengue Virus Broad Cross-Neutralization by a Monoclonal Antibody", Structure 20, 303-314, Feb. 8, 2012.

De Alwis, R. et al., "Identification of Human Neutralizing Antibodies that Bind to Complex Epitopes on Dengue Virions", PNAS, May 2012, 109(19):7439-7444.

Falconar, A.K., Identification of an Epitope on the Dengue Virus Membrane (M) Protein Defined by Cross-Protective Monoclonal Antibodies: Design of an Improved Epitope Sequence Based on Common Determinants Present in Both Envelope (E and M) Proteins, Archives Virology, vol. 144, No. 12, pp. 2313-2330 (1999).

GenBank entry AJ131288.1, "Mus musculus mRNA for Dengue virus type 1 specific immunoglobulin gamma heavy chain, partial" dated Jun. 12, 1999.

GenBank entry AJ131289.1, "Mus musculus mRNA for Dengue virus type 1 specific immunoglobulin gamma kappa chain, partial" dated Jun. 12, 1999.

Goncalvez et al., "Monoclonal Antibody-Mediated Enhancement of Dengue Virus Infection in Vitro and In Vivo and Strategies for Prevention", Proc Natl Acad Sci, May 29, 2007, 104(22):9422-7.

Hang, V.T.T. et al., "Emergence of the Asian 1 Genotype of Dengue Virus Serotype 2 in Viet Nam: In Vivo Fitness Advantage and Lineage Replacement in South-East Asia", PLOS Neglected Tropical Diseases, vol. 4, Issue 7, e757, Jul. 2010.

Hezareh et al., "Effector Function Activities of a Panel of Mutants of a Broadly Neutralizing Antibody Against Human Immunodeficiency Virus Type 1", Journal of Virology, vol. 75, No. 24, Dec. 1, 2001, pp. 12161-12168.

International Search Report and Written Opinion from PCT Application No. PCT/US2015/011965 dated May 4, 2015.

Ong et al., Preclinical evaluation of VIS513, a therapeutic antibody against dengue virus, in non-human primates, Antiviral Research (2017) vol. 144, pp. 44-47.

Presentation by Robert J. Hill, entitled "Pharmaceutical Composition Claims and Enablement," downloaded from the USPTO website on Aug. 19, 2015.

Puttikhunt et al., "Novel Anti-Dengue Monoclonal Antibody Recognizing Conformational Structure of the prM-E Heterodimeric Complex of Dengue Virus", Journal of Medical Virology, 80:125-33 (2008).

Rajamanonmani, R. et al., "On a Mouse Monoclonal Antibody that Neutralizes all Four Dengue Virus Serotypes", Journal of General Virology, vol. 90, pp. 799-809 (2009).

Robinson, Luke N. et al., "Structure-Guided Design of an Anti-Dengue Antibody Directed to a Non-Immunodominant Epitope", Cell, 162, 1-12, Jul. 30, 2015.

Search Report and Written Opinion issued in Singapore Application No. 11201606624W, completed Sep. 28, 2017.

Supplementary Information for Tharakaraman, K. et al., "Redesign of a cross-reactive antibody to dengue virus with broad-spectrum activity and increased in vivo potency", Proceedings of the National Academy of Sciences, vol. 110, No. 17, pp. E1555-E1564, Apr. 8, 2013.

Tharakaraman, K. et al., "Redesign of a cross-reactive antibody to dengue virus with broad-spectrum activity and increased in vivo potency", Proceedings of the National Academy of Sciences, vol. 110, No. 17, pp. E1555-E1564, Apr. 8, 2013.

Thullier et al., "Mapping of a Dengue Virus Neutralizing Epitope Critical for the Infectivity of All Serotypes: Insight into the Neutralization Mechanism", Journal of General Virology, vol. 82, pp. 1885-1892 (2001).

Wan et al., "Current Progress in Dengue Vaccines", Journal of Biomedical Science, 2013, 20:37, 9 pages.

[No Author Listed] Press Release—"Visterra to Present Data at ICAAC on VIS513, its Humanized Monoclonal Antibody That Targets a Conserved Site on the Dengue Virus E Protein," Sep. 3, 2014, 2 pages.

Amin et al., "Protein aggregation, particle formation, characterization & rheology," Curr Op Coll & Interface Sci (2014) vol. 19, Issue 5, pp. 438-449.

(56) References Cited

OTHER PUBLICATIONS

Evans, "Removing Aggregates in Monoclonal Antibody Purification," Pharmaceutical Technology (2015) Vol. 39, Issue 3, pp. 72-74.

D88

<u>VH amino acid and nucleotide sequence</u>
QVQLVQSGAEVKKPGASVKVSCKA^GFNIK<u>DVYMS</u>WVRQAPEQGLEWMG<u>RIDPENGDTKYDPKLQ</u>GRVT
MTADTSTNTAYMELRSLRSDDTAVYYCAR<u>GWEGFAY</u>WGQGTLVTVSS (SEQ ID NO: 1)

CAAGTGCAACTCGTTCAGTCCGGAGCAGAAGTCAAGAAACCTGGAGCTTCAGTCAAAGTCAGCTGCAAG
GCCGGCTTCAATATCAAGGACGTCTACATGTCCTGGGTGCGGCAGGCTCCAGAGCAAGGACTGGAATGG
ATGGGGCGCATTGACCCGGAGAACGGTGATACGAAGTACGACCCGAAACTGCAGGGCCGCGTGACCATG
ACCGCAGATACTAGCACCAACACCGCGTACATGGAGCTGCGGTCCTTGAGGTCGGATGACACTGCTGTG
TATTACTGTGCCAGAGGCTGGGAAGGGTTCGCGTACTGGGGACAGGGAACTCTCGTGACTGTGTCGTCT
(SEQ ID NO: 37)

<u>^ denotes deletion of position S26</u>

<u>VL amino acid and nucleotide sequence</u>
DIVMTQSPASLAVSLGERATISC<u>RASENVDKYGNSFMH</u>WYQQKPGQPPKLLIY<u>RASELQW</u>GVPDRFSGS
GSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

F38

<u>VH amino acid and nucleotide sequence</u>
QVQLVQSGAEVKKPGASVKVSCKA^GFNIK<u>DVYMS</u>WVRQAPGQGLEWMG<u>RIDPENGDTKYDPKLQ</u>GRV
TMTADTSTNTAYMELRSLRSDDTAVYYCAR<u>GWEGFAY</u>WGQGTLVTVSS (SEQ ID NO: 80)

CAAGTGCAACTCGTTCAGTCCGGAGCAGAAGTCAAGAAACCTGGAGCTTCAGTCAAAGTCAGCTGCAAG
GCCGGCTTCAATATCAAGGACGTCTACATGTCCTGGGTGCGGCAGGCTCCAGGGCAAGGACTGGAATGG
ATGGGGCGCATTGACCCGGAGAACGGTGATACGAAGTACGACCCGAAACTGCAGGGCCGCGTGACCATG
ACCGCAGATACTAGCACCAACACCGCGTACATGGAGCTGCGGTCCTTGAGGTCGGATGACACTGCTGTG
TATTACTGTGCCAGAGGCTGGGAAGGGTTCGCGTACTGGGGACAGGGAACTCTCGTGACTGTGTCGTCT
(SEQ ID NO: 82)

<u>^ denotes deletion of position S26</u>

<u>VL amino acid and nucleotide sequence</u>
DIVMTQSPASLAVSLGERATISC<u>RASENVDKYGNSFMH</u>WYQQKPGQPPKLLIY<u>RASELQW</u>GVPDRFSG
SGSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASGFNIK<u>DTYMS</u>WVRQAPEQGLEWMG<u>RIDPENGDTKYDPKLQ</u>GRVT
MTADTSTNTAYMELRSLRSDDTAVYYCAR<u>GWEGFAY</u>WGQGTLVTVSS (SEQ ID NO: 16)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACACCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 39)

VL amino acid and nucleotide sequence
DIVMTQSPASLAVSLGERATISC<u>RASENVDKYGNSFMH</u>WYQQKPGQPPKLLIY<u>RASELQW</u>GVPDRFSGS
GSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

C88

VH amino acid and nucleotide sequence
QVQLVQSGAEVKKPGASVKVSCKASGFNIK<u>DVYMS</u>WVRQAPEQGLEWMG<u>RIDPENGDTKYDPKLQ</u>GRVT
MTADTSTNTAYMELRSLRSDDTAVYYCAR<u>GWEGFAY</u>WGQGTLVTVSS (SEQ ID NO: 17)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 40)

VL amino acid and nucleotide sequence
DIVMTQSPASLAVSLGERATISC<u>RASENVDKYGNSFMH</u>WYQQKPGQPPKLLIY<u>RASELQW</u>GVPDRFSGS
GSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASGFNIKDVYMSWVRQAPGQGLEWMGRIDPENGDTKYDPKLQGRVT
MTADTSTNTAYMELRSLRSDDTAVYYCARGWEGFAYWGQGTLVTVSS (SEQ ID NO: 81)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACGTCTACATGTCCTGGGTGCGGCAGGCTCCAGGGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 83)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

B48

VH amino acid and nucleotide sequence
QVQLVQSGAEVKKPGASVKVSCKA^GFNIKDTYMSWVRQAPEQGLEWMGRIDPENGDTKYDPKLQGRVT
MTADTSTNTAYMELRSLRSDDTAVYYCARGWEGFAYWGQGTLVTVSS (SEQ ID NO: 18)

CAAGTGCAACTCGTTCAGTCCGGAGCAGAAGTCAAGAAACCTGGAGCTTCAGTCAAAGTCAGCTGCAAG
GCCGGCTTCAATATCAAGGACACCTACATGTCCTGGGTGCGGCAGGCTCCAGAGCAAGGACTGGAATGG
ATGGGGCGCATTGACCCGGAGAACGGTGATACGAAGTACGACCCGAAACTGCAGGGCCGCGTGACCATG
ACCGCAGATACTAGCACCAACACCGCGTACATGGAGCTGCGGTCCTTGAGGTCGGATGACACTGCTGTG
TATTACTGTGCCAGAGGCTGGGAAGGGTTCGCGTACTGGGGACAGGGAACTCTCGTGACTGTGTCGTCT
(SEQ ID NO: 41)
^ denotes deletion of position S26

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASGFNIKDTYMSWVRQAPEQGLEWMGRIDPENGDTKYDPKLQGRVT
MTADTSTNTAYMELRSLRSDDTAVYYCVRGWEGFAYWGQGTLVTVSS (SEQ ID NO: 19)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACACCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGTCAGAGGCTGGGAAGGGTTCGCGTACTGGGGACAGGGAACTCTCGTGACTGTGTCG
TCT (SEQ ID NO: 42)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

A100

VH amino acid and nucleotide sequence
QVQLVQSGAEVKKPGASVKVSCKASGFNIKDTYMSWVRQAPEQGLEWMGRIDPENGDTKYDPKLQGRVT
MTADTSTNTAYMELRSLRSDDTAVYYCSRGWEGFAYWGQGTLVTVSS (SEQ ID NO: 20)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACACCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTTCCAGAGGCTGGGAAGGGTTCGCGTACTGGGGACAGGGAACTCTCGTGACTGTGTCG
TCT (SEQ ID NO: 86)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKAS<u>YW</u>NIK<u>DTYMS</u>WVRQAPEQGLEWMG<u>RIDPENGDTKYDPKLDG</u>RVT
MTADTSTNTAYMELRSLRSDDTAVYYCAR<u>GWEGFAY</u>WGQGTLVTVSS (SEQ ID NO: 21)

CAAGTGCAACTCGTTCAGTCCGGAGCAGAAGTCAAGAAACCTGGAGCTTCAGTCAAAGTCAGCTGCAAG
GCCTCGTACTGGAATATCAAGGACACCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 43)

VL amino acid and nucleotide sequence
DIVMTQSPASLAVSLGERATISC<u>RASENVDKYGNSFMH</u>WYQQKPGQPPKLLIY<u>RASELQW</u>GVPDRFSGS
GSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

C78

VH amino acid and nucleotide sequence
QVQLVQSGAEVKKPGASVKVSCKASGFNI<u>QDVYMS</u>WVRQAPEQGLEWMG<u>RIDPENGDTKYDPKLDG</u>RVT
MTADTSTNTAYMELRSLRSDDTAVYYCAR<u>GWEGFAY</u>WGQGTLVTVSS (SEQ ID NO: 23)

CAAGTGCAACTCGTTCAGTCCGGAGCAGAAGTCAAGAAACCTGGAGCTTCAGTCAAAGTCAGCTGCAAG
GCCTCGGGCTTCAATATCCAGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 44)

VL amino acid and nucleotide sequence
DIVMTQSPASLAVSLGERATISC<u>RASENVDKYGNSFMH</u>WYQQKPGQPPKLLIY<u>RASELQW</u>GVPDRFSGS
GSGTDFTLTISSLQAEDVAVYYC<u>QRSNEVPWT</u>FGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASGFNISDVYMSWVRQAPEQGLEWMGRIDPENGDTKYDPKLQGRVT
MTADTSTNTAYMELRSLRSDDTAVYYCARGWEGFAYWGQGTLVTVSS (SEQ ID NO: 25)

CAAGTGCAACTCGTTCAGTCCGGAGCAGAAGTCAAGAAACCTGGAGCTTCAGTCAAAGTCAGCTGCAAG
GCCTCGGGCTTCAATATCTCGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 45)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

D98

VH amino acid and nucleotide sequence
QVQLVQSGAEVKKPGASVKVSCKASAFNIKDTYMSWVRQAPEQGLEWMGRIDPENGDTKYDPKLQGRVT
MTADTSTNTAYMELRSLRSDDTAVYYCARGWEGFAYWGQGTLVTVSS (SEQ ID NO: 27)

CAAGTGCAACTCGTTCAGTCCGGAGCAGAAGTCAAGAAACCTGGAGCTTCAGTCAAAGTCAGCTGCAAG
GCCTCGGCCTTCAATATCAAGGACACCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 46)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASAFNIKDVYMSWVRQAPEQGLEWMGRIDPENGDTKYDPKLQGRVT
MTADTSTNTAYMELRSLRSDDTAVYYCARGWEGFAYWGQGTLVTVSS (SEQ ID NO: 29)

CAAGTGCAACTCGTTCAGTCCGGAGCAGAAGTCAAGAAACCTGGAGCTTCAGTCAAAGTCAGCTGCAAG
GCCTCGGCCTTCAATATCAAGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 87)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

C128

VH amino acid and nucleotide sequence
QVQLVQSGAEVKKPGASVKVSCKASGFNIKDVYMSWVRQAPEQGLEWMGRIDPENGDTKYDPKLQGRVT
MTADTSTNTAYMELRSLRSDDTAVYYCSRGWEGFAYWGQGTLVTVSS (SEQ ID NO: 31)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTAGCAGAGGCTGGGAAGGGTTCGCGTACTGGGGACAGGGAACTCTCGTGACTGTGTCG
TCT (SEQ ID NO: 88)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

VH amino acid and nucleotide sequence
QVQLVQSGAEVKKPGASVKVSCKASGFNIKDVYMSWVRQAPEQGLEWMGRIDPENGDTKYDPKLQGRVT
MTADTSTNTAYMELRSLRSDDTAVYYCVRGWEGFAYWGQGTLVTVSS (SEQ ID NO: 32)

CAAGTGCAACTCGTTCAGTCCGGAGCAGAAGTCAAGAAACCTGGAGCTTCAGTCAAAGTCAGCTGCAAG
GCCTCGGGCTTCAATATCAAGGACGTCTACATGTCCTGGGTGCGGCAGGCTCCAGAGCAAGGACTGGAA
TGGATGGGGCGCATTGACCCGGAGAACGGTGATACGAAGTACGACCCGAAACTGCAGGGCCGCGTGACC
ATGACCGCAGATACTAGCACCAACACCGCGTACATGGAGCTGCGGTCCTTGAGGTCGGATGACACTGCT
GTGTATTACTGTGCCAGAGGCTGGGAAGGGTTCGCGTACTGGGGACAGGGAACTCTCGTGACTGTGTCG
TCT (SEQ ID NO: 89)

VL amino acid and nucleotide sequence
DIVMTQSPASLAVSLGERATISCRASENVDKYGNSFMHWYQQKPGQPPKLLIYRASELQWGVPDRFSGS
GSGTDFTLTISSLQAEDVAVYYCQRSNEVPWTFGQGTKLEIK (SEQ ID NO: 2)

GATATTGTCATGACCCAAAGCCCAGCCTCCCTCGCCGTGTCTCTCGGAGAAAGAGCAACTATCTCGTGC
CGGGCTTCGGAGAATGTGGACAAGTACGGCAACTCCTTCATGCACTGGTACCAGCAGAAACCGGGACAG
CCGCCTAAACTGTTGATCTACCGGGCGTCAGAACTGCAATGGGGAGTGCCTGACAGGTTTTCGGGTTCG
GGATCCGGCACGGATTTCACCCTCACTATCTCCAGCCTGCAAGCAGAGGACGTTGCGGTGTACTACTGT
CAGCGCTCAAACGAGGTCCCATGGACTTTTGGACAAGGGACCAAGCTGGAAATCAAG (SEQ ID NO: 38)

A11 (mouse antibody)

VH amino acid and nucleotide sequence
QVKLLEQSGAELVKPGASVRLSCTASGFNIKDTYMSWVKQRPEQGLEWIGRIDPENGDTKYDPKFQGKA
TITADTSSNTAYLHLSSLTSGDTAVYYCSRGWEGFAYWGQGTLVTVSA (SEQ ID NO: 33)

CAAGTCAAACTGCTGGAACAGTCCGGAGCAGAGCTGGTGAAGCCTGGAGCGTCGGTGCGGCTTTCGTGT
ACCGCCTCCGGCTTTAACATCAAGGACACCTACATGTCGTGGGTGAAGCAGAGGCCCGAGCAGGGGCTC
GAATGGATTGGCCGCATCGACCCGGAAAATGGTGATACCAAATACGACCCAAAGTTCCAGGGAAAGGCC
ACTATCACTGCAGATACTTCAAGCAACACCGCCTACCTCCACCTGTCCTCGCTCACTTCCGGAGATACC
GCGGTCTACTATTGCTCAAGAGGATGGGAAGGCTTCGCGTACTGGGGTCAAGGAACGTTGGTGACCGTC
AGCGCC (SEQ ID NO: 47)

VL amino acid and nucleotide sequence
ELVMTQTPASLAVSLGQRATISCRASENVDKYGNSFMHWYQQKAGQPPKLLIYRASELQWGIPARFSGS
GSRTDFTLTINPVEADDVATYFCQRSNEVPWTFGGGTKLEIK (SEQ ID NO: 34)

GAATTGGTCATGACTCAGACGCCAGCTTCGCTGGCCGTGTCACTGGGACAGAGGGCCACTATCAGCTGC
AGAGCATCGGAGAATGTGGATAAGTACGGGAACAGCTTCATGCACTGGTATCAACAGAAAGCTGGTCAA
CCTCCGAAGCTGCTTATCTACCGGGCGTCGGAACTCCAATGGGGCATTCCAGCACGGTTCAGCGGGTCG
GGCTCCAGAACTGACTTCACCCTCACCATCAATCCCGTGGAGGCCGATGACGTGGCGACCTACTTTTGT
CAGCGCTCCAACGAGGTCCCGTGGACTTTCGGAGGAGGAACCAAGCTGGAAATCAAG (SEQ ID NO: 48)

Fig. 1H

B11 (mouse antibody)

VH amino acid and nucleotide sequence

QVKLLEQSGAELVKPGASVRLSCTA^GFNIK<u>DTYMS</u>WVKQRPEQGLEWIG<u>RIDPENGDTKYDPKFQG</u>KA
TITADTSSNTAYLHLSSLTSGDTAVYYCSR<u>GWEGFAY</u>WGQGTLVTVSA (SEQ ID NO: 36)

CAAGTCAAACTGCTGGAACAGTCCGGAGCAGAGCTGGTGAAGCCTGGAGCGTCGGTGCGGCTTTCGTGT
ACCGCCGGCTTTAACATCAAGGACACCTACATGTCGTGGGTGAAGCAGAGGCCCGAGCAGGGGCTCGAA
TGGATTGGCCGCATCGACCCGGAAAATGGTGATACCAAATACGACCCAAAGTTCCAGGGAAAGGCCACT
ATCACTGCAGATACTTCAAGCAACACCGCCTACCTCCACCTGTCCTCGCTCACTTCCGGAGATACCGCG
GTCTACTATTGCTCAAGAGGATGGGAAGGCTTCGCGTACTGGGGTCAAGGAACGTTGGTGACCGTCAGC
GCC (SEQ ID NO: 49)

^ denotes deletion of position S26

VL amino acid and nucleotide sequence

ELVMTQTPASLAVSLGQRATISC<u>RASENVDKYGNSFMH</u>WYQQKAGQPPKLLIY<u>RASELQW</u>GIPARFSGS
GSRTDFTLTINPVEADDVATYFC<u>QRSNEVPWT</u>FGGGTKLEIK (SEQ ID NO: 34)

GAATTGGTCATGACTCAGACGCCAGCTTCGCTGGCCGTGTCACTGGGACAGAGGGCCACTATCAGCTGC
AGAGCATCGGAGAATGTGGATAAGTACGGGAACAGCTTCATGCACTGGTATCAACAGAAAGCTGGTCAA
CCTCCGAAGCTGCTTATCTACCGGGCGTCGGAACTCCAATGGGGCATTCCAGCACGGTTCAGCGGGTCG
GGCTCCAGAACTGACTTCACCCTCACCATCAATCCCGTGGAGGCCGATGACGTGGCGACCTACTTTTGT
CAGCGCTCCAACGAGGTCCCGTGGACTTTCGGAGGAGGAACCAAGCTGGAAATCAAG (SEQ ID NO: 48)

Fig. 1I

| Antibody | Framework | EDIII-DV1 Kd (nM) | EDIII-DV2 Kd (nM) | EDIII-DV3 Kd (nM) | EDIII-DV4 Kd (nM) |
|---|---|---|---|---|---|
| A11 | Mouse | 0.269 | <0.1 | 18.03 | 89.71 |
| B11 | Mouse | <0.1 | <0.1 | 2.98 | 7.42 |
| A68 (A48 + A98V) | Human | <0.1 | <0.1 | 3 | 13.06 |
| A48 | Human | <0.1 | <0.1 | 5.8 | 52.20 |
| B48 + A98V | Human | <0.1 | <0.1 | 5.06 | 9.26 |
| B47 | Human | <0.1 | <0.1 | 7.29 | 20.15 |
| B48 (A48+del26) | Human | 0.123 | <0.1 | 8 | 27.61 |
| B28 – | Human | 0.134 | <0.1 | 9.29 | 37.77 |

Fig. 4

|  | Heavy Chain | | | Light Chain | |
|---|---|---|---|---|---|
| mAb | FW | N-terminus changes | CDR mutations relative to A11 | Light Chain FW | EDIII-DV4 Kd (nM) |
| C88 (A48+T33V) | human (04) | -- | T33V | human (08) | 13 |
| C41 | Mouse | -- | T33V | Mouse | 2.56 |
| A48+V2L | human (04) | QLQLVQSG (SEQ ID NO: 95) (V2L) | T33V | human (08) | 21.34 |
| A48+InsE6 | human (04) | QVQLVEQSG (SEQ ID NO: 96) (E insertion) | T33V | human (08) | 19.51 |
| D38 | human (04) | QVKLVEQSG (SEQ ID NO: 97) (Q3K + E insertion) | T33V | human (08) | 12.88 |
| D48 | human (04) | QVKLLEQSG (SEQ ID NO: 98) (Q3K +V5L + E insertion) | T33V | human (08) | 7.494 |

|  | Heavy Chain | | | Light Chain | |
|---|---|---|---|---|---|
| mAb | FW | N-terminus changes | FW1 mutations relative to A11 | Light Chain FW | EDIII-DV4 Kd (nM) |
| B48 | human (04) | -- | del26 | human (08) | 19.33 |
| B48+V2L | human (04) | QLQLVQSG (SEQ ID NO: 95) (V2L) | del26 | human (08) | 23.65 |
| B48+InsE6 | human (04) | QVQLVEQSG (SEQ ID NO: 96) (E insertion) | del26 | human (08) | 26.89 |

Fig. 5

| mAb name | Heavy Chain CDR muts relative to A48 | Light Chain Light Chain FW | EDIII-DV4 Kd (nM) |
|---|---|---|---|
| C88 | T33V | human (08) | 13 |
| D88 | Del26, T33V | human (08) | 3.115 |
| D98 | G27A, T33V | human (08) | 16.91 |
| D108 | G27Y, F28W, T33V | human (08) | 18.33 |
| D118 | F28W, T33V | human (08) | 12.61 |
| D128 | G27A, F28W, T33V | human (08) | 20.77 |
| D138 | G27Y, F28A, T33V | human (08) | 4156 |
| D148 | G27Y, T33V | human (08) | 17.99 |
| D158 | G27Y, F28G, T33V | human (08) | 1205 |
| D168 | F28Y, T33V | human (08) | 323.8 |

Fig. 6

| Ab name | Mutation relative to A48 | EDIII-DV3 Kd (nM) | EDIII-DV4 Kd (nM) |
|---|---|---|---|
| C88 | T33V | 0.97 | 23.78 |
| C98 | T33V, A98V | 1.21 | 10.51 |
| C128 | T33V, A98S | 0.63 | 18.7 |
| D88 | Del26+T33V | 1.05 | 5.01 |
| D178 | Del26+T33V+A98V | 1.05 | 4.67 |
| D188 | Del26+T33V+A98S | 1.06 | 5.92 |

Fig. 7

| MAb | EDIII-DV1 Kd (nM) | EDIII-DV2 Kd (nM) | EDIII-DV3 Kd (nM) | EDIII-DV4 Kd (nM) | EDIII-DV4 [1/7] Kd (nM) |
|---|---|---|---|---|---|
| C88 (A48+T33V) | <0.1 | <0.1 | 1.06 | 15.37 | 13.00 |
| D88 (A48+T33V+del26) | <0.1 | <0.1 | 1.21 | 6.12 | 3.12 |
| C98 (A48+T33V+A98V) | <0.1 | <0.1 | 1.29 | 8.94 | 6.70 |
| D118 (A48+F28W+T33V) | <0.1 | <0.1 | 9.07 | 24.35 | 12.61 |
| A11 (Assay #1) | 0.35 | 0.11 | 16.83 | 110.00 | 56.30 |
| A11 (Assay #2) | 0.269 | <0.1 | 18.03 | 89.71 | |

Fig. 8

| MAb | EDIII-DV1 Kd (nM) | EDIII-DV2 Kd (nM) | EDIII-DV3 Kd (nM) | EDIII-DV4 Kd (nM) |
|---|---|---|---|---|
| C88 (A48+T33V) | 2.83E-11 | 1.32E-11 | 5.56E-10 | 1.45E-08 |
| D88 (A48+T33V+del26) | 4.81E-11 | 3.02E-11 | 6.58E-10 | 2.79E-09 |
| C98 (A48+T33V+A98V) | 1.07E-10 | 3.24E-11 | 8.62E-10 | 6.60E-09 |
| B11 | | | | 9.65E-09 |
| A11 | | | | 5.03E-08 |

Fig. 9

| Serotype | EDIII strain | Genotype | $K_D$ by ELISA (nM) | $K_D$ by SPR (nM) |
|---|---|---|---|---|
| I | Hawaii/1944* | I | <0.1 | 0.041 |
| | Vietnam/2008 | I | <0.1 | 0.031 |
| | Malaysia/2005 | IV | <0.1 | 0.064 |
| | Mexico/2007 | V | <0.1 | 0.071 |
| II | New Guinea/1944 (NGC)* | Asian I | <0.1 | 0.016 |
| | Singapore/2008 | Cosmopolitan | <0.1 | 0.024 |
| | Peru/1995 | American | <0.1 | 0.012 |
| | Vietnam/2007 | Asian II | <0.1 | 0.014 |
| | Venezuela/2007 | SE-Asian/American | <0.1 | 0.029 |
| III | Philippines/1956 (H87)* | I | 1.24 | 1.00 |
| | Singapore/2009 | I | 0.35 | 0.61 |
| | Nicaragua/2010 | III | 3.36 | 4.91 |
| | Puerto Rico/1977 | IV | 1.36 | 1.40 |
| | Cambodia/2008 | II | 1.32 | 2.47 |
| IV | Mexico/1977 (BC287/97)* | IIa | 4.32 | 3.8 |
| | Singapore/2010 | IIb | 8.43 | 6.1 |
| | New Caledonia/2009 | IIb | 10.81 | 8.9 |
| | Philippines/1956 (H241)* | I | 113.10 | 118.5 |
| | Brazil/2011 | I | 14.68 | 7.9 |
| | Venezuela/2008 | IIa | 4.50 | 3.03 |
| | Thailand/1997 | III | 611.60 | >300 |

Fig. 10B

| | | Antibody Construct Kd (nM) | | | | | |
|---|---|---|---|---|---|---|---|
| | Ag | 4E11 | A11 | A88 | B88 | C88 | D88 |
| DENV-4 | BC2 | 40,793 | 86.2 | 22.5 | 17.3 | 10.6 | 7.2 |
| | Sing | | 136.3 | 34.1 | 24.6 | 15 | 8.4 |
| | NC | | 201.6 | 24.3 | 37.1 | 11.3 | 10.8 |
| | Phil | | 507.5 | 415.4 | 491.1 | 234 | 148 |
| DENV-3 | Sing | | 7.5 | 3 | 3.1 | 1 | 0.33 |
| | Nic | | 32.1 | 13.7 | 23.3 | 3.2 | 3.3 |
| | H87 | 21.8 | 14.1 | 5.5 | 7.9 | 1.5 | 1.2 |
| DENV-2 | Peru | | 0.39 | 0.49 | 0.42 | 0.38 | <0.1 |
| | Sing | | <0.1 | <0.1 | <0.1 | <0.1 | <0.1 |
| | NGC | 5.2 | <0.1 | <0.1 | 0.14 | <0.1 | <0.1 |

Fig. 11

| Antibody name | Heavy chain description | Light chain description | $T_m$ (°C) |
|---|---|---|---|
| C51/mouse | A48+G27Y+F28W | Mouse (A11) | 65.7 |
| C61/mouse | A48+K31S+T33V | Mouse (A11) | 67.5 |
| C71/mouse | A48+K31Q+T33V | Mouse A11) | 66.8 |
| C81/mouse | A48+T33V | Mouse (A11) | 67.4 |
| C58 | A48+G27Y+F28W | Human (A48) | 64.1 |
| C68 | A48+K31S+T33V | Human (A48) | 66.8 |
| C78 | A48+K31Q+T33V | Human (A48) | 66.3 |
| C88 | A48+T33V | Human (A48) | 66.4 |
| A11 | mouse | mouse | 64.8 |
| B11 | mouse | mouse | 62.7 |
| Trastuzumab | | | 69.1 |

Fig. 15A

| Sample | A48 | A68 (A48+ A98V) | B48 | B48+ A98V | A48+ del26+ L64F | A48+ del26 T33V+L64F | A48+ T33V +del26 | A48+ L64F | A48+ T33V |
|---|---|---|---|---|---|---|---|---|---|
| Tm | 66.3 | 62.5 | 64.1 | 58.3 | 65.7 | 62.5 | 61.9 | 67.4 | 66.4 |

Fig. 15B

| Sample | A48 | A68 (A48+ A98V) | B48 | B48+ A98V | A48+ del26+ L64F | A48+ del26 T33V+L64F | A48+ T33V +del26 | A48+ L64F | A48+ T33V |
|---|---|---|---|---|---|---|---|---|---|
| Tm | 66.3 | 62.5 | 64.1 | 58.3 | 65.7 | 62.5 | 61.9 | 67.4 | 66.4 |

Fig. 15C

| | DENV-1 (Hawaii/1944) FRNT$_{50}$ (ng/ml) | DENV-2 (New Guinea/1944; NGC) FRNT$_{50}$ (ng/ml) | DENV-3 (Philippines/1956; H87) FRNT$_{50}$ (ng/ml) | DENV-4 (Mexico/1997; BC287/97) FRNT$_{50}$ (ng/ml) |
|---|---|---|---|---|
| Ab | 449 | 48 | 338 | 417 |

Fig. 20

| | 4E11 | D88 | Fold Enhancement |
|---|---|---|---|
| DENV-1 EDIII $K_D$ (nM) | 0.33 | 0.041 | 8 |
| DENV-2 EDIII $K_D$ (nM) | 5.20 | 0.016 | 325 |
| DENV-3 EDIII $K_D$ (nM) | 21.8 | 1.00 | 22 |
| DENV-4 EDIII $K_D$ (nM) | 40,800 | 3.80 | 10,700 |

Fig. 23

```
SEQUENCE LISTING

<160> NUMBER OF SEQ ID NOS: 98

<210> SEQ ID NO 1
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Gly Phe Asn Ile Lys Asp Val Tyr
            20                  25                  30

Met Ser Trp Val Arg Gln Ala Pro Glu Gln Gly Leu Glu Trp Met Gly
        35                  40                  45

Arg Ile Asp Pro Glu Asn Gly Asp Thr Lys Tyr Asp Pro Lys Leu Gln
    50                  55                  60

Gly Arg Val Thr Met Thr Ala Asp Thr Ser Thr Asn Thr Ala Tyr Met
65                  70                  75                  80

Glu Leu Arg Ser Leu Arg Ser Asp Asp Thr Ala Val Tyr Tyr Cys Ala
                85                  90                  95

Arg Gly Trp Glu Gly Phe Ala Tyr Trp Gly Gln Gly Thr Leu Val Thr
            100                 105                 110

Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Ala Ser Leu Ala Val Ser Leu Gly
1               5                   10                  15

Glu Arg Ala Thr Ile Ser Cys Arg Ala Ser Glu Asn Val Asp Lys Tyr
            20                  25                  30

Gly Asn Ser Phe Met His Trp Tyr Gln Gln Lys Pro Gly Gln Pro Pro
        35                  40                  45
```

```
Lys Leu Leu Ile Tyr Arg Ala Ser Glu Leu Gln Trp Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Arg Ser Asn
                 85                  90                  95

Glu Val Pro Trp Thr Phe Gly Gln Gly Thr Lys Leu Glu Ile Lys
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Val Tyr Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ile Asp Pro Glu Asn Gly Asp Thr Lys Tyr Asp Pro Lys Leu Gln
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Trp Glu Gly Phe Ala Tyr
1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Glu Asn Val Asp Lys Tyr Gly Asn Ser Phe Met His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Arg Ala Ser Glu Leu Gln Trp
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Arg Ser Asn Glu Val Pro Trp Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Asn Ile Lys Asp Val
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Pro Glu Asn Gly Asp
1               5

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Gly Phe Asn Ile Lys
            20                  25

<210> SEQ ID NO 12

<400> SEQUENCE: 12

000

<210> SEQ ID NO 13

<400> SEQUENCE: 13

000
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Tyr Met Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Asn Ile Lys Asp Thr
1               5

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
            100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Val
            20                  25                  30
```

Tyr Met Ser Trp Val Arg Gln Ala Pro Glu Gln Gly Leu Glu Trp Met
         35                  40                  45

Gly Arg Ile Asp Pro Glu Asn Gly Asp Thr Lys Tyr Asp Pro Lys Leu
 50                  55                  60

Gln Gly Arg Val Thr Met Thr Ala Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Trp Glu Gly Phe Ala Tyr Trp Gly Gln Gly Thr Leu Val
                100                 105                 110

Thr Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Gly Phe Asn Ile Lys Asp Thr Tyr
                 20                  25                  30

Met Ser Trp Val Arg Gln Ala Pro Glu Gln Gly Leu Glu Trp Met Gly
             35                  40                  45

Arg Ile Asp Pro Glu Asn Gly Asp Thr Lys Tyr Asp Pro Lys Leu Gln
 50                  55                  60

Gly Arg Val Thr Met Thr Ala Asp Thr Ser Thr Asn Thr Ala Tyr Met
 65                  70                  75                  80

Glu Leu Arg Ser Leu Arg Ser Asp Asp Thr Ala Val Tyr Tyr Cys Ala
                 85                  90                  95

Arg Gly Trp Glu Gly Phe Ala Tyr Trp Gly Gln Gly Thr Leu Val Thr
                100                 105                 110

Val Ser Ser
        115

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                 20                  25                  30

Tyr Met Ser Trp Val Arg Gln Ala Pro Glu Gln Gly Leu Glu Trp Met
         35                  40                  45

Gly Arg Ile Asp Pro Glu Asn Gly Asp Thr Lys Tyr Asp Pro Lys Leu
 50                  55                  60

Gln Gly Arg Val Thr Met Thr Ala Asp Thr Ser Thr Asn Thr Ala Tyr
 65                  70                  75                  80

```
Met Glu Leu Arg Ser Leu Arg Ser Asp Asp Thr Ala Val Tyr Tyr Cys
                85                  90                  95

Val Arg Gly Trp Glu Gly Phe Ala Tyr Trp Gly Gln Gly Thr Leu Val
            100                 105                 110

Thr Val Ser Ser
        115

<210> SEQ ID NO 20
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ser Arg Gly Trp Glu Gly Phe Ala Tyr Trp Gly Gln Gly Thr Leu Val
            100                 105                 110

Thr Val Ser Ser
        115

<210> SEQ ID NO 21
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Tyr Trp Asn Ile Lys Asp Thr
            20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
            100                 105                 110

Thr Val Ser Ser
        115
```

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Trp Asn Ile Lys Asp Thr
1               5

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Gln Asp Val
            20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
            100                 105                 110

Thr Val Ser Ser
        115

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Asn Ile Gln Asp Val
1               5

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Ser Asp Val
            20                  25                  30

```
Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
 50                  55                  60

Gln Gly Arg Val Thr Met Thr Ala Asp Thr Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
                    100                 105                 110

Thr Val Ser Ser
        115

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Asn Ile Ser Asp Val
 1               5

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Ala Phe Asn Ile Lys Asp Thr
                20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
 50                  55                  60

Gln Gly Arg Val Thr Met Thr Ala Asp Thr Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
                    100                 105                 110

Thr Val Ser Ser
        115

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

Ala Phe Asn Ile Lys Asp Thr
1               5

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Ala Phe Asn Ile Lys Asp Val
                20                  25                  30

Tyr Met Ser Trp Val Arg Gln Ala Pro Glu Gln Gly Leu Glu Trp Met
            35                  40                  45

Gly Arg Ile Asp Pro Glu Asn Gly Asp Thr Lys Tyr Asp Pro Lys Leu
        50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
            100                 105                 110

Thr Val Ser Ser
        115

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Phe Asn Ile Lys Asp Val
1               5

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Val
                20                  25                  30

Tyr Met Ser Trp Val Arg Gln Ala Pro Glu Gln Gly Leu Glu Trp Met
            35                  40                  45

Gly Arg Ile Asp Pro Glu Asn Gly Asp Thr Lys Tyr Asp Pro Lys Leu
        50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys

Ser Arg Gly Trp Glu Gly Phe Ala Tyr Trp Gly Gln Gly Thr Leu Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Val
            20                  25                  30

Tyr Met Ser Trp Val Arg Gln Ala Pro Glu Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Val Arg Gly Trp Glu Gly Phe Ala Tyr Trp Gly Gln Gly Thr Leu Val
            100                 105                 110

Thr Val Ser Ser
        115

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Lys Leu Leu Glu Gln Ser Gly Ala Glu Leu Val Lys Pro Gly
1               5                   10                  15

Ala Ser Val Arg Leu Ser Cys Thr Ala Ser Gly Phe Asn Ile Lys Asp
            20                  25                  30

Thr Tyr Met Ser Trp Val Lys Gln Arg Pro Glu Gln Gly Leu Glu Trp
        35                  40                  45

Ile Gly Arg Ile Asp Pro Glu Asn Gly Asp Thr Lys Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu His Leu Ser Ser Leu Thr Ser Gly Asp Thr Ala Val Tyr Tyr
                85                  90                  95

Cys Ser Arg Gly Trp Glu Gly Phe Ala Tyr Trp Gly Gln Gly Thr Leu
            100                 105                 110

Val Thr Val Ser Ala
        115

```
<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Leu Val Met Thr Gln Thr Pro Ala Ser Leu Ala Val Ser Leu Gly
1               5                   10                  15

Gln Arg Ala Thr Ile Ser Cys Arg Ala Ser Glu Asn Val Asp Lys Tyr
            20                  25                  30

Gly Asn Ser Phe Met His Trp Tyr Gln Gln Lys Ala Gly Gln Pro Pro
        35                  40                  45

Lys Leu Leu Ile Tyr Arg Ala Ser Glu Leu Gln Trp Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Phe Cys Gln Arg Ser Asn
                85                  90                  95

Glu Val Pro Trp Thr Phe Gly Gly Gly Thr Lys Leu Glu Ile Lys
            100                 105                 110

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ile Asp Pro Glu Asn Gly Asp Thr Lys Tyr Asp Pro Lys Phe Gln
1               5                   10                  15

Gly

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Lys Leu Leu Glu Gln Ser Gly Ala Glu Leu Val Lys Pro Gly
1               5                   10                  15

Ala Ser Val Arg Leu Ser Cys Thr Ala Gly Phe Asn Ile Lys Asp Thr
            20                  25                  30

Tyr Met Ser Trp Val Lys Gln Arg Pro Glu Gln Gly Leu Glu Trp Ile
        35                  40                  45

Gly Arg Ile Asp Pro Glu Asn Gly Asp Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Gly Asp Thr Ala Val Tyr Tyr Cys
                85                  90                  95

Ser Arg Gly Trp Glu Gly Phe Ala Tyr Trp Gly Gln Gly Thr Leu Val
            100                 105                 110
```

Thr Val Ser Ala
    115

<210> SEQ ID NO 37
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
caagtgcaac tcgttcagtc cggagcagaa gtcaagaaac ctggagcttc agtcaaagtc      60
agctgcaagg ccggcttcaa tatcaaggac gtctacatgt cctgggtgcg gcaggctcca     120
gagcaaggac tggaatggat ggggcgcatt gacccggaga acggtgatac gaagtacgac     180
ccgaaactgc agggccgcgt gaccatgacc gcagatacta gcaccaacac cgcgtacatg     240
gagctgcggt ccttgaggtc ggatgacact gctgtgtatt actgtgccag aggctgggaa     300
gggttcgcgt actggggaca gggaactctc gtgactgtgt cgtct                    345

<210> SEQ ID NO 38
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gatattgtca tgacccaaag cccagcctcc ctcgccgtgt ctctcggaga aagagcaact      60
atctcgtgcc gggcttcgga gaatgtggac aagtacggca actccttcat gcactggtac     120
cagcagaaac cgggacagcc gcctaaactg ttgatctacc gggcgtcaga actgcaatgg     180
ggagtgcctg acaggttttc gggttcggga tccggcacgg atttcaccct cactatctcc     240
agcctgcaag cagaggacgt tgcggtgtac tactgtcagc gctcaaacga ggtcccatgg     300
acttttggac aagggaccaa gctggaaatc aag                                  333

<210> SEQ ID NO 39
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caagtgcaac tcgttcagtc cggagcagaa gtcaagaaac ctggagcttc agtcaaagtc      60
agctgcaagg cctcgggctt caatatcaag gacacctaca tgtcctgggt gcggcaggct    120
ccagagcaag gactgaatg gatggggcgc attgacccgg agaacggtga tacgaagtac     180
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                 348

<210> SEQ ID NO 40
<211> LENGTH: 348
<212> TYPE: DNA
<213> ORGANISM: Artificial Sequence
<220> FEATURE:
<223> OTHER INFORMATION: Description of Artificial Sequence: Synthetic

<400> SEQUENCE: 40

```
caagtgcaac tcgttcagtc cggagcagaa gtcaagaaac ctggagcttc agtcaaagtc    60
agctgcaagg cctcgggctt caatatcaag gacgtctaca tgtcctgggt gcggcaggct   120
ccagagcaag gactggaatg gatggggcgc attgacccgg agaacggtga tacgaagtac   180
gacccgaaac tgcagggccg cgtgaccatg accgcagata ctagcaccaa caccgcgtac   240
atggagctgc ggtccttgag gtcggatgac actgctgtgt attactgtgc cagaggctgg   300
gaagggttcg cgtactgggg acagggaact ctcgtgactg tgtcgtct              348
```

<210> SEQ ID NO 41
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
caagtgcaac tcgttcagtc cggagcagaa gtcaagaaac ctggagcttc agtcaaagtc    60
agctgcaagg ccggcttcaa tatcaaggac acctacatgt cctgggtgcg gcaggctcca   120
gagcaaggac tggaatggat ggggcgcatt gacccgagac gtgatac gaagtacgac     180
ccgaaactgc agggccgcgt gaccatgacc gcagatacta gcaccaacac cgcgtacatg   240
gagctgcggt ccttgaggtc ggatgacact gctgtgtatt actgtgccag aggctgggaa   300
gggttcgcgt actggggaca gggaactctc gtgactgtgt cgtct                  345
```

<210> SEQ ID NO 42
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
caagtgcaac tcgttcagtc cggagcagaa gtcaagaaac ctggagcttc agtcaaagtc    60
agctgcaagg cctcgggctt caatatcaag gacacctaca tgtcctgggt gcggcaggct   120
ccagagcaag gactggaatg gatggggcgc attgacccgg agaacggtga tacgaagtac   180
gacccgaaac tgcagggccg cgtgaccatg accgcagata ctagcaccaa caccgcgtac   240
atggagctgc ggtccttgag gtcggatgac actgctgtgt attactgtgt cagaggctgg   300
gaagggttcg cgtactgggg acagggaact ctcgtgactg tgtcgtct              348
```

<210> SEQ ID NO 43
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
caagtgcaac tcgttcagtc cggagcagaa gtcaagaaac ctggagcttc agtcaaagtc    60
agctgcaagg cctcgtactg gaatatcaag gacacctaca tgtcctgggt gcggcaggct   120
ccagagcaag gactggaatg gatggggcgc attgacccgg agaacggtga tacgaagtac   180
```
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                348

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caagtgcaac tcgttcagtc cggagcagaa gtcaagaaac ctggagcttc agtcaaagtc    60
agctgcaagg cctcgggctt caatatccag gacgtctaca tgtcctgggt gcggcaggct    120
ccagagcaag gactggaatg gatggggcgc attgacccgg agaacggtga tacgaagtac    180
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                348

<210> SEQ ID NO 45
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
caagtgcaac tcgttcagtc cggagcagaa gtcaagaaac ctggagcttc agtcaaagtc    60
agctgcaagg cctcgggctt caatatctcg gacgtctaca tgtcctgggt gcggcaggct    120
ccagagcaag gactggaatg gatggggcgc attgacccgg agaacggtga tacgaagtac    180
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                348

<210> SEQ ID NO 46
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caagtgcaac tcgttcagtc cggagcagaa gtcaagaaac ctggagcttc agtcaaagtc    60
agctgcaagg cctcggcctt caatatcaag gacacctaca tgtcctgggt gcggcaggct    120
ccagagcaag gactggaatg gatggggcgc attgacccgg agaacggtga tacgaagtac    180
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                348

<210> SEQ ID NO 47
<211> LENGTH: 351
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 47

```
caagtcaaac tgctggaaca gtccggagca gagctggtga agcctggagc gtcggtgcgg    60
ctttcgtgta ccgcctccgg ctttaacatc aaggacacct acatgtcgtg ggtgaagcag   120
aggcccgagc aggggctcga atggattggc cgcatcgacc cggaaaatgg tgataccaaa   180
tacgacccaa agttccaggg aaaggccact atcactgcag atacttcaag caacaccgcc   240
tacctccacc tgtcctcgct cacttccgga gataccgcgg tctactattg ctcaagagga   300
tgggaaggct tcgcgtactg gggtcaagga acgttggtga ccgtcagcgc c            351
```

<210> SEQ ID NO 48
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gaattggtca tgactcagac gccagcttcg ctggccgtgt cactgggaca gagggccact    60
atcagctgca gagcatcgga gaatgtggat aagtacggga acagcttcat gcactggtat   120
caacagaaag ctggtcaacc tccgaagctg cttatctacc gggcgtcgga actccaatgg   180
ggcattccag cacggttcag cgggtcgggc tccagaactg acttcaccct caccatcaat   240
cccgtggagg ccgatgacgt ggcgacctac ttttgtcagc gctccaacga ggtcccgtgg   300
actttcggag gaggaaccaa gctggaaatc aag                                333
```

<210> SEQ ID NO 49
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
caagtcaaac tgctggaaca gtccggagca gagctggtga agcctggagc gtcggtgcgg    60
ctttcgtgta ccgccggctt taacatcaag gacacctaca tgtcgtgggt gaagcagagg   120
cccgagcagg ggctcgaatg gattggccgc atcgacccgg aaaatggtga taccaaatac   180
gacccaaagt tccagggaaa ggccactatc actgcagata cttcaagcaa caccgcctac   240
ctccacctgt cctcgctcac ttccggagat accgcggtct actattgctc aagaggatgg   300
gaaggcttcg cgtactgggg tcaaggaacg ttggtgaccg tcagcgcc                 348
```

<210> SEQ ID NO 50
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Met Thr Leu Lys Gly Met Ser Tyr Val Met Cys Thr Gly Ser Phe Lys
1               5                   10                  15
```

```
Leu Glu Lys Glu Val Ala Glu Thr Gln His Gly Thr Val Leu Val Gln
            20                  25                  30

Val Lys Tyr Glu Gly Thr Asp Ala Pro Cys Lys Ile Pro Phe Ser Thr
        35                  40                  45

Gln Asp Glu Lys Gly Ala Thr Gln Asn Gly Arg Leu Ile Thr Ala Asn
 50                  55                  60

Pro Ile Val Thr Asp Lys Glu Lys Pro Val Asn Ile Glu Ala Glu Pro
 65                  70                  75                  80

Pro Phe Gly Glu Ser Tyr Ile Val Val Gly Ala Gly Lys Ala Leu
            85                  90                  95

Lys Leu Ser Trp Phe Lys Lys Gly Ser Ser Ile Gly Lys
            100                 105
```

<210> SEQ ID NO 51
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Gln Leu Lys Gly Met Ser Tyr Ser Met Cys Thr Gly Lys Phe Lys
 1               5                  10                  15

Val Val Lys Glu Ile Ala Glu Thr Gln His Gly Thr Ile Val Ile Arg
            20                  25                  30

Val Gln Tyr Glu Gly Asp Gly Ser Pro Cys Lys Ile Pro Phe Glu Ile
        35                  40                  45

Met Asp Leu Glu Lys Arg His Val Leu Gly Arg Leu Ile Thr Val Asn
 50                  55                  60

Pro Ile Val Thr Glu Lys Asp Ser Pro Val Asn Ile Glu Ala Glu Pro
 65                  70                  75                  80

Pro Phe Gly Asp Ser Tyr Ile Ile Ile Gly Val Glu Pro Gly Gln Leu
            85                  90                  95

Lys Leu Asn Trp Phe Lys Lys Gly Ser Ser Leu Glu
            100                 105
```

<210> SEQ ID NO 52
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Lys Leu Lys Gly Met Ser Tyr Ala Met Cys Leu Asn Thr Phe Val
 1               5                  10                  15

Leu Lys Lys Glu Val Ser Glu Thr Gln His Gly Thr Ile Leu Ile Lys
            20                  25                  30

Val Glu Tyr Lys Gly Glu Asp Ala Pro Cys Lys Ile Pro Phe Ser Thr
        35                  40                  45

Glu Asp Gly Gln Gly Lys Ala His Asn Gly Arg Leu Ile Thr Ala Asn
 50                  55                  60

Pro Val Val Thr Lys Lys Glu Glu Pro Val Asn Ile Glu Ala Glu Pro
 65                  70                  75                  80

Pro Phe Gly Glu Ser Asn Ile Val Ile Gly Ile Gly Asp Lys Ala Leu
            85                  90                  95
```

```
Lys Ile Asn Trp Tyr Arg Lys Gly Ser Ser Ile Gly Lys
            100                 105
```

```
<210> SEQ ID NO 53
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Thr Val Val Lys
            20                  25                  30

Val Lys Tyr Glu Gly Ala Gly Ala Pro Cys Lys Val Pro Ile Glu Ile
        35                  40                  45

Arg Asp Val Asn Lys Glu Lys Val Val Gly Arg Ile Ile Ser Ser Thr
50                  55                  60

Pro Leu Ala Glu Asn Thr Asn Ser Val Thr Asn Ile Glu Leu Glu Pro
65                  70                  75                  80

Pro Phe Gly Asp Ser Tyr Ile Val Ile Gly Val Gly Asn Ser Ala Leu
                85                  90                  95

Thr Leu His Trp Phe Arg Lys Gly Ser Ser Ile Gly Lys
            100                 105
```

```
<210> SEQ ID NO 54
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Thr Leu Lys Gly Met Ser Tyr Val Met Cys Thr Gly Ser Phe Lys
1               5                   10                  15

Leu Glu Lys Glu Leu Ala Glu Thr Gln His Gly Thr Val Leu Val Gln
            20                  25                  30

Ile Lys Tyr Glu Gly Thr Asp Ala Pro Cys Lys Ile Pro Phe Ser Thr
        35                  40                  45

Gln Asp Glu Lys Gly Val Thr Gln Asn Gly Arg Leu Ile Thr Ala Asn
50                  55                  60

Pro Ile Val Thr Asp Lys Glu Lys Pro Val Asn Ile Glu Ala Glu Pro
65                  70                  75                  80

Pro Phe Gly Glu Ser Tyr Ile Val Ile Gly Ala Gly Glu Lys Ala Leu
                85                  90                  95

Lys Leu Ser Trp Phe Lys Lys Gly Ser Ser Ile Gly Lys
            100                 105
```

```
<210> SEQ ID NO 55
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Thr Leu Lys Gly Ile Ser Tyr Val Met Cys Thr Gly Pro Phe Lys
```

```
            1               5                  10                 15
Leu Glu Lys Glu Val Ala Glu Thr Gln His Gly Thr Val Leu Val Gln
            20                 25                 30

Val Lys Tyr Glu Gly Thr Asp Ala Pro Cys Lys Ile Pro Phe Ser Ser
            35                 40                 45

Gln Asp Glu Lys Gly Val Thr Gln Asn Gly Arg Leu Val Thr Ala Asn
            50                 55                 60

Pro Ile Val Thr Asp Lys Glu Lys Pro Val Asn Ile Glu Ala Glu Pro
65                  70                 75                 80

Pro Phe Gly Glu Ser Tyr Ile Val Val Gly Ala Gly Glu Lys Ala Leu
                    85                 90                 95

Lys Leu Ser Trp Phe Lys Lys Gly Ser Ser Ile Gly Lys
                    100                105

<210> SEQ ID NO 56
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Thr Leu Lys Gly Thr Ser Tyr Val Met Cys Thr Gly Ser Phe Lys
1               5                  10                 15

Leu Glu Lys Glu Val Ala Glu Thr Gln His Gly Thr Val Leu Val Gln
            20                 25                 30

Val Lys Tyr Glu Gly Thr Asp Ala Pro Cys Lys Ile Pro Phe Ser Thr
            35                 40                 45

Gln Asp Glu Lys Gly Val Thr Gln Asn Gly Arg Leu Ile Thr Ala Asn
            50                 55                 60

Pro Ile Val Thr Asp Lys Glu Lys Pro Val Asn Ile Glu Thr Glu Pro
65                  70                 75                 80

Pro Phe Gly Glu Ser Tyr Ile Val Val Gly Ala Gly Glu Lys Ala Leu
                    85                 90                 95

Lys Leu Ser Trp Phe Lys Lys Gly Ser Ser Ile Gly Lys
                    100                105

<210> SEQ ID NO 57
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gln Leu Lys Gly Met Ser Tyr Ser Met Cys Thr Gly Lys Phe Lys
1               5                  10                 15

Val Val Lys Glu Ile Ala Glu Thr Gln His Gly Thr Ile Val Ile Arg
            20                 25                 30

Val Gln Tyr Glu Gly Asp Gly Ser Pro Cys Lys Ile Pro Phe Glu Ile
            35                 40                 45

Met Asp Leu Glu Lys Arg His Val Leu Gly Arg Leu Ile Thr Val Asn
            50                 55                 60

Pro Ile Val Thr Glu Lys Asp Ser Pro Val Asn Ile Glu Ala Glu Pro
65                  70                 75                 80

Pro Phe Gly Asp Ser Tyr Ile Ile Ile Gly Val Glu Pro Gly Gln Leu
```

```
                    85                  90                  95

Lys Leu Ser Trp Phe Lys Lys Gly Ser Ser Ile Gly Gln
            100                 105

<210> SEQ ID NO 58
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gln Leu Lys Gly Met Ser Tyr Ser Met Cys Thr Gly Lys Phe Lys
1               5                   10                  15

Ile Val Lys Glu Ile Ala Glu Thr Gln His Gly Thr Ile Val Ile Arg
            20                  25                  30

Ile Gln Tyr Glu Gly Asp Gly Ser Pro Cys Lys Ile Pro Phe Glu Ile
        35                  40                  45

Thr Asp Leu Glu Lys Arg His Val Leu Gly Arg Leu Ile Thr Val Asn
    50                  55                  60

Pro Ile Val Ile Glu Lys Asp Ser Pro Val Asn Ile Glu Ala Glu Pro
65                  70                  75                  80

Pro Phe Gly Asp Ser Tyr Ile Ile Gly Val Glu Pro Gly Gln Leu
                85                  90                  95

Lys Leu Asn Trp Phe Lys Lys Gly Ser Ser Ile Gly Gln
            100                 105

<210> SEQ ID NO 59
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gln Leu Lys Gly Met Ser Tyr Ser Met Cys Thr Gly Lys Phe Lys
1               5                   10                  15

Ile Val Lys Glu Ile Ala Glu Thr Gln His Gly Thr Ile Val Ile Arg
            20                  25                  30

Val Gln Tyr Glu Gly Asp Gly Ser Pro Cys Lys Ile Pro Phe Glu Ile
        35                  40                  45

Met Asp Leu Glu Lys Arg His Val Leu Gly Arg Leu Ile Thr Val Asn
    50                  55                  60

Pro Ile Val Thr Glu Lys Asp Ser Pro Val Asn Ile Glu Ala Glu Pro
65                  70                  75                  80

Pro Phe Gly Asp Ser Tyr Ile Ile Gly Val Glu Pro Gly Gln Leu
                85                  90                  95

Lys Leu Asp Trp Phe Lys Lys Gly Ser Ser Ile Gly Gln
            100                 105

<210> SEQ ID NO 60
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60
```

Met Gln Leu Lys Gly Met Ser Tyr Ser Met Cys Thr Gly Lys Phe Lys
1               5                   10                  15

Val Val Lys Glu Ile Ala Glu Thr Gln His Gly Thr Ile Val Ile Arg
            20                  25                  30

Val Gln Tyr Glu Gly Asp Gly Ser Pro Cys Lys Ile Pro Phe Glu Ile
            35                  40                  45

Met Asp Leu Glu Lys Arg Tyr Val Leu Gly Arg Leu Ile Thr Val Asn
50                  55                  60

Pro Ile Val Thr Glu Lys Asp Ser Pro Ile Asn Ile Glu Ala Glu Pro
65                  70                  75                  80

Pro Phe Gly Asp Ser Tyr Ile Ile Ile Gly Val Glu Pro Gly Gln Leu
            85                  90                  95

Lys Leu Asn Trp Phe Lys Lys Gly Ser Ser Ile Gly Gln
            100                 105

<210> SEQ ID NO 61
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Leu Lys Gly Met Ser Tyr Ala Met Cys Leu Asn Thr Phe Val
1               5                   10                  15

Leu Lys Lys Glu Val Ser Glu Thr Gln His Gly Thr Ile Leu Ile Lys
            20                  25                  30

Val Glu Tyr Lys Gly Glu Asp Ala Pro Cys Lys Ile Pro Phe Ser Thr
            35                  40                  45

Glu Asp Gly Gln Gly Lys Ala His Ser Gly Arg Leu Ile Thr Ala Asn
50                  55                  60

Pro Val Val Thr Lys Lys Glu Glu Pro Val Asn Ile Glu Ala Glu Pro
65                  70                  75                  80

Pro Phe Gly Glu Ser Asn Ile Val Ile Gly Ile Gly Asp Lys Ala Leu
            85                  90                  95

Lys Ile Asn Trp Tyr Lys Lys Gly Ser Ser Ile Gly Lys
            100                 105

<210> SEQ ID NO 62
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Glu Leu Lys Gly Met Ser Tyr Ala Met Cys Gln Asn Ala Phe Val
1               5                   10                  15

Leu Lys Lys Glu Val Ser Glu Thr Gln His Gly Thr Ile Leu Ile Lys
            20                  25                  30

Val Glu Tyr Lys Gly Glu Asp Ala Pro Cys Lys Ile Pro Phe Ser Thr
            35                  40                  45

Glu Asp Gly Gln Gly Lys Ala His Asn Gly Arg Leu Ile Thr Ala Asn
50                  55                  60

Pro Val Val Thr Lys Lys Glu Glu Pro Val Asn Ile Glu Ala Glu Pro
65                  70                  75                  80

```
Pro Phe Gly Glu Ser Asn Ile Val Ile Gly Ile Gly Asp Lys Ala Leu
                85                  90                  95

Lys Ile Asn Trp Tyr Lys Lys Gly Ser Ser Ile Gly Lys
            100                 105
```

<210> SEQ ID NO 63
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Glu Leu Lys Gly Met Ser Tyr Ala Met Cys Thr Asn Thr Phe Val
1               5                   10                  15

Leu Lys Lys Glu Val Ser Glu Thr Gln His Gly Thr Ile Leu Ile Lys
                20                  25                  30

Val Glu Tyr Lys Gly Glu Asp Val Pro Cys Lys Ile Pro Phe Ser Thr
            35                  40                  45

Glu Asp Gly Gln Gly Lys Ala His Asn Gly Arg Leu Ile Thr Ala Asn
    50                  55                  60

Pro Val Val Thr Lys Lys Glu Glu Pro Val Asn Ile Glu Ala Glu Pro
65                  70                  75                  80

Pro Phe Gly Glu Ser Asn Ile Val Ile Gly Ile Gly Asp Asn Ala Leu
                85                  90                  95

Lys Ile Asn Trp Tyr Lys Lys Gly Ser Ser Ile Gly Lys
            100                 105
```

<210> SEQ ID NO 64
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Glu Leu Lys Gly Met Ser Tyr Ala Met Cys Ser Gly Thr Phe Val
1               5                   10                  15

Leu Lys Lys Glu Val Ser Glu Thr Gln His Gly Thr Ile Leu Ile Lys
                20                  25                  30

Ile Glu Tyr Lys Gly Glu Asp Ala Pro Cys Lys Ile Pro Phe Ser Thr
            35                  40                  45

Glu Asp Ala Gln Gly Lys Ala His Asn Gly Arg Leu Ile Thr Ala Asn
    50                  55                  60

Pro Val Val Thr Lys Lys Glu Glu Pro Val Asn Ile Glu Ala Glu Pro
65                  70                  75                  80

Pro Phe Gly Glu Ser Asn Ile Val Ile Gly Thr Gly Asp Lys Ala Leu
                85                  90                  95

Arg Ile Asn Trp Tyr Lys Lys Gly Ser Ser Ile Gly Lys
            100                 105
```

<210> SEQ ID NO 65
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Thr Val Val Lys
                20                  25                  30

Val Lys Tyr Glu Gly Ala Gly Ala Pro Cys Lys Val Pro Ile Glu Ile
            35                  40                  45

Arg Asp Val Asn Lys Glu Lys Val Val Gly Arg Val Ile Ser Ala Thr
        50                  55                  60

Pro Leu Ala Glu Asn Thr Asn Ser Val Thr Asn Ile Glu Leu Glu Pro
65                  70                  75                  80

Pro Phe Gly Asp Ser Tyr Ile Val Ile Gly Val Gly Asn Ser Ala Leu
                85                  90                  95

Thr Leu His Trp Phe Arg Lys Gly Ser Ser Ile Gly Lys
            100                 105

<210> SEQ ID NO 66
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Thr Val Val Lys
                20                  25                  30

Val Lys Tyr Glu Gly Ala Gly Ala Pro Cys Lys Val Pro Ile Glu Ile
            35                  40                  45

Arg Asp Val Asn Lys Glu Lys Val Val Gly Arg Ile Ile Ser Ser Thr
        50                  55                  60

Pro Phe Ala Glu Asn Thr Asn Ser Val Thr Asn Ile Glu Leu Glu Pro
65                  70                  75                  80

Pro Phe Gly Asp Ser Tyr Ile Val Ile Gly Val Gly Asp Ser Ala Leu
                85                  90                  95

Thr Leu His Trp Phe Arg Lys Gly Ser Ser Ile Gly Lys
            100                 105

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Thr Val Val Lys
                20                  25                  30

Val Lys Tyr Glu Gly Ala Gly Ala Pro Cys Lys Ile Pro Ile Glu Ile
            35                  40                  45

Arg Asp Val Asn Lys Glu Lys Val Val Gly Arg Ile Ile Ser Ser Thr
        50                  55                  60

Pro Phe Ala Glu Asn Thr Asn Ser Val Ile Asn Ile Glu Leu Glu Pro
65                  70                  75                  80

Pro Phe Gly Asp Ser Tyr Ile Val Ile Gly Val Gly Asp Ser Ala Leu
                85                  90                  95

Thr Leu His Trp Phe Arg Lys Gly Ser Ser Ile Gly Lys
            100                 105

<210> SEQ ID NO 68
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Thr Val Val Lys
                20                  25                  30

Ile Lys Tyr Glu Gly Thr Gly Ala Pro Cys Lys Val Pro Ile Glu Ile
            35                  40                  45

Arg Asp Val Asn Lys Glu Lys Val Val Gly Arg Ile Ile Ser Ser Thr
50                  55                  60

Pro Phe Ala Glu Asn Thr Asn Ser Val Thr Asn Ile Glu Leu Glu Pro
65                  70                  75                  80

Pro Phe Gly Asp Ser Tyr Ile Val Ile Gly Val Gly Asp Ser Ala Leu
                85                  90                  95

Thr Leu His Trp Phe Arg Lys Gly Ser Ser Ile Gly Lys
            100                 105

<210> SEQ ID NO 69
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Arg Ile Lys Gly Met Ser Tyr Thr Met Cys Ser Gly Lys Phe Ser
1               5                   10                  15

Ile Asp Arg Glu Met Ala Glu Thr Gln His Gly Thr Thr Val Val Lys
                20                  25                  30

Val Lys Tyr Glu Gly Thr Gly Ala Pro Cys Lys Val Pro Ile Glu Ile
            35                  40                  45

Arg Asp Val Asn Lys Glu Lys Val Val Gly Arg Ile Ile Ser Ser Thr
50                  55                  60

Pro Phe Ala Glu Ser Thr Asn Ser Val Thr Asn Ile Glu Leu Glu Pro
65                  70                  75                  80

Pro Phe Gly Asp Ser Tyr Ile Val Ile Gly Val Gly Asp Ser Ala Leu
                85                  90                  95

Thr Leu His Trp Phe Arg Lys Gly Ser Ser Ile Gly Lys
            100                 105

<210> SEQ ID NO 70
<211> LENGTH: 109
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 70

Met Arg Ile Lys Gly Met Ser Tyr Thr Met Cys Ser Gly Lys Phe Ser
1               5                   10                  15

Ile Asp Lys Glu Met Ala Glu Thr Gln His Gly Thr Val Val Lys
                20                  25                  30

Val Lys Tyr Glu Gly Ala Gly Ala Pro Cys Lys Val Pro Ile Glu Ile
            35                  40                  45

Arg Asp Val Asn Lys Glu Lys Val Val Gly Arg Ile Ile Ser Ser Thr
    50                  55                  60

Pro Phe Ala Glu Tyr Thr Asn Ser Val Thr Asn Ile Glu Leu Glu Pro
65                  70                  75                  80

Pro Phe Gly Asp Ser Tyr Ile Val Ile Gly Val Gly Asp Ser Ala Leu
                85                  90                  95

Thr Leu His Trp Phe Arg Lys Gly Ser Ser Ile Gly Lys
                100                 105

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

```
Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Tyr Met Asp Val Trp Gly Lys Gly Thr Thr Val Thr Val Ser
            100                 105                 110

Ser

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Tyr Met Asp Val Trp Gly Gln Gly Thr Leu Val Thr Val Ser
            100                 105                 110

Ser

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
             35                  40                  45

Gly Arg Ile Asp Pro Ser Asp Ser Tyr Thr Asn Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Met Asp Val Trp Gly Gln Gly Thr Leu Val Thr Val Ser
```

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Cys
                85                  90                  95

Thr Phe Gly Gln Gly Thr Lys Leu Glu Ile Lys
            100                 105

<210> SEQ ID NO 77
<211> LENGTH: 103
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Gly Gly
                85                  90                  95

Gly Thr Lys Val Glu Ile Lys
            100

<210> SEQ ID NO 78
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Phe Gly Gln Gly Thr Lys Leu Glu Ile Lys
            100                 105

<210> SEQ ID NO 79
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
50                  55                  60

Arg Phe Ser Gly Ser Gly Ser Gly Thr Asp Phe Thr Leu Thr Ile Asn

```
                65                  70                  75                  80
Pro Val Glu Ala Asn Asp Thr Ala Asn Tyr Tyr Cys Leu Gln Ser Lys
                    85                  90                  95

Asn Phe Pro Trp Thr Phe Gly Gln Gly Thr Lys Val Glu Ile Lys
                100                 105                 110
```

```
<210> SEQ ID NO 80
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Gly Phe Asn Ile Lys Asp Val Tyr
            20                  25                  30

Met Ser Trp Val Arg Gln Ala Pro Gly Gln Gly Leu Glu Trp Met Gly
        35                  40                  45

Arg Ile Asp Pro Glu Asn Gly Asp Thr Lys Tyr Asp Pro Lys Leu Gln
    50                  55                  60

Gly Arg Val Thr Met Thr Ala Asp Thr Ser Thr Asn Thr Ala Tyr Met
65                  70                  75                  80

Glu Leu Arg Ser Leu Arg Ser Asp Asp Thr Ala Val Tyr Tyr Cys Ala
                85                  90                  95

Arg Gly Trp Glu Gly Phe Ala Tyr Trp Gly Gln Gly Thr Leu Val Thr
            100                 105                 110

Val Ser Ser
        115
```

```
<210> SEQ ID NO 81
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Val
            20                  25                  30

Tyr Met Ser Trp Val Arg Gln Ala Pro Gly Gln Gly Leu Glu Trp Met
        35                  40                  45

Gly Arg Ile Asp Pro Glu Asn Gly Asp Thr Lys Tyr Asp Pro Lys Leu
    50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Trp Glu Gly Phe Ala Tyr Trp Gly Gln Gly Thr Leu Val
            100                 105                 110

Thr Val Ser Ser
        115
```

```
<210> SEQ ID NO 82
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caagtgcaac tcgttcagtc cggagcagaa gtcaagaaac ctggagcttc agtcaaagtc      60
agctgcaagg ccggcttcaa tatcaaggac gtctacatgt cctgggtgcg gcaggctcca     120
gggcaaggac tggaatggat ggggcgcatt gacccggaga cggtgatac gaagtacgac      180 ccgaaactgc agggccgcgt gaccatgacc gcagatacta gcaccaacac cgcgtacatg     240
gagctgcggt ccttgaggtc ggatgacact gctgtgtatt actgtgccag aggctgggaa     300
gggttcgcgt actggggaca gggaactctc gtgactgtgt cgtct                     345

<210> SEQ ID NO 83
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caagtgcaac tcgttcagtc cggagcagaa gtcaagaaac ctggagcttc agtcaaagtc      60
agctgcaagg cctcgggctt caatatcaag gacgtctaca tgtcctgggt gcggcaggct     120
ccagggcaag gactggaatg gatggggcgc attgacccgg agaacggtga tacgaagtac     180
gacccgaaac tgcagggccg cgtgaccatg accgcagata ctagcaccaa caccgcgtac     240
atggagctgc ggtccttgag gtcggatgac actgctgtgt attactgtgc cagaggctgg     300
gaagggttcg cgtactgggg acagggaact ctcgtgactg tgtcgtct                  348

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Val Arg Gln Ala Pro Gly Gln Gly Leu Glu Trp Met Gly
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Val Arg Gln Ala Pro Glu Gln Gly Leu Glu Trp Met Gly
1               5                   10

<210> SEQ ID NO 86
<211> LENGTH: 348
<212> TYPE: DNA
<213> ORGANISM: Artificial Sequence
<220> FEATURE:
```

<223> OTHER INFORMATION: Description of Artificial Sequence: Synthetic
     polynucleotide

<400> SEQUENCE: 86

```
caagtgcaac tcgttcagtc cggagcagaa gtcaagaaac ctggagcttc agtcaaagtc    60
agctgcaagg cctcgggctt caatatcaag gacacctaca tgtcctgggt gcggcaggct   120
ccagagcaag gactggaatg gatggggcgc attgacccgg agaacggtga tacgaagtac   180
gacccgaaac tgcagggccg cgtgaccatg accgcagata ctagcaccaa caccgcgtac   240
atggagctgc ggtccttgag gtcggatgac actgctgtgt attactgttc cagaggctgg   300
gaagggttcg cgtactgggg acagggaact ctcgtgactg tgtcgtct              348
```

<210> SEQ ID NO 87
<211> LENGTH: 348
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 87

```
caagtgcaac tcgttcagtc cggagcagaa gtcaagaaac ctggagcttc agtcaaagtc    60
agctgcaagg cctcggcctt caatatcaag gacgtctaca tgtcctgggt gcggcaggct   120
ccagagcaag gactggaatg gatggggcgc attgacccgg agaacggtga tacgaagtac   180
gacccgaaac tgcagggccg cgtgaccatg accgcagata ctagcaccaa caccgcgtac   240
atggagctgc ggtccttgag gtcggatgac actgctgtgt attactgtgc cagaggctgg   300
gaagggttcg cgtactgggg acagggaact ctcgtgactg tgtcgtct              348
```

<210> SEQ ID NO 88
<211> LENGTH: 348
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 88

```
caagtgcaac tcgttcagtc cggagcagaa gtcaagaaac ctggagcttc agtcaaagtc    60
agctgcaagg cctcgggctt caatatcaag gacgtctaca tgtcctgggt gcggcaggct   120
ccagagcaag gactggaatg gatggggcgc attgacccgg agaacggtga tacgaagtac   180
gacccgaaac tgcagggccg cgtgaccatg accgcagata ctagcaccaa caccgcgtac   240
atggagctgc ggtccttgag gtcggatgac actgctgtgt attactgtag cagaggctgg   300
gaagggttcg cgtactgggg acagggaact ctcgtgactg tgtcgtct              348
```

<210> SEQ ID NO 89
<211> LENGTH: 348
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 89

```
caagtgcaac tcgttcagtc cggagcagaa gtcaagaaac ctggagcttc agtcaaagtc    60
agctgcaagg cctcgggctt caatatcaag gacgtctaca tgtcctgggt gcggcaggct   120
ccagagcaag gactggaatg gatggggcgc attgacccgg agaacggtga tacgaagtac   180
```

```
gacccgaaac tgcagggccg cgtgaccatg accgcagata ctagcaccaa caccgcgtac    240
atggagctgc ggtccttgag gtcggatgac actgctgtgt attactgtgc cagaggctgg    300
gaagggttcg cgtactgggg acagggaact ctcgtgactg tgtcgtct                 348
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Trp Glu Gly Phe Ile Tyr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Trp Glu Gly Phe Lys Tyr
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Trp Glu Gly Phe Asp Tyr
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Trp Glu Gly Phe Glu Tyr
1               5

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ala Ser Glu Asn Val Asp Lys Phe Gly Asn Ser Phe Met His
1               5                   10                  15

<210> SEQ ID NO 95

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Leu Gln Leu Val Gln Ser Gly
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Val Gln Leu Val Glu Gln Ser Gly
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Val Lys Leu Val Glu Gln Ser Gly
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Val Lys Leu Leu Glu Gln Ser Gly
1               5
```

ANTIBODY MOLECULES TO DENGUE VIRUS AND USES THEREOF

CROSS REFERENCE TO RELATED APPLICATIONS

This application is a divisional of U.S. application Ser. No. 15/155,620, filed on May 16, 2016, now U.S. Pat. No. 10,155,806, issued on Dec. 18, 2018, which is a divisional of U.S. application Ser. No. 14/921,701, filed on Oct. 23, 2015, now U.S. Pat. No. 9,365,639, issued on Jun. 14, 2016, which is a divisional of U.S. application Ser. No. 14/600, 306, filed on Jan. 20, 2015, now U.S. Pat. No. 9,212,217, issued on Dec. 15, 2015, which claims priority to U.S. Provisional Application No. 61/938,646, filed on Feb. 11, 2014, U.S. Provisional Application No. 62/017,970, filed on Jun. 27, 2014, and U.S. Provisional Application No. 62/046, 379, filed on Sep. 5, 2014. The disclosures of the prior applications are considered part of (and are incorporated by reference in their entirety in) the disclosure of this application.

SEQUENCE LISTING

The instant application contains a Sequence Listing which has been submitted electronically in ASCII format and is hereby incorporated by reference in its entirety. Said ASCII copy, created on Jan. 7, 2015, is named P2029-700210_SL.txt and is 73,010 bytes in size.

BACKGROUND

Dengue virus is a positive-sense RNA virus belonging to the Flavivirus genus of the family Flaviviridae. Dengue virus is widely distributed throughout the tropical and semi-tropical regions of the world and is transmitted to humans by mosquito vectors. Dengue virus is a leading cause of hospitalization and death in children in at least eight tropical Asian countries (WHO, 1997. Dengue haemorrhagic fever: diagnosis, treatment prevention and control—2nd ed. Geneva: WHO). There are four serotypes of dengue virus (DV-1, DV-2, DV-3, and DV-4) which annually cause an estimated 50-100 million cases of dengue fever and 500,000 cases of the more severe form of dengue virus infection, dengue hemorrhagic fever/dengue shock syndrome (DHF/DSS) (Gubler, D. J. & Meltzer, M. 1999 *Adv Virus Res* 53:35-70). DHF/DSS is seen predominately in children and adults experiencing a second dengue virus infection with a serotype different than that of their first dengue virus infection and in primary infection of infants who still have circulating dengue-specific maternal antibody (Burke, D. S. et al. 1988 *Am J Trop Med Hyg* 38:172-80; Halstead, S. B. et al. 1969 *Am J Trop Med Hyg* 18:997-1021; Thein, S. et al. 1997 *Am J Trop Med Hyg* 56:566-72).

The different serotypes of dengue virus differ at the amino acid level by about 25-40% and have antigenic differences, and this variation has hindered efforts to produce a therapy effective against all serotypes.

All four dengue virus serotypes display an E (envelope) protein on the viral surface. The E protein contributes to the attachment of the virus to a host cell. The E protein comprises a DI domain (a nine-stranded beta-barrel) a DII domain (a domain implicated in fusion with the host cell), and a DIII domain (an immunoglobulin-like domain). The humoral response to E protein in humans generally targets the DI and DII regions, with much of the antibodies exhibiting high cross-serotype reactivity but low neutralization activity.

There is a need in the art for new prophylactic and therapeutic treatments for dengue virus, and especially for treatments that are effective against all four serotypes of the virus.

SUMMARY

This disclosure provides, at least in part, antibody molecules that bind to the dengue virus, for example, the dengue virus E protein, and which comprise functional and structural properties disclosed herein. In some embodiments, the antibody molecules bind to the "A" beta-strand of EDIII (the E protein DIII domain). In some embodiments, the antibody molecules bind to and/or neutralize at least 1, 2, 3, or 4 dengue virus serotypes, e.g., DV-1, DV-2, DV-3, and DV-4. In some embodiments, the antibody molecule is selected from Table 1. In some embodiments, the antibody molecules comprise a deletion of VH S26 and/or a VH T33V substitution compared to antibody A11. These mutations, in some embodiments, may improve one or more properties, e.g., improve antibody affinity for one or more dengue virus serotypes, for example serotype DV-4. In some embodiments, the antibody molecule targets a site on EDIII that is conserved across all four dengue serotypes. Nucleic acid molecules encoding the antibody molecules, expression vectors, host cells, pharmaceutical compositions, and methods for making the antibody molecules are also provided. The anti-dengue antibody molecules disclosed herein can be used (alone or in combination with other agents or therapeutic modalities) to treat, prevent and/or diagnose dengue virus, e.g., DV-1, DV-2, DV-3, or DV-4.

Accordingly, in certain aspects, this disclosure provides an antibody molecule (e.g., an isolated, recombinant, or humanized antibody molecule) having one or more (e.g., 1, 2, 3, 4, 5, 6, 7, 8, 9, 10, 11, 12, 13, 14, 15, 16, 17, 18, 19, 20, 21, 22, 23, or all) of the following properties from List 1:

a) Binds to EDIII (e.g., one or more EDIII from any dengue virus serotype, e.g., from DV-1, DV-2, DV-3, or DV-4, e.g., all four EDIII from DV-1, DV-2, DV-3, or DV-4) with high affinity, e.g., with a dissociation constant ($K_D$) of less than about 100 nM, typically about 10 nM, and more typically, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM, b) Binds to DV-4 EDIII with high affinity, e.g., with a dissociation constant ($K_D$) of less than about 100 nM, e.g., about 10 nM, e.g., about 10-1 nM or stronger, e.g., less than about 10, 8, 6, 5, 4, or 3 nM, c) Binds to DV-4 and/or DV-3 EDIII domain with a greater affinity than antibody A11 (also referred to as 4E5A herein) and/or antibody 4E11, e.g., at least 2, 3, 4, 5, 6, 8, 10, 12, 15, 100, 1,000, 5,000, or 10,000-fold greater affinity, d) Neutralizes dengue virus (e.g., one or more of DV-1, DV-2, DV-3, and DV-4, e.g., all of DV-1, DV-2, DV-3, and DV-4), e.g., in a focus reduction neutralization test or a related test for evaluating neutralization of viral activity, e) Neutralizes DV-4 with an improved IC50 compared to antibody A11 and/or antibody 4E11, e.g., at least 2, 3, 4, 5, 6, 8, 10, 12, 25, 50, 75, 100, or 1,000-fold improved IC50, e.g., in a focus reduction neutralization test or a related test for evaluating neutralization of viral activity, f) Has a mutation (e.g., one or more of a deletion, an insertion, a substitution, e.g., a conservative substitution) at one or more positions relative to A11, e.g., in the VH and/or VL, e.g., in one or more CDRs or framework regions, g) Has a mutation (e.g., one or more of a deletion, an insertion, a substitution, e.g., a conservative substitution), e.g., a substitution, e.g., a T33V substitution, in the heavy chain CDR1 region relative to A11, h) Has a mutation (e.g., one or more of a deletion, an insertion, a substitution, e.g., a conservative substitution), e.g., a deletion, at position 26 in the heavy chain FW1 relative to A11, i) Has both a mutation (e.g., one or more of a deletion, an insertion, a substitution, e.g., a conservative substitution), e.g., a substitution, e.g., a T33V mutation in the heavy chain CDR1 region relative to A11 and a mutation (e.g., one or more of a deletion, an insertion, a substitution, e.g., a conservative substitution), e.g., a deletion, at position 26 in the heavy chain FW1 relative to A11, j) Has a mutation (e.g., one or more of a deletion, an insertion, a substitution, e.g., a conservative substitution), e.g., a substitution, e.g., a T33V mutation in the heavy chain CDR1 region relative to A11, and has improved (e.g., relative to A11) binding to and/or neutralization of dengue virus, e.g., to one or more (e.g., all) of DV-1, DV-2, DV-3, and DV-4, k) Has a mutation (e.g., one or more of a deletion, an insertion, a substitution, e.g., a conservative substitution), e.g., a deletion, at position 26 in the heavy chain FW1 relative to A11, and has improved (e.g., relative to A11) binding to and/or neutralization of dengue virus, e.g., to one or more (e.g., all) of DV-1, DV-2, DV-3, and DV-4, e.g., to DV-4, l) Has both a mutation (e.g., one or more of a deletion, an insertion, a substitution, e.g., a conservative substitution), e.g., a substitution, e.g., a T33V mutation in the heavy chain CDR1 region relative to A11 and a mutation (e.g., one or more of a deletion, an insertion, a substitution, e.g., a conservative substitution), e.g., a deletion, at position 26 in the heavy chain FW1 relative to A11, and has improved (e.g., relative to A11) binding to and/or neutralization of dengue virus, e.g., to one or more (e.g., all) of DV-1, DV-2, DV-3, and DV-4, e.g., to DV-4, m) Displays improved binding to EDIII of one or more (e.g., all) of the dengue virus strains listed in FIGS. 10A-10B, 11 and 19-21, e.g., one or more DV-2 strains, one or more DV-3 strains, one or more DV-4 strains, e.g., one or more of: DENV-4 BC2, DENV-4-Sing10, DENV-4 NewCa109, DENV-4 Phil56, DENV-3 Sing09, DENV-3 Nic10, DENV-3 H87, DENV-2 Peru95, DENV-2 Sing08, DENV-2 NGC, DENV-1 Hawaii/1944, DENV-2 New Guinea/1944 (NGC), DENV-3 Philippines/1956 (H87), DENV-4 Mexico/1997 (BC287/97), and DENV-4 H241, e.g., with at least 2, 3, 4, 5, 6, 8, 10, 12, 25, 50, 75, 100, or 1,000-fold greater affinity, n) Disrupts the native structure of the E protein on the surface of the virion, e.g., which may cause inactivation of the virus, o) Binds specifically to an epitope on EDIII, e.g., the same or similar epitope as the epitope recognized by a A11 or B11 monoclonal antibody, p) Shows the same or similar binding affinity or specificity, or both, as an antibody of Table 1, e.g., D88, A48, F38, F108, or C88, q) Shows the same or similar binding affinity or specificity, or both, as an antibody molecule (e.g., a heavy chain variable region and light chain variable region) described in Table 1, e.g., D88, A48, F38, F108, or C88, r) Shows the same or similar binding affinity or specificity, or both, as an antibody molecule (e.g., a heavy chain variable region and light chain variable region) comprising an amino acid sequence shown in Table 2, s) Inhibits, e.g., competitively inhibits, the binding of a second antibody molecule to EDIII wherein the second antibody molecule is an antibody molecule described herein, e.g., an antibody molecule chosen from Table 1, e.g., D88, A48, F38, F108, or C88, t) Binds the same or an overlapping epitope with a second antibody molecule to EDIII, wherein the second antibody molecule is an antibody molecule described herein, e.g., an antibody molecule chosen from Table 1, e.g., D88, A48, F38, F108, or C88, u) Competes for binding and binds the same epitope, with a second antibody molecule to EDIII, wherein the second antibody molecule is an antibody molecule described herein, e.g., an antibody molecule chosen from Table 1, e.g., D88, A48, F38, F108, or C88, v) Has one or more biological properties of an antibody molecule described herein, e.g., an antibody molecule chosen from Table 1, e.g., D88, A48, F38, F108, or C88, w) Has one or more pharmacokinetic properties of an antibody molecule described herein, e.g., an antibody molecule chosen from Table 1, e.g., D88, A48, F38, F108, or C88, or x) Inhibits one of more activities of dengue virus, e.g., neutralizes the virus (for instance, measured in a focus reduction neutralization test or a related test for evaluating neutralization of viral activity).

In some embodiments, the antibody molecule has a mutation (e.g., one or more of a deletion, an insertion, a substitution, e.g., a conservative substitution), e.g., a T33V mutation in the heavy chain CDR1 region relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x). In certain embodiments, the antibody molecule has a mutation (e.g., one or more of a deletion, an insertion, a substitution, e.g., a conservative substitution), e.g., a deletion, at position 26 in the heavy chain FW1 relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x). In some embodiments, the antibody molecule has both a mutation (e.g., one or more of a deletion, an insertion, a substitution, e.g., a conservative substitution), e.g., a T33V mutation in the heavy chain CDR1 region relative to A11 and a mutation (e.g., one or more of a deletion, an insertion, a substitution, e.g., a conservative substitution), e.g., a deletion, at position 26 in the heavy chain FW1 relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the antibody molecule has a T33V mutation in the heavy chain CDR1 region relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x). In certain embodiments, the antibody molecule has a deletion at position 26 in the heavy chain FW1 relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x). In some embodiments, the antibody molecule has both a T33V mutation in the heavy chain CDR1 region relative to A11 and a deletion at position 26 in the heavy chain FW1 relative to A11, in combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the antibody molecule has both a T33V mutation in the heavy chain CDR1 region relative to A11 and a deletion, at position 26 in the heavy chain FW1 relative to A11, combination with one or more functional properties of List 1 above, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), (x). For example, the antibody molecule may bind EDIII (e.g., of DV-1, DV-2, DV-3, or DV-4) with high affinity, e.g., with a dissociation constant ($K_D$) of less than about 100 nM, typically about 10 nM, and more typically, about 10-0.01 nM, about 5-0.01 nM, about 3-0.05 nM, or about 1-0.1 nM, or stronger, e.g., less than about 80, 70, 60, 50, 40, 30, 20, 10, 8, 6, 4, 3, 2, 1, 0.5, 0.2, 0.1, 0.05, or 0.01 nM. As a further example, the antibody molecule may bind to DV-4 EDIII with high affinity, e.g., with a dissociation constant ($K_D$) of less than about 100 nM, e.g., about 10 nM, e.g., about 10-1 nM or stronger, e.g., less than about 10, 8, 6, 5, 4, or 3 nM. Furthermore, the antibody molecule may neutralize DV-4 with an improved IC50 compared to antibody A11 and/or antibody 4E11, e.g., at least 2, 3, 4, 5, 6, 8, 10, 12, 100, 1,000-fold improved IC50, e.g., in a focus reduction neutralization test or a related test for evaluating neutralization of viral activity.

In certain embodiments, affinity is measured by competition ELISA or SPR. In some embodiments, affinity is measured by one or more of BIAcore, ELISA, or flow cytometry.

In certain embodiments, the anti-dengue antibody molecule is a humanized antibody molecule and has one or more properties from List 1 above, e.g., one or more (e.g., 1, 2, 3, 4, 5, 6, 7, 8, 9, 10, 11, 12, 13, 14, 15, 16, or all) of properties (a), (b), (c), (d), (e), (m), (n), (o), (p), (q), (r), (s), (t), (u), (v), (w), or (x).

In some embodiments, the antibody molecule binds to EDIII with high affinity, e.g., with a $K_D$ that is at least about 10%, 20%, 30%, 40%, 50%, 60%, 70%, 80% or 90% lower than the $K_D$ of a murine anti-dengue antibody molecule, e.g., 4E11, A11 or B11.

In some embodiments, the expression level of the antibody molecule is higher, e.g., at least about 0.5, 1, 2, 3, 4, 5, 6, 7, 8, 9 or 10-fold higher, than the expression level of a murine antibody molecule, e.g., a murine anti-dengue antibody molecule described herein. In some embodiments, the antibody molecule is expressed in mammalian cells, e.g., human or rodent cells.

In some embodiments, the antibody molecule reduces one or more dengue virus activities with an IC50 (concentration at 50% inhibition) that is lower, e.g., at least about 10%, 20%, 30%, 40%, 50%, 60%, 70%, 80% or 90% lower, than the IC50 of a murine anti-dengue antibody molecule, e.g., a murine anti-dengue antibody molecule described herein. In some embodiments, the dengue virus activity is neutralized, e.g., in the focus reduction neutralization test described in Tharakaramana et al., *Proc Natl Acad Sci USA*. 2013 Apr. 23; 110(17):E1555-64. doi: 10.1073/pnas.1303645110. Epub 2013 Apr. 8, which is hereby expressly incorporated by reference in its entirety, including all supplemental materials. Other related tests that can be used to evaluate neutralization of viral activity include, e.g., enzyme-linked immunosorbent assay (ELISA)-based microneutralization (MN) assays (e.g., as described in Vorndam et al., *Am J Trop Med Hyg* 2002; 66: 208-212) and fluorescent antibody cell sorter-based, DC-SIGN expresser dendritic cell (DC) assay (e.g., as described in Martin et al., *J Virol Methods* 2006; 134: 74-85).

In certain embodiments, the antibody molecule reduces transmission of dengue virus (e.g., reduces transmission between a subject (e.g., a human) and a mosquito), e.g., by at least about 10%, 20%, 30%, 40%, 50%, 60%, 70%, 80%, or 90%, e.g., as measured by a mosquito model described herein.

In other embodiments, the antibody molecule has an improved ability to reduce transmission of dengue virus (e.g., has an improved ability to reduce transmission of dengue virus between a subject (e.g., a human) and a mosquito), e.g., by at least about 0.5, 1, 2, 3, 4, 5, 6, 7, 8, 9 or 10-fold higher than a murine anti-dengue antibody molecule, e.g., a murine anti-dengue antibody molecule described herein, e.g., 4E11, A11 or B11, e.g., as measured by a mosquito model described herein.

In other embodiments, the antibody molecule reduces the mosquito viral load (e.g., the amount of virus, and/or infectivity, carried by a mosquito), e.g., by at least about 10%, 20%, 30%, 40%, 50%, 60%, 70%, 80%, or 90%, e.g., as measured by a mosquito model described herein.

In some embodiments, the antibody molecule has improved stability, e.g., at least about 0.5, 1, 2, 3, 4, 5, 6, 7, 8, 9 or 10-fold more stable in vivo or in vitro, than a murine anti-dengue antibody molecule, e.g., a murine anti-dengue antibody molecule described herein, e.g., 4E11, A11 or B11.

In some embodiments, the anti-dengue antibody molecule comprises at least one antigen-binding region, e.g., a variable region or an antigen-binding fragment thereof, from an antibody described herein, e.g., an antibody chosen from Table 1, e.g., D88, A48, F38, F108, or C88, or a sequence substantially identical to any of the aforesaid sequences (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule comprises at least one, two, three, or four variable regions from an antibody described herein, e.g., an antibody of Table 1, e.g., D88, A48, F38, F108, or C88, or a sequence substantially identical to any of the aforesaid sequences (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule comprises at least one or two heavy chain variable regions from an antibody described herein, e.g., an antibody of Table 1, e.g., D88, A48, F38, F108, or C88, or a sequence substantially identical to any of the aforesaid sequences (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule comprises at least one or two light chain variable regions from an antibody described herein, e.g., an antibody of Table 1, e.g., D88, A48, F38, F108, or C88 or a sequence substantially identical to any of the aforesaid sequences (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule comprises a valine at position 33 (e.g., a T33V mutation) in the VH region, e.g., relative to 4E5A and/or 4E11 or an antibody of Table 1. In some embodiments, the anti-dengue antibody comprises a del26 (deletion at position 26) in the VH region, e.g., relative to 4E5A or an antibody of Table 1. In some embodiments, the anti-dengue antibody comprises both a valine at position 33 (e.g., a T33V mutation) and a del26 mutation in the VH region, e.g., relative to 4E5A or an antibody of Table 1. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule comprises at least one, two, or three complementarity determining regions (CDRs) from a heavy chain variable region of an antibody described herein, e.g., an antibody of Table 1, e.g., D88, A48, F38, F108, or C88, or a sequence substantially identical to any of the aforesaid sequences (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule includes at least one, two, or three CDRs (or collectively all of the CDRs) from a heavy chain variable region comprising an amino acid sequence shown in Table 3. In some embodiments, one or more of the CDRs (or collectively all of the CDRs) have one, two, three, four, five, six or more changes, e.g., amino acid substitutions, insertions, or deletions, relative to the CDRs shown in Table 3. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, or three CDRs (or collectively all of the CDRs) from a light chain variable region comprising an amino acid sequence shown in Table 3. In some embodiments, one or more of the CDRs (or collectively all of the CDRs) have one, two, three, four, five, six or more changes, e.g., amino acid substitutions, insertions, or deletions, relative to the CDRs shown in Table 3. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, three, four, five or six CDRs (or collectively all of the CDRs) from a heavy and light chain variable region comprising an amino acid sequence shown in Table 3. In some embodiments, one or more of the CDRs (or collectively all of the CDRs) have one, two, three, four, five, six or more changes, e.g., amino acid substitutions, insertions, or deletions, relative to the CDRs shown in Table 3. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule includes all six CDRs from an antibody described herein, e.g., an antibody of Table 1, e.g., D88, A48, F38, F108, or C88, or closely related CDRs, e.g., CDRs which are identical or which have at least one amino acid alteration, but not more than two, three or four alterations (e.g., substitutions e.g., conservative substitutions, deletions, or insertions). In certain embodiments, the anti-dengue antibody molecule may include any CDR described herein. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, or three Chothia hypervariable loops from a heavy chain variable region of an antibody described herein, e.g., an antibody of Table 1, e.g., D88, A48, F38, F108, or C88, or at least the amino acids from those hypervariable loops that contact EDIII. For instance, in some embodiments, an antibody molecule provided herein has a VHCDR1 of SEQ ID NO: 9, a VHCDR2 of SEQ ID NO: 10, and a VHCDR3 of SEQ ID NO: 5. An antibody molecule provided herein may also have a VHCDR1 of SEQ ID NO: 15, a VHCDR2 of SEQ ID NO: 10, and a VHCDR3 of SEQ ID NO: 5. An antibody molecule provided herein may also have a VHCDR1 of SEQ ID NO: 22, 24, 26, 28, or 30; a VHCDR2 of SEQ ID NO: 10; and a VHCDR3 of SEQ ID NO: 5. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, and optionally in combination with heavy chain CDRs described herein, the anti-dengue antibody molecule includes at least one, two, or three Chothia hypervariable loops from a light chain variable region of an antibody described herein, e.g., an antibody of Table 1, e.g., D88, A48, F38, F108, or C88, or at least the amino acids from those hypervariable loops that contact EDIII. For instance, in certain embodiments, an antibody molecule provided herein has a VHCDR1 of SEQ ID NO: 6, a VHCDR2 of SEQ ID NO: 7, and a VHCDR3 of SEQ ID NO: 8. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, or three Kabat hypervariable loops from a heavy chain variable region of an antibody described herein, e.g., an antibody of Table 1, e.g., D88, A48, F38, F108, or C88, or at least the amino acids from those hypervariable loops that contact EDIII. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, or three Kabat hypervariable loops from a light chain variable region of an antibody described herein, e.g., an antibody of Table 1, e.g., D88, A48, F38, F108, or C88, or at least the amino acids from those hypervariable loops that contact EDIII. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule includes at least one, two, three, four, five, or six hypervariable loops from the heavy and light chain variable regions of an antibody described herein, e.g., an antibody of Table 1, e.g., D88, A48, F38, F108, or C88, or at least the amino acids from those hypervariable loops that contact EDIII. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule includes all six hypervariable loops from the heavy and light chain variable regions of an antibody described herein, e.g., an antibody of Table 1, e.g., D88, A48, F38, F108, or C88, or at least the amino acids from those hypervariable loops that contact EDIII, or closely related hypervariable loops, e.g., hypervariable loops which are identical or which have at least one amino acid alteration, but not more than two, three or four alterations (e.g., substitutions, e.g., conservative substitutions, deletions, or insertions). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule includes at least one, two, or three hypervariable loops that have the same canonical structures as the corresponding hypervariable loop of an antibody described herein, e.g., an antibody of Table 1, e.g., D88, A48, F38, F108, or C88, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these publications. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule comprises at least one, two, or three (e.g., all) CDRs from a heavy chain variable region having an amino acid sequence as set forth in Table 3, or a sequence substantially identical thereto (e.g., a sequence at least about 85%, 90%, 95%, 99% or more identical thereto, and/or having one, two, three or more substitutions, insertions or deletions, e.g., conserved substitutions). In some embodiments, the anti-dengue antibody molecule comprises at least one, two, or three (e.g., all) CDRs from a light chain variable region having an amino acid sequence as set forth in Table 3, or a sequence substantially identical thereto (e.g., a sequence at least about 85%, 90%, 95%, 99% or more identical thereto, and/or having one, two, three or more substitutions, insertions or deletions, e.g., conserved substitutions). In certain embodiments, the anti-dengue antibody molecule comprises at least one, two, three, four, five or six (e.g., all) CDRs from heavy and light chain variable regions having an amino acid sequence as set forth in Table 3, or a sequence substantially identical thereto (e.g., a sequence at least about 85%, 90%, 95%, 99% or more identical thereto, and/or having one, two, three or more substitutions, insertions or deletions, e.g., conserved substitutions). In some embodiments, an antibody molecule has a structural feature discussed in this paragraph and one or more advantageous properties such as an improved affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the anti-dengue antibody molecule comprises at least one, two, or three (e.g., all) CDRs from a heavy chain variable region having an amino acid sequence of an antibody described herein, e.g., an antibody of Table 1, e.g., D88, A48, F38, F108, or C88, or a sequence substantially identical thereto (e.g., a sequence at least about 85%, 90%, 95%, 99% or more identical thereto, and/or having one, two, three or more substitutions, insertions or deletions, e.g., conserved substitutions). In certain embodiments, the anti-dengue antibody molecule comprises at least one, two, or three (e.g., all) CDRs from a light chain variable region having an amino acid sequence of an antibody described herein, e.g., an antibody of Table 1, e.g., D88, A48, F38, F108, or C88, or a sequence substantially identical thereto (e.g., a sequence at least about 85%, 90%, 95%, 99% or more identical thereto, and/or having one, two, three or more substitutions, insertions or deletions, e.g., conserved substitutions). In some embodiments, the anti-dengue antibody molecule comprises six CDRs described herein, e.g., in a VL and VH sequence of Table 2. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In aspects embodiments, the antibody molecule has a VHCDR1, VHCDR2, VHCDR3, VLCDR1, VLCDR2, and VLCDR3 selected from Table 3. The six CDRs may all be Kabat-defined, all Chothia-defined, or some Kabat- and some Chothia-defined. For instance, VHCDR1 may be selected from SEQ ID NO: 3, 9, 14, 15, 22, 24, 26, 28, or 30; VHCDR2 may be selected from SEQ ID NO: 4, 10, or 35; VHCDR3 may be SEQ ID NO: 5; VLCDR1 may be SEQ ID NO: 6; VLCDR2 may be SEQ ID NO: 7; and VLCDR3 may be SEQ ID NO: 8.

In certain embodiments, the light or the heavy chain variable framework of the anti-dengue antibody can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In some embodiments, the light or heavy chain variable framework region includes a light or heavy chain variable framework sequence at least 70, 75, 80, 85, 87, 88, 90, 92, 94, 95, 96, 97, 98, 99% identical or identical to the frameworks of a VH or VL segment of a human germline gene. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the VH region (e.g., the framework regions therein) of the anti-dengue antibody comprises one or more positions from a human VH region, e.g., human heavy chain germline-encoded amino acid sequences, e.g., positions found in one or more (e.g., all) of FW1, FW2, FW3, and FW4. In certain embodiments, optionally in combination with the VH residues discussed in the previous sentence, the VL region (e.g., the framework regions therein) of the anti-dengue antibody comprises one or more positions from a human VL region, e.g., human heavy chain germline-encoded amino acid sequences, e.g., positions found in one or more (e.g., two, three, four, five, or all) of FW1, FW2, FW3, and FW4.

For example, in some embodiments, the antibody molecule comprises one or more (e.g., at least 2, 3, 4, 5, 6, 7, 8, 9, 10, 15, 20, 25, 30, or all) residues according to heavy chain or light chain FW1, FW2, FW3, or FW4 regions from a human germline sequence of Table 5. More specifically, in some embodiments the antibody molecule has one or more (e.g., at least 2, 3, 4, 5, 10, or 15, or all) VH FW1 residues of a VH germline sequence of Table 6; in some embodiments the antibody molecule has one or more (e.g., at least 2, 3, 4, 5, 10, or 15, or all) VH FW2 residues of a VH germline sequence of Table 6; in some embodiments the antibody molecule has one or more (e.g., at least 2, 3, 4, 5, 10, or 15, or all) VH FW3 residues of a VH germline sequence of Table 6, and in some embodiments the antibody molecule has one or more (e.g., at least 2, 3, 4, 5, 10, or 15, or all) VH FW4 residues of a VH germline sequence of Table 6. Furthermore, and optionally in combination with the heavy chain residues discussed in the previous sentence, in some embodiments the antibody molecule has one or more (e.g., at least 2, 3, 4, 5, 10, or 15, or all) VL FW1 residues of a VL germline sequence of Table 6; in some embodiments the antibody molecule has one or more (e.g., at least 2, 3, 4, 5, 10, or 15, or all) VL FW2 residues of a VL germline sequence of Table 6; in some embodiments the antibody molecule has one or more (e.g., at least 2, 3, 4, 5, 10, or 15, or all) VL FW3 residues of a VL germline sequence of Table 6, and in some embodiments the antibody molecule has one or more (e.g., at least 2, 3, 4, 5, 10, or 15, or all) VL FW4 residues of a VL germline sequence of Table 6. In certain embodiments, the antibody molecule has a heavy chain framework VH1-18*01, JH4*01 and/or light chain framework Vk4-1*01, Jk2*02.

In certain embodiments, the anti-dengue antibody molecule comprises a heavy chain variable domain having at least one, two, three, four, five, six, seven, ten, fifteen, twenty or more changes, e.g., amino acid substitutions, insertions, or deletions, from an amino acid sequence of Table 1, e.g., B11, D88, A48, F38, F108, or C88, e.g., the amino acid sequence of the FR region in the entire variable region. In some embodiments, the anti-dengue antibody molecule comprises a heavy chain variable domain having one or more (e.g., at least 5, 10, 15, or 20, or all) of: Q at position 3, V at position 5, a deletion of E at position 6, V at position 12, K at position 13, K at position 20, V at position 21, K at position 24, a deletion of S at position 26, V at position 33, R at position 39, A at position 41, G at position 43, M at position 49, L at position 65, R at position 68, V at position 69, M at position 71, T at position 77, M at position 82, E at position 83, R at position 85, R at position 88, D at position 90, A or V or S at position 98, and S at position 117 of the amino acid sequence of an antibody of Table 1, e.g., A11. Examples of antibodies having one or more (e.g., all) of these mutations include A48, B48, C88, F38, F108, and D48. In some embodiments, the humanized heavy chain contains one or more of: Q at position 3, V at position 5, a deletion of E at position 6, V at position 12, K at position 13, K at position 20, V at position 21, K at position 24, R at position 39, A at position 41, G at position 43, M at position 49, L at position 65, R at position 68, V at position 69, M at position 71, T at position 77, M at position 82, E at position 83, R at position 85, R at position 88, D at position 90, V or A or S at position 98, and S at position 117 of the amino acid sequence of an antibody of Table 1, e.g., A11. An example of an antibody having one or more (e.g., all) of these mutations is A68. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments (and optionally in combination with the heavy chain substitutions described herein, e.g., in the previous paragraph), the anti-dengue antibody molecule comprises a light chain variable domain having at least one, two, three, four, five, six, seven, ten, fifteen, twenty or more amino acid changes, e.g., amino acid substitutions, insertions, or deletions, from an amino acid sequence of Table 1, e.g., B11, D88, A48, F38, F108, or C88, e.g., the amino acid sequence of the FR region in the entire variable region. In certain embodiments, the anti-dengue antibody comprises a light chain variable domain having one or more (e.g., at least 5, 10, 15, or all) of: D at position 1, I at position 2, S at position 7, E at position 17, P at position 44, V at position 62, D at position 64, G at position 72, S at position 80, S at position 81, L at position 82, Q at position 83, E at position 85, V at position 89, Y at position 91, and Q at position 104 of the amino acid sequence of an antibody of Table 1, e.g., B11, D88, A48, F38, F108, or C88. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In some embodiments, the heavy or light chain variable domain, or both, of the of the anti-dengue antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody of Table 1, e.g., D88, A48, F38, F108, or C88, or which differs by at least 1, 2, 3, 4, or 5 residues, but less than 40, 30, 20, or 10 residues, from a variable region of an antibody described herein. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the heavy or light chain variable region, or both, of the anti-dengue antibody molecule includes an amino acid sequence encoded by a nucleic acid sequence described herein, or a nucleic acid that hybridizes to a nucleic acid sequence that encodes an antibody of Table 1, e.g., D88, A48, F38, F108, or C88, or its complement, e.g., under low stringency, medium stringency, or high stringency, or other hybridization condition described herein. This application also discloses the heavy or light chain variable region, or both, of the anti-dengue antibody molecule includes an amino acid sequence encoded by a nucleic acid sequence of Table 4, or its complement, e.g., under low stringency, medium stringency, or high stringency, or other hybridization condition described herein. In some embodiments, the nucleic acid is at least 80%, 85%, 90%, 92%, 95%, 97%, 98%, 99% or higher identical to a sequence of Table 4 or a portion thereof. In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain embodiments, the anti-dengue antibody molecule comprises at least one, two, three, or four antigen-binding regions, e.g., variable regions, having an amino acid sequence as set forth in Table 2, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 2). In certain embodiments, the anti-dengue antibody molecule includes a VH and/or VL domain encoded by a nucleic acid having a nucleotide sequence that encodes an antibody of Table 1, e.g., D88, A48, F38, F108, or C88, or a sequence substantially identical to any one of the nucleotide sequences (e.g., a sequence at least about 85%, 90%, 95%, 99% or more identical thereto, or which differs by no more than 3, 6, 15, 30, or 45 nucleotides from any one of the nucleotide sequences). In some embodiments, an antibody molecule has a structural feature discussed in this paragraph and one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain aspects, the present disclosure provides an antibody molecule, optionally capable of binding dengue virus, comprising:

(a) a heavy chain immunoglobulin variable region segment comprising:

a CDR1 comprising the sequence DVYMS (SEQ ID NO: 3) (or a sequence that differs by no more than, 1, 2, or 3 amino acids therefrom, optionally provided that V is unchanged), a CDR2 comprising the sequence RIDPENGDTKYDPK LQG (SEQ ID NO: 4) (or a sequence that differs by no more than, 1, 2, 3, 4, or 5 amino acids therefrom, optionally provided that L is unchanged), and a CDR3 comprising the sequence GWEGFAY (SEQ ID NO: 5) (or a sequence that differs by no more than, 1, 2, or 3 amino acids therefrom);

(b) a light chain variable region segment comprising:

a CDR1 comprising the sequence RASENVDKYG-NSFMH (SEQ ID NO: 6) (or a sequence that differs by no more than, 1, 2, 3, 4, or 5 amino acids therefrom), a CDR2 comprising the sequence RASELQW (SEQ ID NO: 7) (or a sequence that differs by no more than, 1, 2, or 3 amino acids therefrom), and a CDR3 comprising the sequence QRSNEVPWT (SEQ ID NO: 8) (or a sequence that differs by no more than, 1, 2, or 3 amino acids therefrom).

In some embodiments, V of HCDR1 is unchanged; in some embodiments, L of HCDR2 is unchanged, and in some embodiments, both V of HCDR1 and L of HCDR2 are unchanged.

In certain embodiments, the antibody molecule comprises a VH FW1 having the sequence QVQLVQSGAEVKKP-GASVKVSCKAGFNIK (SEQ ID NO: 11), or an amino acid sequence having no more than 1, 2, 3, 4, or 5 mutations relative to SEQ ID NO: 11.

In certain embodiments, the antibody molecule comprises a VH FW2 having the sequence WVRQAPGQGLEWMG (SEQ ID NO: 84), or an amino acid sequence having no more than 1, 2, 3, 4, or 5 mutations relative to SEQ ID NO: 84. In certain embodiments, the antibody molecule comprises a VH FW2 having the sequence WVRQAPEQ-GLEWMG (SEQ ID NO: 85), or an amino acid sequence having no more than 1, 2, 3, 4, or 5 mutations relative to SEQ ID NO: 85.

In certain aspects, the present disclosure provides an antibody molecule capable of binding dengue virus, comprising:

(a) a heavy chain immunoglobulin variable region segment comprising:

a FW1 comprising a deletion of position 26 relative to SEQ ID NO: 33;

a CDR1 comprising the sequence DTYMS (SEQ ID NO: 14) (or a sequence that differs by no more than, 1, 2, or 3 amino acids therefrom, optionally provided that T is unchanged), or a CDR1 comprising the sequence DVYMS (SEQ ID NO: 3) (or a sequence that differs by no more than, 1, 2, or 3 amino acids therefrom, optionally provided that V is unchanged), a CDR2 comprising the sequence RIDPENGDTKYDPK LQG (SEQ ID NO: 4) (or a sequence that differs by no more than, 1, 2, 3, 4, or 5 amino acids therefrom, optionally provided that L is unchanged), and a CDR3 comprising the sequence GWEGFAY (SEQ ID NO: 5) (or a sequence that differs by no more than, 1, 2, or 3 amino acids therefrom); and (b) a light chain variable region segment comprising:

a CDR1 comprising the sequence RASENVDKYG-NSFMH (SEQ ID NO: 6) (or a sequence that differs by no more than, 1, 2, 3, 4, or 5 amino acids therefrom), a CDR2 comprising the sequence RASELQW (SEQ ID NO: 7) (or a sequence that differs by no more than, 1, 2, or 3 amino acids therefrom), and a CDR3 comprising the sequence QRSNEVPWT (SEQ ID NO: 8) (or a sequence that differs by no more than, 1, 2, or 3 amino acids therefrom).

In certain embodiments, the antibody molecule comprises a VH FW2 having the sequence WVRQAPGQGLEWMG (SEQ ID NO: 84), or an amino acid sequence having no more than 1, 2, 3, 4, or 5 mutations relative to SEQ ID NO: 84. In certain embodiments, the antibody molecule comprises a VH FW2 having the sequence WVRQAPEQ-GLEWMG (SEQ ID NO: 85), or an amino acid sequence having no more than 1, 2, 3, 4, or 5 mutations relative to SEQ ID NO: 85.

In certain aspects, the present disclosure provides an antibody molecule, optionally capable of binding dengue virus, comprising:

(a) a heavy chain immunoglobulin variable region segment comprising:

a CDR1 comprising the sequence DVYMS (SEQ ID NO: 3) (or a sequence that differs by no more than, 1, 2, or 3 amino acids therefrom, optionally provided that V is unchanged), a CDR2 comprising the sequence RIDPENGDTKYDPK LQG (SEQ ID NO: 4) (or a sequence that differs by no more than, 1, 2, 3, 4, or 5 amino acids therefrom, optionally provided that L is unchanged), and a CDR3 comprising the sequence GWEGFAY (SEQ ID NO: 5) (or a sequence that differs by no more than, 1, 2, or 3 amino acids therefrom), optionally provided that A is replaced with I, K, D or E;

(b) a light chain variable region segment comprising:

a CDR1 comprising the sequence RASENVDK YGNSFMH (SEQ ID NO: 6) (or a sequence that differs by no more than, 1, 2, 3, 4, or 5 amino acids therefrom), optionally provided at Y is replaced with F, a CDR2 comprising the sequence RASELQW (SEQ ID NO: 7) (or a sequence that differs by no more than, 1, 2, or 3 amino acids therefrom), and a CDR3 comprising the sequence QRSNEVPWT (SEQ ID NO: 8) (or a sequence that differs by no more than, 1, 2, or 3 amino acids therefrom).

Accordingly, in some embodiments, the heavy chain CDR3 is GWEGFIY (SEQ ID NO: 90), GWEGFKY (SEQ ID NO: 91), GWEGFDY (SEQ ID NO: 92), or GWEGFEY (SEQ ID NO: 93). In some embodiments, the light chain CDR1 is RASENVDKFGNSFMH (SEQ ID NO: 94). Put another way, in some embodiments, position 105 of the heavy chain, which is alanine in antibody A11, may be changed to another residue, e.g., an I, K, D or E. In certain embodiments, position 32 of the light chain, which is tyrosine in antibody A11, is changed to another residue, e.g., F. In some embodiments, a mutation described in this paragraph improves the antibody molecule's affinity for EDIII and/or its neutralization activity towards one or more (or all) strain or serotype of dengue virus.

In certain embodiments, the antibody molecule comprises a VH FW1 having the sequence QVQLVQSGAEVKKP-GASVKVSCKAGFNIK (SEQ ID NO: 11), or an amino acid sequence having no more than 1, 2, 3, 4, or 5 mutations relative to SEQ ID NO: 11.

In certain embodiments, the antibody molecule comprises a VH FW2 having the sequence WVRQAPGQGLEWMG (SEQ ID NO: 84), or an amino acid sequence having no more than 1, 2, 3, 4, or 5 mutations relative to SEQ ID NO: 84. In certain embodiments, the antibody molecule comprises a VH FW2 having the sequence WVRQAPEQ-GLEWMG (SEQ ID NO: 85), or an amino acid sequence having no more than 1, 2, 3, 4, or 5 mutations relative to SEQ ID NO: 85.

In some embodiments of the aspects herein, the antibody molecule is capable of binding to dengue virus EDIII (E protein domain III). In certain embodiments, the antibody molecule comprises one or more CDRs having the sequence of any of SEQ ID NOS: 3-8, 14, and 35 (or a sequence that differs by no more than, 1, 2 or 3 amino acids therefrom). For example, the antibody molecule may comprise at least two, three, four, five, or six CDRs having the sequence of any of SEQ ID NOS: 3-8, 14, and 35.

In some embodiments, the antibody molecule comprises a VH CDR1 of SEQ ID NO: 3 or 14, a VH CDR2 of SEQ ID NO: 4 or 35, a VH CDR3 of SEQ ID NO: 5, a VL CDR1 of SEQ ID NO: 6, a VL CDR2 of SEQ ID NO: 7, and a VL CDR3 of SEQ ID NO: 8. For instance, the antibody molecule may comprise a VH CDR1 of SEQ ID NO: 3, a VH CDR2 of SEQ ID NO: 4, a VH CDR3 of SEQ ID NO: 5, a VL CDR1 of SEQ ID NO: 6, a VL CDR2 of SEQ ID NO: 7, and a VL CDR3 of SEQ ID NO: 8.

In some embodiments, the antibody molecule comprises a VH amino acid sequence at least 70%, 80%, 85%, 90%, 95%, 99%, or 100% identical to SEQ ID NO: 1.

In some embodiments, the antibody molecule comprises a VH amino acid sequence at least 70%, 80%, 85%, 90%, 95%, 99%, or 100% identical to SEQ ID NO: 80.

In some embodiments, the antibody molecule comprises a VH amino acid sequence at least 70%, 80%, 85%, 90%, 95%, 99%, or 100% identical to any of SEQ ID NOs. 16-21, 24, 25, 27, 29, 31, 32, 33, 36, 80, or 81. In some embodiments, the antibody molecule comprises a VL amino acid sequence at least 70%, 80%, 85%, 90%, 95%, 99%, or 100% identical to SEQ ID NO: 2 or 34.

In certain embodiments, the antibody molecule is a Fab, F(ab')2, Fv, or a single chain Fv fragment (scFv). In some embodiments, the antibody molecule comprises a heavy chain constant region selected from IgG1, IgG2, IgG3, and IgG4. In some embodiments, the antibody molecule comprises a light chain constant region chosen from the light chain constant regions of kappa or lambda.

The antibody molecule may be an isolated antibody molecule and/or a humanized antibody molecule. In some embodiments, the antibody molecule contains one or more framework regions derived from a human framework germline sequence.

In some embodiments, the antibody molecule is capable of binding to dengue virus EDIII with a dissociation constant ($K_D$) of less than about 80, 70, 60, 50, 40, 30, 20, 10, 8, 6, 4, 3, 2, 1, 0.5, 0.2, or 0.1 nM. The antibody molecule may be capable of binding to dengue virus serotype DV-4 EDIII with a dissociation constant ($K_D$) of less than about 10, 8, 6, 5, 4, or 3 nM. The antibody molecule may be capable of binding to DV-3 or DV-4 EDIII domain with at least a 2, 3, 4, 5, 6, 8, 10, 12, 100, 1,000-fold greater affinity than antibody A11 or antibody 4E11. The antibody molecule may be capable of binding to a dengue virus strain chosen from one or more of DENV-4 BC2, DENV-4-Sing10, DENV-4 NewCal09, DENV-4 Phil56, DENV-3 Sing09, DENV-3 Nic10, DENV-3 H87, DENV-2 Peru95, DENV-2 Sing08, DENV-2 NGC, DENV-1 Hawaii/1944, DENV-2 New Guinea/1944 (NGC), DENV-3 Philippines/1956 (H87), DENV-4 Mexico/1997 (BC287/97), and DENV-4 H241, with at least 2, 3, 4, 5, 6, 8, 10, 12, 25, 50, 75, 100, or 1,000-fold greater affinity than antibody A11 or antibody 4E11. The antibody molecule may be capable of neutralizing dengue virus in a focus reduction neutralization test or a related test for evaluating neutralization of viral activity. The antibody molecule may be capable of neutralizing dengue virus with an IC50 that is at least 2, 3, 4, 5, 6, 8, 10, 12, 50, 75, or 100-fold lower than antibody A11 or antibody 4E11 in a focus reduction neutralization test or a related test for evaluating neutralization of viral activity.

In some aspects, the present disclosure provides a pharmaceutical composition comprising the antibody molecule of any of the above claims and a pharmaceutically acceptable carrier, excipient, or stabilizer.

The present disclosure also provides, e.g., a nucleic acid encoding the antibody heavy or light chain variable region of an antibody molecule as described herein. The disclosure also provides, for example, expression vector comprising such a nucleic acid. The disclosure also provides, for example, a host cell comprising such a nucleic acid. The present disclosure additionally provides, e.g., a method of producing an antibody molecule or fragment thereof as described herein, comprising culturing the host cell under conditions suitable for gene expression.

In some aspects, this disclosure provides a kit comprising an antibody molecule as described herein. The kit may comprise a container, and the container may have the antibody molecule disposed therein. The kit may also comprise a pharmaceutically acceptable carrier, excipient, or stabilizer, optionally admixed with the antibody molecule. The kit may also comprise a delivery device, e.g., one comprising a syringe or needle. The kit may also comprise instructions for use.

In certain aspects, the present disclosure provides a method of neutralizing dengue virus, comprising: contacting the dengue virus with an antibody molecule as described herein. In some embodiments, the dengue virus is of serotype DV-1, DV-2, DV-3, or DV-4.

In some aspects, the present disclosure provides a method of treating a dengue virus infection, comprising administering to a subject in need thereof an isolated antibody molecule as described herein, in an amount effective to treat the virus. The method may further comprise administering an anti-viral agent to the subject, e.g., an anti-viral agent chosen from one or more of balapiravir, chloroquine, celgosivir, ivermectin, or *Carica folia*. In certain embodiments, the antiviral agent is a second anti-dengue antibody molecule, e.g., an anti-dengue antibody molecule described herein different from a first anti-dengue antibody molecule. In other embodiments, the antiviral agent is selected from an alpha-glucosidase I inhibitor (e.g., celgosivir), an adenosine nucleoside inhibitor (e.g., NITD008); an RNA-dependent RNA polymerase (RdRp) inhibitor (e.g., NITD107), an inhibitor of host pyrimidine biosynthesis, e.g., host dihydroorotate dehydrogenase (DHODH) (e.g., NITD-982 and brequinar), an inhibitor of viral NS4B protein (e.g., NITD-618), and an iminosugar (e.g., UV-4). The method may further comprise administering a vaccine to the subject, e.g., a dengue virus vaccine. In some embodiments, administration of the antibody molecule is parenteral or intravenous.

The disclosure also provides prophylactic methods. In some embodiments, a method of preventing a dengue virus infection by administering an antibody molecule as disclosed herein to a subject who is not, at the time, infected with dengue virus. For instance, in certain aspects, the present disclosure provides a method of reducing a patient's risk of contracting dengue virus, comprising administering to a subject in need thereof an isolated antibody molecule as described herein, in an amount effective to reduce the risk of contracting the virus. For example the risk of contracting dengue virus may be reduced by, e.g., at least 25%, 50%, 75%, 80%, 85%, 90%, 95%, 97%, 98%, 99%, or more. In some embodiments, the antibody molecule is provided to a patient who is not infected with dengue virus, with the result that if infection occurs, the course of the disease is likely to be milder than the course of disease in a similar patient who has not received the antibody molecule. For instance, the antibody molecule may reduce the risk of dengue fever developing (e.g., the patient is more likely to experience an asymptomatic infection). The risk of dengue fever developing may be reduced, e.g., by at least 25%, 50%, 75%, 80%, 85%, 90%, 95%, 97%, 98%, 99%, or more compared to a patient that did not receive the antibody molecule. In some embodiments, the risk of dengue fever progressing into dengue hemorrhagic fever may be reduced, e.g., by at least 25%, 50%, 75%, 80%, 85%, 90%, 95%, 97%, 98%, 99%, or more compared to a patient that did not receive the antibody molecule. The disclosure also provides methods of reducing or preventing transmission of dengue virus (e.g., reducing or preventing transmission between a subject (e.g., a human) and a mosquito. In certain embodiments, the subject is infected with dengue virus. In other embodiments, the subject is not, at the time, infected with dengue virus, but is at risk of dengue viral infection. For instance, in certain aspects, the present disclosure provides a method of reducing or preventing transmission of dengue virus (e.g., reducing or preventing transmission of dengue virus between a subject (e.g., human) and a mosquito), comprising administering to a subject an isolated antibody molecule as described herein, in an amount effective to reduce the transmission of dengue virus. For example, the transmission of dengue virus, e.g., from a subject to a mosquito, can be reduced by, e.g., at least about 10%, 20%, 30%, 40%, 50%, 60%, 70%, 80%, or 90%, compared to the transmission from a subject that did not receive the antibody molecule, e.g., as measured by a mosquito model described herein. As a result, in some embodiments, the transmission of dengue virus from an infected mosquito to an uninfected subject (e.g., human) can be further reduced, e.g., at least about 10%, 20%, 30%, 40%, 50%, 60%, 70%, 80%, or 90%.

In certain aspects, this disclosure provides a method of detecting dengue virus in a biological sample, comprising (i) contacting the sample or the subject (and optionally, a reference sample or subject) with an antibody molecule described herein under conditions that allow interaction of the antibody molecule and the polypeptide to occur, and (ii) detecting formation of a complex between the antibody molecule and the sample or the subject (and optionally, the reference sample or subject).

In some aspects, this disclosure provides an anti-dengue antibody molecule comprising a VH region that has a deletion of position 26 relative to the VH of antibody A11. For instance, the anti-dengue antibody molecule of claim may have a VH region with between about 1-30, 5-30, 10-30, 15-30, or 20-25 mutations relative to a VH of antibody A11.

In some aspects, this disclosure provides an antibody molecule capable of binding to dengue virus, which comprises a VH CDR1 having the sequence of SEQ ID NO: 3, or an amino acid sequence having no more than 1, 2, 3, 4, 5, 10, or 15 mutations relative to SEQ ID NO: 3. In some embodiments, the mutations are substitutions, e.g., conservative substitutions.

In certain aspects, this disclosure provides an antibody molecule capable of binding to dengue virus, which comprises a VH FW1 having the sequence QVQLVQS-GAEVKKPGASVKVSCKAGFNIK (SEQ ID NO: 11), or an amino acid sequence having no more than 1, 2, 3, 4, 5, 10, or 15 mutations relative to SEQ ID NO: 11. In some embodiments, the mutations are independently selected from deletions and substitutions, e.g., conservative substitutions. An antibody molecule of this paragraph may also have the features described throughout this application, e.g., in the previous paragraph.

In some aspects, this disclosure provides antibody molecules capable of binding to dengue virus, which comprises a VH CDR2 having the sequence of SEQ ID NO: 4, or an amino acid sequence having no more than 1, 2, 3, 4, 5, 10, or 15 mutations relative to SEQ ID NO: 4. In some embodiments, the mutations are substitutions, e.g., conservative substitutions. An antibody molecule of this paragraph may also have the features described throughout this application, e.g., in the previous two paragraphs.

In certain aspects, this disclosure provides an antibody molecule capable of binding to dengue virus, which comprises a VH FW2 having the sequence WVRQAPGQ-GLEWMG (SEQ ID NO: 84) or WVRQAPEQGLEWMG (SEQ ID NO: 85), or an amino acid sequence having no more than 1, 2, 3, 4, 5, or 10 mutations relative to SEQ ID NO: 84 or SEQ ID NO: 85. In some embodiments, the mutations are independently selected from deletions and substitutions, e.g., conservative substitutions. An antibody molecule of this paragraph may also have the features described throughout this application, e.g., in the previous paragraph.

In some embodiments, the antibody molecule is capable of binding to EDIII of two or more, e.g., three or four, dengue virus serotypes, e.g., selected from DV-1, DV-2, DV-3, and DV-4, with a dissociation constant ($K_D$) of less than about 80, 70, 60, 50, 40, 30, 20, 10, 8, 6, 4, 3, 2, 1, 0.5, 0.2, 0.1, 0.05, or 0.01 nM for each of said two or more serotypes.

In some embodiments, the antibody molecule has a variable region that is identical in sequence, or which differs by 1, 2, 3, or 4 amino acids from a variable region described herein (e.g., an FR region disclosed herein).

In some embodiments, the anti-dengue antibody molecule is a full antibody or fragment thereof (e.g., a Fab, F(ab')2, Fv, or a single chain Fv fragment (scFv)). In certain embodiments, the anti-dengue antibody molecule is a monoclonal antibody or an antibody with single specificity. The anti-dengue antibody molecule can also be a humanized, chimeric, camelid, shark, or in vitro-generated antibody molecule. In some embodiments, the anti-dengue antibody molecule thereof is a humanized antibody molecule. The heavy and light chains of the anti-dengue antibody molecule can be full-length (e.g., an antibody can include at least one or at least two complete heavy chains, and at least one or at least two complete light chains) or can include an antigen-binding fragment (e.g., a Fab, F(ab')2, Fv, a single chain Fv fragment, a single domain antibody, a diabody (dAb), a bivalent or bispecific antibody or fragment thereof, a single domain variant thereof, or a camelid antibody).

In certain embodiments, the anti-dengue antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1 or IgG2). In some embodiments, the heavy chain constant region is human IgG1. In some embodiments, the anti-dengue antibody molecule has a light chain constant region chosen from, e.g., the light chain constant regions of kappa or lambda, in some embodiments kappa (e.g., human kappa). In some embodiments, the constant region is altered, e.g., mutated, to modify the properties of the anti-dengue antibody molecule (e.g., to increase or decrease one or more of: Fc receptor binding, antibody glycosylation, the number of cysteine residues, effector cell function, or complement function). For example, the constant region may be mutated at positions 234 (e.g., L to A), 235 (e.g., L to A), 296 (e.g., M to Y), 297 (e.g., N to A or G or Q), 298 (e.g., S to T), 300 (e.g., T to E), 477 (e.g., H to K) and 478 (e.g., N to F) to alter Fc receptor binding.

In some embodiments, the antibody molecule is a humanized antibody molecule.

In some embodiments, the antibody molecule is isolated or recombinant.

In some embodiments, the anti-dengue antibody molecules comprise combinations of human or humanized framework regions with CDRs (complementarity determining regions).

The present disclosure also provides nucleic acids comprising nucleotide sequences that encode heavy and light chain variable regions and CDRs of the anti-dengue antibody molecules, as described herein. For example, the disclosure provides a first and second nucleic acid encoding heavy and light chain variable regions, respectively, of an anti-dengue antibody molecule according to Table 1, e.g., D88, A48, F38, F108, or C88, or a sequence substantially identical thereto. For example, the nucleic acid can comprise a nucleotide sequence encoding an anti-dengue antibody molecule according to Table 1, e.g., D88, A48, F38, F108, or C88, or a sequence substantially identical to that nucleotide sequence (e.g., a sequence at least about 85%, 90%, 95%, 99% or more identical thereto, or which differs by no more than 3, 6, 15, 30, or 45 nucleotides from the aforementioned nucleotide sequence). In certain embodiments, the nucleic acid can comprise a nucleotide sequence encoding at least one, two, or three CDRs from a heavy chain variable region having an amino acid sequence as set forth in Table 2, or a sequence substantially homologous thereto (e.g., a sequence at least about 85%, 90%, 95%, 99% or more identical thereto, and/or having one, two, three or more substitutions, insertions or deletions, e.g., conserved substitutions). In certain embodiments, the nucleic acid can comprise a nucleotide sequence encoding at least one, two, or three CDRs from a light chain variable region having an amino acid sequence as set forth in Table 2, or a sequence substantially homologous thereto (e.g., a sequence at least about 85%, 90%, 95%, 99% or more identical thereto, and/or having one, two, three or more substitutions, insertions or deletions, e.g., conserved substitutions). In some embodiments, the nucleic acid can comprise a nucleotide sequence encoding at least one, two, three, four, five, or six CDRs from heavy and light chain variable regions having an amino acid sequence as set forth in Table 2, or a sequence substantially homologous thereto (e.g., a sequence at least about 85%, 90%, 95%, 99% or more identical thereto, and/or having one, two, three or more mutations (e.g., substitutions, insertions or deletions, e.g., conserved substitutions). In some embodiments, a nucleic acid having a structural feature discussed in this paragraph encodes an antibody molecule or portion thereof having one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

This disclosure also provides nucleic acid sequences, e.g., a nucleic acid that hybridizes to a nucleic acid sequence that encodes an antibody of Table 1, e.g., D88, A48, F38, F108, or C88, and its complement, e.g., under low stringency, medium stringency, or high stringency, or other hybridization condition described herein. This application also discloses nucleic acid sequences of Table 4, and their complements, e.g., under low stringency, medium stringency, or high stringency, or other hybridization condition described herein. In some embodiments, the nucleic acid is at least 80%, 85%, 90%, 92%, 95%, 97%, 98%, 99% or higher identical to a sequence of Table 4, its complement, or a portion of any of the aforementioned sequences. In some embodiments, a nucleic acid having a structural feature discussed in this paragraph encodes an antibody molecule or portion thereof having one or more advantageous properties such as an improved (e.g., relative to A11) affinity for or neutralization activity towards dengue virus, e.g., DV-4. In some embodiments, the advantageous property is a property of List 1, e.g., one or more (e.g., two, three, four, five, six, seven, eight, nine, ten, eleven, twelve, thirteen, fourteen, fifteen, sixteen, or all) of properties (a), (b), (c), (d), (e), (m), (n), (o), (p), (q), (r), (s), (t), (u), (v), (w), or (x).

In certain aspects, this disclosure features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include human cells e.g., HEK293 cells, lymphocytic cell lines (e.g., NS0), Chinese hamster ovary cells (CHO), COS cells, oocyte cells, and cells from a transgenic animal.

In some aspects, the present disclosure provides a method of providing an antibody molecule described herein. The method may include: providing an antibody molecule that specifically binds to an EDIII antigen; making one or more mutations to the antibody (e.g., to the constant region, framework, and/or CDRs) and evaluating if the antibody molecule specifically binds to the EDIII antigen, or evaluating efficacy of the antibody molecule in inhibiting dengue virus function. The method can further include purifying the antibody molecule. For example, the antibody molecule can be purified by one or more chromatography steps comprising, e.g., affinity chromatography, e.g., Protein A chromatography. The method can further include administering the antibody molecule to a subject, e.g., a human or non-human animal.

In certain aspects, the disclosure provides, compositions, e.g., pharmaceutical compositions, which include a pharmaceutically acceptable carrier, excipient or stabilizer, and at least one of the anti-dengue antibody molecules described herein. In some embodiments, the antibody molecule is conjugated to a label or a therapeutic agent. In some embodiments, the compositions, e.g., the pharmaceutical compositions, comprise a combination of the antibody molecule and a second agent, e.g., a therapeutic agent, or two or more of the aforesaid antibody molecules, as further described herein.

The antibody molecules disclosed herein can inhibit one or more activities of dengue virus. For instance, the antibody molecules may disrupt the native structure of the E protein on the surface of the virion, e.g., causing inactivation of the virus. As a result, the antibody molecule may neutralize the virus, inhibit its ability to enter a host cell, or reduce viral stability. In some embodiments, an antibody molecule neutralizes dengue virus (e.g., in a focus reduction neutralization test or a related test for evaluating neutralization of viral activity) with an EC50 or FRNT50 of less than or equal to 1400, 1000, 800, 600, 550, 500, 450, 400, 350, 300, 350, 200, 150, 100, 50, or 25 ng/ml. In some embodiments, the antibody neutralizes dengue virus (e.g., in a focus reduction neutralization test or a related test for evaluating neutralization of viral activity) with an IC50 of less than or equal to 20, 17.6, 15, 10, 5, 4, 2, 1.4, 1, or 0.50 µg/mL. In some embodiments, neutralization of DV-4 is tested, and in some embodiments, neutralization of one of DV-1, DV-2, or DV-3 is tested.

The subject can be a mammal, e.g., a monkey, a primate, preferably a higher primate, e.g., a human (e.g., a patient having, or at risk of having, dengue virus).

This disclosure also provides a method of treating dengue virus in a subject, comprising administering to the subject an anti-dengue antibody molecule described herein, e.g., a therapeutically effective amount of an anti-dengue antibody molecule, or an antigen-binding portion thereof. In some embodiments, the anti-dengue antibody molecule is administered to a patient suffering from dengue virus, resulting in the reduction of viral load and/or the reduction of at least one symptom, e.g., selected from sudden-onset fever, headache, muscle and joint pains, weight loss, central nervous system penetration, and/or rash. In some embodiments, the anti-dengue antibody molecule is administered to a patient at risk of being infected from dengue virus, resulting in the reduction of the risk of becoming infected or reduction of the severity of the infection if infection does occur.

The anti-dengue antibody molecule can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The methods and compositions described herein can be used in combination with other therapeutic modalities. In some embodiments, the methods of described herein include administering to the subject an anti-dengue antibody molecule as described herein, in combination with a second treatment or prophylactic for dengue virus, in an amount effective to treat or prevent said disorder. The antibody molecule and the second agent can be administered simultaneously or sequentially.

Any combination and sequence of the anti-dengue antibody molecules and other therapeutic modalities can be used. The anti-dengue antibody molecule and/or other therapeutic modalities can be administered during periods of active infection, or during a period of remission or less active disease. The anti-dengue antibody molecule and other therapeutic modalities can be administered before treatment, concurrently with treatment, post-treatment, or during remission of the infection.

In some aspects, the present disclosure provides methods for detecting the presence of dengue virus in a sample, e.g., in vitro or in vivo (e.g., a biological sample, e.g., blood or serum). The methods herein can be used to evaluate (e.g., monitor treatment or progression of, diagnose and/or stage a disorder described herein, e.g., dengue virus, in a subject). The method may include: (i) contacting the sample with (and optionally, a reference, e.g., a control sample), or administering to the subject, an anti-dengue antibody molecule as described herein, under conditions that allow interaction to occur, and (ii) detecting whether there is formation of a complex between the antibody molecule and the sample (and optionally, the reference, e.g., control, sample). Formation of the complex is indicative of the presence of dengue virus, and can indicate the suitability or need for a treatment described herein. The method can involve, e.g., an immunohistochemistry, immunocytochemistry, FACS, antibody molecule-complexed magnetic beads, ELISA assays, or PCR-techniques (e.g., RT-PCR).

Typically, the anti-dengue antibody molecule used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials.

In some aspects, the present disclosure provides diagnostic or therapeutic kits that include the anti-dengue antibody molecules described herein and instructions for use.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

Figures and Tables are provided herewith.

BRIEF DESCRIPTION OF THE DRAWINGS

Each of the Figures is described herein in more detail.

FIGS. 1A-1I show the amino acid and nucleotide sequences of several anti-dengue EDIII antibodies. Kabat CDRs are underlined, and certain residues of interest are boxed (shown with a gray background in the priority documents).

FIG. 4 is a functional assessment of frameworks of several humanized EDIII antibodies.

FIG. 5 shows antibody affinity upon back-mutations of the N-terminus of anti-dengue antibodies. Heavy chain FW "04" refers to a type of framework that has the same heavy chain framework amino acid sequence as, e.g., mAb B48. Light chain FW "08" refers to a type of framework that has the same light chain framework amino acid sequence as, e.g., mAb B48. The heavy and light chain framework sequences of mAb B48 are shown in Tables 1 and 2.

FIG. 6 shows that combining certain point mutations leads to improved affinity for EDIII. Light chain FW "08" refers to a type of framework that has the same light chain framework amino acid sequence as, e.g., mAb D88. The light chain framework sequence of mAb D88 is shown in Tables 1 and 2.

FIG. 7 shows the results of setting position 98 to A, V, or S in combination with other mutations.

FIG. 8 shows the results of competition ELISA to determine the EDIII binding affinity of select antibodies.

FIG. 9 shows the binding of selected anti-dengue antibodies to EDIII of four dengue virus serotypes.

FIG. 10B shows the binding of antibody D88 to a panel of diverse dengue virus isolates. * indicates strain used for in vitro neutralization testing.

FIG. 11 shows the affinity of selected anti-dengue antibodies for various strains of dengue virus.

FIGS. 15A-15C show the thermal stability of selected anti-dengue antibodies based on a thermal shift analysis assay (Sypro Orange).

FIG. 20 shows the ability of antibody D88 to neutralize dengue virus serotypes DENV-1, DENV-2, DENV-3, and DENV-4 propagated in Vero (monkey) cells in a focus reduction neutralization test (FRNT).

FIG. 23 depicts the affinity gain of antibody D88 to DENV-4 with concurrent improved affinity to DENV-1, DENV-2 and DENV-3 compared to antibody 4E11.

BRIEF DESCRIPTION OF THE TABLES

Figure 2:
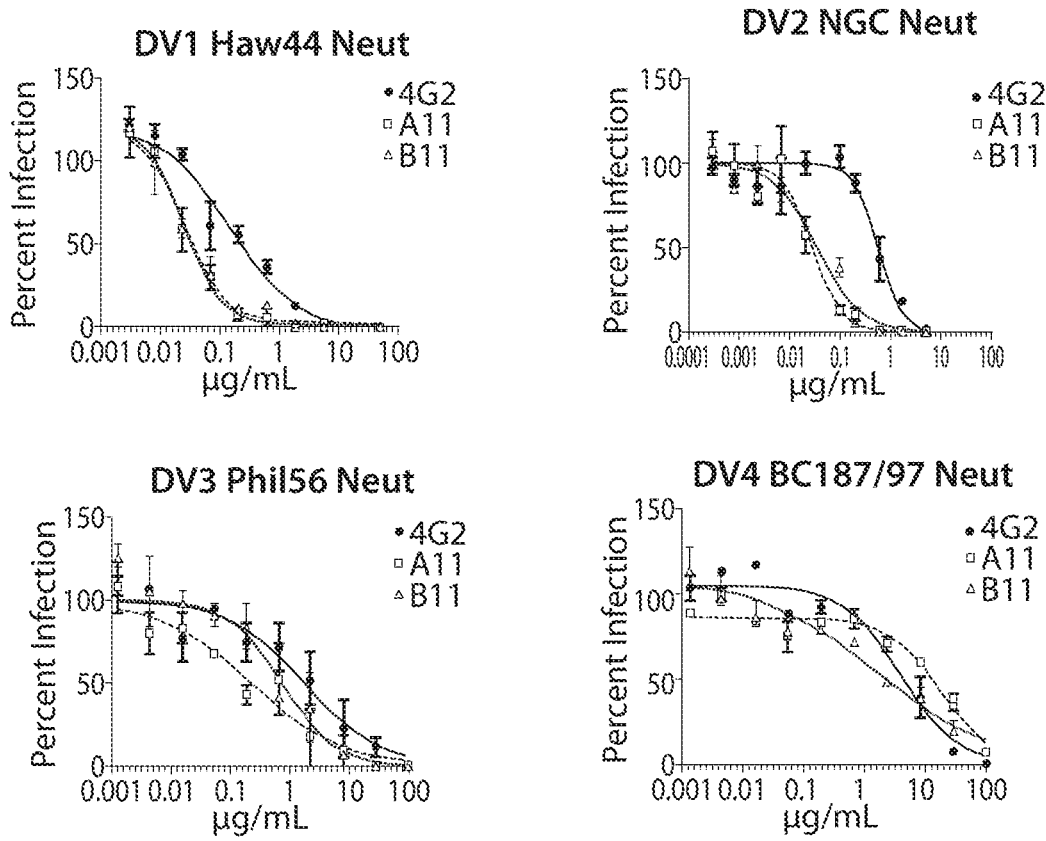
FIG. 2 depicts the results of a focus reduction neutralization test using live virus showing that antibody B11 improves upon mAb A11 neutralization of DV4.

Each of the Tables is described herein in more detail.

Table 1 summarizes the sequences of exemplary anti-dengue antibodies.

Table 2 depicts the amino acid sequences of the heavy chain variable domain and light chain variable domain sequences of Table 1. Kabat CDRs are underlined, Chothia CDRs are italicized, and certain residues of interest are shown with a gray background.

Table 3 depicts the amino acid sequences of the CDRs of Table 1.

Table 4 summarizes the nucleic acid sequences encoding the antibodies of Table 1.

Table 5 depicts the nucleic acid sequences summarized in Table 4.

Table 6 depicts additional amino acid sequences described throughout the application.

DETAILED DESCRIPTION

Disclosed herein are antibody molecules that bind to dengue virus epitopes, e.g., EDIII, with high affinity and specificity. Advantageously, several of the antibody molecules herein bind with high affinity to EDIII of dengue virus serotypes DV-1, DV-2, DV-3, and DV-4. Nucleic acid molecules encoding the antibody molecules, expression vectors, host cells and methods for making the antibody molecules are also provided. The anti-dengue antibody molecules disclosed herein can be used (alone or in combination with other agents or therapeutic modalities) to treat, prevent and/or diagnose dengue virus, e.g., DV-1, DV-2, DV-3, or DV-4. As used herein, DV-1, DV-2, DV-3, and DV-4 are sometimes referred to as DENV-1, DENV-2, DENV-3, and DENV-4, respectively.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are suitable conditions and the ones that should be used unless otherwise specified.

It is understood that the molecules described herein may have additional conservative or non-essential amino acid substitutions, which do not have a substantial effect on their functions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein.

The terms "nucleic acid," "nucleic acid sequence," "nucleotide sequence," or "polynucleotide sequence," and "polynucleotide" are used interchangeably.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat", e.g., a dengue virus infection, means that a subject (e.g., a human) who has been infected with a virus and experiences symptoms of the virus, will, in embodiments, suffer less severe symptoms and/or will recover faster when the antibody molecule is administered than if the antibody were never administered. In embodiments, when an infection is treated, an assay to detect virus in the subject will detect less virus after effective treatment for the infection. For example, a diagnostic assay using an antibody molecule, such as an antibody molecule described herein, will detect less or no virus in a biological sample of a patient after administration of an antibody molecule for the effective treatment of the infection. Other assays, such as PCR (e.g., qPCR) can also be used to monitor treatment in a patient, to detect the presence, e.g., decreased presence (or absence) after treatment of viral infection in the patient. Treatment can, e.g., partially or completely alleviate, ameliorate, relieve, inhibit, reduce the severity of, and/or reduce incidence and optionally, delay onset of, one or more manifestations of the effects or symptoms, features, and/or causes of a particular disease, disorder, and/or condition (e.g., dengue virus). In embodiments treatment is of a subject who does not exhibit certain signs of the relevant disease, disorder and/or condition and/or of a subject who exhibits only early signs of the disease, disorder, and/or condition. In embodiments treatment is of a subject who exhibits one or more established signs of the relevant disease, disorder and/or condition. In embodiments, treatment is of a subject diagnosed as suffering from dengue virus.

As used herein, the term "prevent", e.g., a dengue virus infection, means that a subject (e.g., a human) is less likely to be infected by a virus (e.g., dengue virus) if the subject receives the antibody prior to (e.g., 1 day, 2 days, 1 week, 2 weeks, 3 weeks, or 1 month of more) being exposed to the virus.

As used herein, the terms "framework," "FW" and "FR" are used interchangeably and have identical meaning in this document and its priority documents.

Various aspects of the compositions and methods herein are described in further detail below. Additional definitions are set out throughout the specification.

Anti-Dengue Antibody Molecules

Exemplary sequences of anti-dengue antibodies are described in Tables 1-4 below.

TABLE 1

Summary of the amino acid sequences of exemplary anti-dengue antibodies.

| Antibody designation | SEQ ID NO | Description |
| --- | --- | --- |
| D88 | 1 | VH amino acid sequence |
| | 2 | VL amino acid sequence |
| | 3 | VH CDR1 amino acid sequence, Kabat |
| | 4 | VH CDR2 amino acid sequence, Kabat |
| | 5 | VH CDR3 amino acid sequence, Kabat |
| | 6 | VL CDR1 amino acid sequence, Kabat |
| | 7 | VL CDR2 amino acid sequence, Kabat |
| | 8 | VL CDR3 amino acid sequence, Kabat |
| | 9 | VH CDR1 amino acid sequence, Chothia |
| | 10 | VH CDR2 amino acid sequence, Chothia |
| | 5 | VH CDR3 amino acid sequence, Chothia |
| | 6 | VL CDR1 amino acid sequence, Chothia |
| | 7 | VL CDR2 amino acid sequence, Chothia |
| | 8 | VL CDR3 amino acid sequence, Chothia |
| | 11 | VH FW1 amino acid sequence, Kabat |
| | 85 | VH FW2 amino acid sequence, Kabat |
| F38 | 80 | VH amino acid sequence |
| | 2 | VL amino acid sequence |
| | 3 | VH CDR1 amino acid sequence, Kabat |
| | 4 | VH CDR2 amino acid sequence, Kabat |
| | 5 | VH CDR3 amino acid sequence, Kabat |
| | 6 | VL CDR1 amino acid sequence, Kabat |
| | 7 | VL CDR2 amino acid sequence, Kabat |
| | 8 | VL CDR3 amino acid sequence, Kabat |
| | 9 | VH CDR1 amino acid sequence, Chothia |
| | 10 | VH CDR2 amino acid sequence, Chothia |
| | 5 | VH CDR3 amino acid sequence, Chothia |
| | 6 | VL CDR1 amino acid sequence, Chothia |
| | 7 | VL CDR2 amino acid sequence, Chothia |
| | 8 | VL CDR3 amino acid sequence, Chothia |
| | 11 | VH FW1 amino acid sequence, Kabat |
| | 84 | VH FW2 amino acid sequence, Kabat |
| A48 | 16 | VH amino acid sequence |
| | 2 | VL amino acid sequence |
| | 14 | VH CDR1 amino acid sequence, Kabat |
| | 4 | VH CDR2 amino acid sequence, Kabat |
| | 5 | VH CDR3 amino acid sequence, Kabat |
| | 6 | VL CDR1 amino acid sequence, Kabat |
| | 7 | VL CDR2 amino acid sequence, Kabat |
| | 8 | VL CDR3 amino acid sequence, Kabat |
| | 15 | VH CDR1 amino acid sequence, Chothia |
| | 10 | VH CDR2 amino acid sequence, Chothia |
| | 5 | VH CDR3 amino acid sequence, Chothia |
| | 6 | VL CDR1 amino acid sequence, Chothia |
| | 7 | VL CDR2 amino acid sequence, Chothia |
| | 8 | VL CDR3 amino acid sequence, Chothia |

TABLE 1-continued

Summary of the amino acid sequences of exemplary anti-dengue antibodies.

| Antibody designation | SEQ ID NO | Description |
|---|---|---|
| C88 | 17 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 9 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
|  | 85 | VH FW2 amino acid sequence, Kabat |
| F108 | 81 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 9 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
|  | 84 | VH FW2 amino acid sequence, Kabat |
| B48 | 18 | VH amino acid sequence |
|  | 2 | VL amino acid sequence |
|  | 14 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 15 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| A68 | 19 | VH amino acid sequence |
|  | 2 | VL amino acid sequence |
|  | 14 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 15 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| A100 | 20 | VH amino acid sequence |
|  | 2 | VL amino acid sequence |
|  | 14 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 15 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| C58 | 21 | VH amino acid sequence |
|  | 2 | VL amino acid sequence |
|  | 14 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 22 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| C78 | 23 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 24 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| C68 | 25 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 26 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| D98 | 27 | VH amino acid sequence |
|  | 2 | VL amino acid sequence |
|  | 14 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 28 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| D188 | 29 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 30 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| C128 | 31 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |

TABLE 1-continued

Summary of the amino acid sequences of exemplary anti-dengue antibodies.

| Antibody designation | SEQ ID NO | Description |
|---|---|---|
|  | 7 | VL CDR2 amino acid sequence, Kabat |
|  | 8 | VL CDR3 amino acid sequence, Kabat |
|  | 9 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| C98 | 32 | VH amino acid sequence |
|  | 2 | VL amino acid sequence |
|  | 3 | VH CDR1 amino acid sequence, Kabat |
|  | 4 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 9 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| A11 | 33 | VH amino acid sequence |
|  | 34 | VL amino acid sequence |
|  | 14 | VH CDR1 amino acid sequence, Kabat |
|  | 35 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 15 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |
| B11 | 36 | VH amino acid sequence |
|  | 34 | VL amino acid sequence |
|  | 14 | VH CDR1 amino acid sequence, Kabat |
|  | 21 | VH CDR2 amino acid sequence, Kabat |
|  | 5 | VH CDR3 amino acid sequence, Kabat |
|  | 6 | VL CDR1 amino acid sequence, Kabat |
|  | 7 | VL CDR2 amino acid sequence, Kabat |
|  | 8 | VL CDR3 amino acid sequence, Kabat |
|  | 15 | VH CDR1 amino acid sequence, Chothia |
|  | 10 | VH CDR2 amino acid sequence, Chothia |
|  | 5 | VH CDR3 amino acid sequence, Chothia |
|  | 6 | VL CDR1 amino acid sequence, Chothia |
|  | 7 | VL CDR2 amino acid sequence, Chothia |
|  | 8 | VL CDR3 amino acid sequence, Chothia |

A11 and B11 are mouse antibodies, and the other antibodies of Table 1 are humanized antibodies.

TABLE 2

Depiction of the amino acid sequences of the heavy chain variable domain and light chain variable domain sequences of Table 1. CDRs, defined according to the Kabat system, are underlined and bold, while CDRs defined according to the Chothia system are italicized. Certain residues of interest are shown with a gray background. Deletions are indicated with a caret symbol (^).

| Description | SEQ ID NO | Sequence |
|---|---|---|
| D88 VH | 1 | QVQLVQSGAEVKKPGASVKVSCKA^*GFNIKDYYMS*WVRQAPEQGLEWMGRIDPENGDTKYDPKLQGRVTMTADTSTNTAYMELRSLRSDDTAVYYCAR*GWEGFAY*WGQGTLTVSS |
| D88 VL | 2 | DIVMTQSPASLAVSLGERATISCRASENVDKYGNSFMHWYQQKPGQPPKLLIYRASELQWGVPDRFSGSGSGTDFTLTISSLQAEDVAVYYCQRSNEVPWTFGQGTKLEIK |
| F38 VH | 80 | QVQLVQSGAEVKKPGASVKVSCKA^*GFNIKDYYMS*WVRQAPGQGLEWMGRIDPENGDTKYDPKLQGRVTMTADTSTNTAYMELRSLRSDDTAVYYCAR*GWEGFAY*WGQGTLTVSS |
| A48 VH | 16 | QVQLVQSGAEVKKPGASVKVSCKAS*GFNIKDTYMS*WVRQAPEQGLEWMGRIDPENGDTKYDPKLQGRVTMTADTSTNTAYMELRSLRSDDTAVYYCAR*GWEGFAY*WGQGTLTVSS |
| C88 VH | 17 | QVQLVQSGAEVKKPGASVKVSCKAS*GFNIKDYYMS*WVRQAPEQGLEWMGRIDPENGDTKYDPKLQGRVTMTADTSTNTAYMELRSLRSDDTAVYYCAR*GWEGFAY*WGQGTLTVSS |
| F108 VH | 81 | QVQLVQSGAEVKKPGASVKVSCKAS*GFNIKDYYMS*WVRQAPGQGLEWMGRIDPENGDTKYDPKLQGRVTMTADTSTNTAYMELRSLRSDDTAVYYCAR*GWEGFAY*WGQGTLTVSS |

TABLE 2-continued

Depiction of the amino acid sequences of the heavy chain variable domain and light chain variable domain sequences of Table 1. CDRs, defined according to the Kabat system, are underlined and bold, while CDRs defined according to the Chothia system are italicized. Certain residues of interest are shown with a gray background. Deletions are indicated with a caret symbol (^).

| Description | SEQ ID NO | Sequence |
| --- | --- | --- |
| B48 VH | 18 | QVQLVQSGAEVKKPGASVKVSCKA^*GFNIKDTYMSWVRQAPEQGLEWMGRID PENGDTKYDPKLQGRVTMTADTSTNTAYMELRSLRSDDTAVYYCAR*GWEGFA Y*WGQGTLTVSS |
| A68 VH | 19 | QVQLVQSGAEVKKPGASVKVSCKAS*GFNIKDTYMSWVRQAPEQGLEWMGRID PENGDTKYDPKLQGRVTMTADTSTNTAYYYCVR*GWEGFA Y*WGQGTLTVSS |
| A100 VH | 20 | QVQLVQSGAEVKKPGASVKVSCKAS*GFNIKDTYMSWVRQAPEQGLEWMGRID PENGDTKYDPKLQGRVTMTADTSTNTAYMELRSLRSDDTAVYYCSR*GWEGFA Y*WGQGTLTVSS |
| C58 VH | 21 | QVQLVQSGAEVKKPGASVKVSCKAS*YWNIKDTYMSWVRQAPEQGLEWMGRID PENGDTKYDPKLQGRVTMTADTSTNTAYMELRSLRSDDTAVYYCAR*GWEGFA Y*WGQGTLTVSS |
| C78 VH | 23 | QVQLVQSGAEVKKPGASVKVSCKAS*GFNIQDVYMS*WVRQAPEQGLEWMGRID PENGDTKYDPKLQGRVTMTADTSTNTAYMELRSLRSDDTAVYYCAR*GWEGFA Y*WGQGTLTVSS |
| C68 VH | 25 | QVQLVQSGAEVKKPGASVKVSCKAS*GFNISDVYMS*WVRQAPEQGLEWMGRID PENGDTKYDPKLQGRVTMTADTSTNTAYMELRSLRSDDTAVYYCAR*GWEGFA Y*WGQGTLTVSS |
| D98 VH | 27 | QVQLVQSGAEVKKPGASVKVSCKAS*AFNIKDTYMSWVRQAPEQGLEWMGRID PENGDTKYDPKLQGRVTMTADTSTNTAYMELRSLRSDDTAVYYCAR*GWEGFA Y*WGQGTLTVSS |
| D188 VH | 29 | QVQLVQSGAEVKKPGASVKVSCKAS*AFNIKDVYMSWVRQAPEQGLEWMGRID PENGDTKYDPKLQGRVTMTADTSTNTAYMELRSLRSDDTAVYYCAR*GWEGFA Y*WGQGTLTVSS |
| C128 VH | 31 | QVQLVQSGAEVKKPGASVKVSCKAS*GFNIKDVYMSWVRQAPEQGLEWMGRID PENGDTKYDPKLQGRVTMTADTSTNTAYMELRSLRSDDTAVYYCSR*GWEGFA Y*WGQGTLTVSS |
| C98 VH | 32 | QVQLVQSGAEVKKPGASVKVSCKAS*GFNIKDVYMSWVRQAPEQGLEWMGRID PENGDTKYDPKLQGRVTMTADTSTNTAYMELRSLRSDDTAVYYCVR*GWEGFA Y*WGQGTLTVSS |
| A11 VH | 33 | QVKLLEQSGAELVKPGASVRLSCTAS*GFNIKDTYMSWVKQRPEQGLEWIGRI DPENGDTKYDPKFQGKATITADTSSNTAYLHLSSLTSGDTAVYYCSR*GWEGF AY*WGQGTLVTVSA |
| A11 VL | 34 | ELVMTQTPASLAVSLGQRATISC*RASENVDKYGNSFMH*WYQQKAGQPPKLLI Y*RASELQW*GIPARFSGSGSRTDFTLTINPVEADDVATYFC*QRSNEVPWT*FGG GTKLEIK |
| B11 VH | 36 | QVKLLEQSGAELVKPGASVRLSCTA^*GFNIKDTYMSWVKQRPEQGLEWIGRI DPENGDTKYDPKFQGKATITADTSSNTAYLHLSSLTSGDTAVYYCSR*GWEGF AY*WGQGTLVTVSA |

Throughout this application, reference is made to amino acid positions based on the variable region of mouse antibody A11. The variable region of mouse antibody B11 has a deletion at position 26 relative to A11. The human variable region sequences in Table 1 have a deletion of the glutamic acid sequence at position 6 of A11. Consequently, sequences that carry a deletion relative to A11 use a numbering system that is offset. For example, A48 heavy chain has a deletion of the glutamic acid sequence at position 6 relative to A11. As a result, position 26 (a serine) of A48 VH is actually the twenty-fifth amino acid of the A48 VH sequence (SEQ ID NO: 16). As another example, D88 heavy chain has a deletion of the glutamic acid sequence at position 6 of A11 and a deletion of the serine at position 26 relative to A11. As a consequence, position 33 (a valine) of D88 VH is actually the thirty-first amino acid of the D88 VH sequence (SEQ ID NO: 1).

Some structural features of the antibodies can be noted based on the VH and VL sequences in Table 2. B11 has a deletion at position 26 relative to the A11 VH region. D88 is a humanized antibody that has a deletion at position 26 and a T33V mutation relative to the A48 VH region (remaining consistent with A11 numbering). F38 is a humanized antibody that has a deletion at position 26 and T33V and E43G mutations relative to the A48 VH region. A48 is a humanized antibody with the same CDRs as A11. C88 is a humanized antibody that has a T33V mutation relative to the A48 VH region. F108 is a humanized antibody that has T33V and E43G mutations relative to the A48 VH region. B48 is a humanized antibody that has a deletion at position 26 relative to the A48 VH region. A68 is a humanized antibody that has an A98V mutation relative to the A48 VH region. A100 is a humanized antibody that has an A98S mutation relative to the A48 VH region. C58 is a humanized antibody that has G27Y and F28W mutations relative to the A48 VH region. C78 is a humanized antibody that has K31Q and T33V mutations relative to the A48 VH region. C68 is a humanized antibody that has K31S and T33V mutations relative to the A48 VH region. D98 is a humanized antibody that has a G27A mutation relative to the A48 VH region.

Other variations of the antibodies of Tables 1 and 2 are envisioned. For instance, this application provides antibody B48+A98V, which has an A98V mutation relative to B48; A48+V2L, which has a V2L mutation relative to A48; A48+InsE6, which has an InsE6 mutation relative to A48; B48+V2L, which has a V2L mutation relative to B48; B48+InsE6, which has an InsE6 mutation relative to B48; D118, which has F28W and T33V mutations relative to A48; D128, which has G27A, F28W, and T33V mutations relative to A48; D138, which has G27Y, F28A, and T33V mutations relative to A48; D148, which has G27Y and T33V mutations relative to A48; D158, which has G27Y, F28G, and T33V mutations relative to A48; D168, which has F28Y and T33V mutations relative to A48; C98, which has T33V and A98V mutations relative to A48; C128, which has T33V and A98S mutations relative to A48; D178, which has Del26, T33V, and A98V mutations relative to A48; and D188, which has Del26, T33V, and A98S mutations relative to A48.

TABLE 3

Depiction of the amino acid sequences of the CDRs of Table 1.

| SEQ ID NO | Sequence |
|---|---|
| 3 | DVYMS |
| 4 | RIDPENGDTKYDPKLQG |

TABLE 3-continued

Depiction of the amino acid sequences of the CDRs of Table 1.

| SEQ ID NO | Sequence |
|---|---|
| 5 | GWEGFAY |
| 6 | RASENVDKYGNSFMH |
| 7 | RASELQW |
| 8 | QRSNEVPWT |
| 9 | GFNIKDV |
| 10 | DPENGD |
| 14 | DTYMS |
| 15 | GFNIKDT |
| 22 | YWNIKDT |
| 24 | GFNIQDV |
| 26 | GFNISDV |
| 28 | AFNIKDT |
| 30 | AFNIKDV |
| 35 | RIDPENGDTKYDPKFQG |

TABLE 4

Summary of the nucleic acid sequences encoding the antibodies of Table 1.

| Antibody designation | SEQ ID NO | Description |
|---|---|---|
| D88 | 37 | VH nucleic acid sequence |
|  | 38 | VL nucleic acid sequence |
| F38 | 82 | VH nucleic acid sequence |
|  | 38 | VL nucleic acid sequence |
| A48 | 39 | VH nucleic acid sequence |
|  | 38 | VL nucleic acid sequence |
| C88 | 40 | VH nucleic acid sequence |
|  | 38 | VL nucleic acid sequence |
| F108 | 83 | VH nucleic acid sequence |
|  | 38 | VL nucleic acid sequence |
| B48 | 41 | VH nucleic acid sequence |
|  | 38 | VL nucleic acid sequence |
| A68 | 42 | VH nucleic acid sequence |
|  | 38 | VL nucleic acid sequence |
| A100 | 86 | VH nucleic acid sequence |
|  | 38 | VL nucleic acid sequence |
| C58 | 43 | VH nucleic acid sequence |
|  | 38 | VL nucleic acid sequence |
| C78 | 44 | VH nucleic acid sequence |
|  | 38 | VL nucleic acid sequence |
| C68 | 45 | VH nucleic acid sequence |
|  | 38 | VL nucleic acid sequence |

TABLE 4-continued

Summary of the nucleic acid sequences encoding the antibodies of Table 1.

| Antibody designation | SEQ ID NO | Description |
|---|---|---|
| D98 | 46 | VH nucleic acid sequence |
|  | 38 | VL nucleic acid sequence |
| D188 | 87 | VH nucleic acid sequence |
|  | 38 | VL nucleic acid sequence |
| C128 | 88 | VH nucleic acid sequence |
|  | 38 | VL nucleic acid sequence |
| C98 | 89 | VH nucleic acid sequence |
|  | 38 | VL nucleic acid sequence |
| A11 | 47 | VH nucleic acid sequence |
|  | 48 | VL nucleic acid sequence |
| B11 | 49 | VH nucleic acid sequence |
|  | 48 | VL nucleic acid sequence |

TABLE 5

Nucleic acid sequences of Table 4

| SEQ ID NO | Sequence |
|---|---|
| 37 | CAAGTGCAACTCGTTCAGTCCGGAGCAGAAGTCAAGAAACCTGGAGCTTCAGTCAAAGTCAGCTGCAAGGCCGGCTTCAATATCAAGGACGTCTACATGTCCTGGGTGCGGCAGGCTCCAGAGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 38 | GATATTGTCATGACCCAAAGCCCAGCCTCCCTCGCCGTGTCTCTCGGAGAAAGAGCAACTATCTCGTGCCGGGCTTCGGAGAATGTGGACAAGTACGGCAACTCCTTCATGCACTGGTACCAGCAGAAACCGGGACAGCCGCCTAAACTGTTGATCTACCGGGCGTCAGAACTGCAATGGGGAGTGCCTGACAGGTTTTCGGGTTCGGGATCCGGCACGGATTTCACCCTCACTATCTCCAGCTGCAAGCAGAGGACGTTGCGGTGTACTACTGTCAGCGCTCAAACGAGGTCCCATGGACTTTTGGACAAGGGACCAAGCTGGAAATCAAG |
| 82 | CAAGTGCAACTCGTTCAGTCCGGAGCAGAAGTCAAGAAACCTGGAGCTTCAGTCAAAGTCAGCTGCAAGGCCGGCTTCAATATCAAGGACGTCTACATGTCCTGGGTGCGGCAGGCTCCAGGGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 39 | CAAGTGCAACTCGTTCAGTCCGGAGCAGAAGTCAAGAAACCTGGAGCTTCAGTCAAAGTCAGCTGCAAGGCCTCGGGCTTCAATATCAAGGACACCTACATGTCCTGGGTGCGGCAGGCTCCAGAGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 40 | CAAGTGCAACTCGTTCAGTCCGGAGCAGAAGTCAAGAAACCTGGAGCTTCAGTCAAAGTCAGCTGCAAGGCCTCGGGCTTCAATATCAAGGACGTCTACATGTCCTGGGTGCGGCAGGCTCCAGAGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 83 | CAAGTGCAACTCGTTCAGTCCGGAGCAGAAGTCAAGAAACCTGGAGCTTCAGTCAAAGTCAGCTGCAAGGCCTCGGGCTTCAATATCAAGGACGCTTACATGTCCTGGGTGCGGCAGGCTCCAGGGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 41 | CAAGTGCAACTCGTTCAGTCCGGAGCAGAAGTCAAGAAACCTGGAGCTTCAGTCAAAGTCAGCTGCAAGGCCGGCTTCAATATCAAGGACACCTACATGTCCTGGGTGCGGCAGGCTCCAGAGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGGTCCTTGAGGTCGGATGACACTGCTGTGTATTACTGTGCCAGAGGCTGGGAAGGGTTCGCGTACTGGGGACAGGGAACTCTCGTGACTGTGTCGTCT |
| 42 | CAAGTGCAACTCGTTCAGTCCGGAGCAGAAGTCAAGAAACCTGGAGCTTCAGTCAAAGTCAGCTGCAAGGCCTCGGGCTTCAATATCAAGGACACCTACATGTCCTGGGTGCGGCAGGCTCCAGAGCAAGGACTGGAATGGATGGGGCGCATTGACCCGGAGAACGGTGATACGAAGTACGACCCGAAACTGCAGGGCCGCGTGACCATGACCGCAGATACTAGCACCAACACCGCGTACATGGAGCTGCGG |

TABLE 5-continued

Nucleic acid sequences of Table 4

| SEQ ID NO | Sequence |
|---|---|
|  | TCCTTGAGGTCGGATGACACTGCTGTGTATTACTGTGTCAGAGGCTGGGAAGGGTTCGCGTAC<br>TGGGGACAGGGAACTCTCGTGACTGTGTCGTCT |
| 86 | CAAGTGCAACTCGTTCAGTCCGGAGCAGAAGTCAAGAAACCTGGAGCTTCAGTCAAAGTCAGC<br>TGCAAGGCCTCGGGCTTAATATCAAGGACACCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTTCCAGAGGCTGGGAAGGGTTCGCGTAC<br>TGGGGACAGGGAACTCTCGTGACTGTGTCGTCT |
| 43 | CAAGTGCAACTCGTTCAGTCCGGAGCAGAAGTCAAGAAACCTGGAGCTTCAGTCAAAGTCAGC<br>TGCAAGGCCTCGTACTGGAATATCAAGGACACCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 44 | CAAGTGCAACTCGTTCAGTCCGGAGCAGAAGTCAAGAAACCTGGAGCTTCAGTCAAAGTCAGC<br>TGCAAGGCCTCGGGCTTAATATCCAGGACGTCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 45 | CAAGTGCAACTCGTTCAGTCCGGAGCAGAAGTCAAGAAACCTGGAGCTTCAGTCAAAGTCAGC<br>TGCAAGGCCTCGGGCTTAATATCTCGGACGTCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 46 | CAAGTGCAACTCGTTCAGTCCGGAGCAGAAGTCAAGAAACCTGGAGCTTCAGTCAAAGTCAGC<br>TGCAAGGCCTCGGCCTTAATATCAAGGACACCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 87 | CAAGTGCAACTCGTTCAGTCCGGAGCAGAAGTCAAGAAACCTGGAGCTTCAGTCAAAGTCAGC<br>TGCAAGGCCTCGGCCTTAATATCAAGGACGTCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 88 | CAAGTGCAACTCGTTCAGTCCGGAGCAGAAGTCAAGAAACCTGGAGCTTCAGTCAAAGTCAGC<br>TGCAAGGCCTCGGGCTTAATATCAAGGACGTCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTAGCAGAGGCTGGGAAGGGTTCGCGTAC<br>TGGGGACAGGGAACTCTCGTGACTGTGTCGTCT |
| 89 | CAAGTGCAACTCGTTCAGTCCGGAGCAGAAGTCAAGAAACCTGGAGCTTCAGTCAAAGTCAGC<br>TGCAAGGCCTCGGGCTTAATATCAAGGACGTCTACATGTCCTGGGTGCGGCAGGCTCCAGAG<br>CAAGGACTGGAATGGATGGGCGCATTGACCCGGAGAACGGTGATACGAAGTACGACCCGAAA<br>CTGCAGGGCCGCGTGACCATGACCGCAGATACTAGCACCAACACCGCGTACATGGAGCTGCGG<br>TCCTTGAGGTCGGATGACACTGCTGTGTATTACTGTGCCAGAGGCTGGGAAGGGTTCGCGTAC<br>TGGGGACAGGGAACTCTCGTGACTGTGTCGTCT |
| 47 | CAAGTCAAACTGCTGGAACAGTCCGGAGCAGAGCTGGTGAAGCCTGGAGCGTCGGTGCGGCTT<br>TCGTGTACCGCCTCCGGCTTTAACATCAAGGACACCTACATGTCGTGGGTGAAGCAGAGGCCC<br>GAGCAGGGGCTCGAATGGATTGGCCGCATCGACCCGGAAATTGGTGATACCAATACGACCCA<br>AAGTTCCAGGGAAAGGCCACTATCACTGCAGATACTTCAAGCAACACCGCCTACCTCCACCTG<br>TCCTCGCTCACTTCCGGAGATACCGCGGTCTACTATTGCTCAAGAGGATGGGAAGGCTTCGCG<br>TACTGGGGTCAAGGAACGTTGGTGACCGTCAGCGCC |
| 48 | GAATTGGTCATGACTCAGACGCCAGCTTCGCTGGCCGTGTCACTGGGACAGAGGGCCACTATC<br>AGCTGCAGAGCATCGGAGAATGTGGATAAGTACGGGAACAGCTTCATGCACTGGTATCAACAG<br>AAAGCTGGTCAACCTCCGAAGCTGCTTATCTACCGGGCGTCGGAACTCCAATGGGCATTCCA<br>GCACGGTTCAGCGGGTCGGGCTCCAGAACTGACTTCACCCTCACCATCAATCCCGTGGAGGCC<br>GATGACGTGGCGACCTACTTTTGTCAGCGCTCCAACGAGGTCCCGTGGACTTTCGGAGGAGGA<br>ACCAAGCTGGAAATCAAG |
| 49 | CAAGTCAAACTGCTGGAACAGTCCGGAGCAGAGCTGGTGAAGCCTGGAGCGTCGGTGCGGCTT<br>TCGTGTACCGCCGGCTTTAACATCAAGGACACCTACATGTCGTGGGTGAAGCAGAGGCCCGAG |

TABLE 5-continued

Nucleic acid sequences of Table 4

SEQ
ID NO    Sequence

CAGGGGCTCGAATGGATTGGCCGCATCGACCCGGAAAATGGTGATACCAAATACGACCCAAAG
         TTCCAGGGAAAGGCCACTATCACTGCAGATACTTCAAGCAACACCGCCTACCTCCACCTGTCC
         TCGCTCACTTCCGGAGATACCGCGGTCTACTATTGCTCAAGAGGATGGGAAGGCTTCGCGTAC
         TGGGGTCAAGGAACGTTGGTGACCGTCAGCGCC

TABLE 6

Additional amino acid sequences.

| Description | SEQ ID NO | Sequence |
|---|---|---|
| FW1 region of SEQ ID NO: 1 | 11 | QVQLVQSGAEVKKPGASVKVSCKAAGFNIK |
| FW2 region of SEQ ID NO: 80 | 84 | WVRQAPGQGLEWMG |
| FW2 region of SEQ ID NO: 1 | 85 | WVRQAPEQGLEWMG |
| EDIII-DV1 | 50 | MTLKGMSYVMCTGSFKLEKEVAETQHGTVLVQVKYE GTDAPCKlPFSTQDEKGATQNGRLITANPIVTDKEKPVN IEAEPPFGESYIVVGAGEKALKLSWFKKGSSIGK |
| EDIII-DV2 | 51 | MQLKGMSYSMCTGKFKVVKEIAETQHGTIVIRVQYEG DGSPCKIPFEIMDLEKRHVLGRLITVNPIVTEKDSPVNIE AEPPFGDSYIIIGVEPGQLKLNWFKKGSSLE |
| EDIII-DV3 | 52 | MKLKGMSYAMCLNTFVLKKEVSETQHGTILIKVEYKG EDAPCKITTSTEDGQGKAHNGRLITANPVVTKKEEPVNI EAEPPFGESNIVIGIGDKALKINWYRKGSSIGK |
| EDIII-DV4 | 53 | MRIKGMSYTMCSGKFSIDKEMAETQHGTTVVKVKYE GAGAPCKVPIEIRDVNKEKVVGRIISSTPLAENTNSVTNI ELEPPFGDSYIVIGVGNSALTHWFRKGSSIGK |
| EDIII sequences for testing breadth of binding | | |
| ED3-DV1/Viet08 | 54 | MTLKGMSYVMCTGSFKLEKELAETQHGTVLVQIKYEG TDAPCKITTSTQDEKGVTQNGRLITANPIVTDKEKPVNI EAEPPFGESYIVIGAGEKALKLSWFKKGSSIGK |
| ED3-DV1/Malaysia05 | 55 | MTLKGISYVMCTGPFKLEKEVAETQHGTVLVQVKYEG TDAPCKITTSSQDEKGVTQNGRLVTANPIVTDKEKPVNI EAEPPFGESYIVVGAGEKALKLSWFKKGSSIGK |
| ED3-DV1/Mexico07 | 56 | MTLKGTSYVMCTGSFKLEKEVAETQHGTVLVQVKYE GTDAPCKITTSTQDEKGVTQNGRLITANPIVTDKEKPVN IETEPPFGESYIVVGAGEKALKLSWFKKGSSIGK |
| ED3-DV2/Sing08 | 57 | MQLKGMSYSMCTGKFKVVKEIAETQHGTIVIRVQYEG DGSPCKIPFEIMDLEKRHVLGRLITVNPIVTEKDSPVNIE AEPPFGDSYIIIGVEPGQLKLSWFKKGSSIGQ |
| ED3-DV2/Venezuela07 | 58 | MQLKGMSYSMCTGKFKIVKEIAETQHGTIVIRIQYEGD GSPCKIPFEITDLEKRHVLGRLITVNPIVIEKDSPVNIEAE PPFGDSYIIIGVEPGQLKLNWFKKGSSIGQ |
| ED3-DV2/Peru95 | 59 | MQLKGMSYSMCTGKFKIVKEIAETQHGTIVIRVQYEGD GSPCKIPFEIMDLEKRHVLGRLITVNPIVIEKDSPVNIEA EPPFGDSYIIIGVEPGQLKLDWFKKGSSIGQ |
| ED3-DV2/Viet07 | 60 | MQLKGMSYSMCTGKFKVVKEIAETQHGTIVIRVQYEG DGSPCKIPFEIMDLEKRYVLGRLITVNPIVTEKDSPINIE AEPPFGDSYIIIGVEPGQLKLNWFKKGSSIGQ |
| ED3-DV3/Cambodia08 | 61 | MELKGMSYAMCLNTFVLKKEVSETQHGTILIKVEYKG EDAPCKITTSTEDGQGKAHSGRLITANPVVTKKEEPVNI EAEPPFGESNIVIGIGDKALKINWYKKGSSIGK |

TABLE 6-continued

Additional amino acid sequences.

| Description | SEQ ID NO | Sequence |
|---|---|---|
| ED3-DV3/Sing09 | 62 | MELKGMSYAMCQNAFVLKKEVSETQHGTILIKVEYKG EDAPCKITTSTEDGQGKAHNGRLITANPVVTKKEEPVNI EAEPPPFGESNIVIGIGDKALKINWYKKGSSIGK |
| ED3-DV3/Nicaragua10 | 63 | MELKGMSYAMCTNTFVLKKEVSETQHGTILIKVEYKG EDVPCKITTSTEDGQGKAHNGRLITANPVVTKKEEPVNI EAEPPPFGESNIVIGIGDNALKINWYKKGSSIGK |
| ED3-DV3/PuertoRico77 | 64 | MELKGMSYAMCSGTFVLKKEVSETQHGTILIKIEYKGE DAPCKIPFSTEDAQGKAHNGRLITANPVVTKKEEPVNIE AEPPPFGESNIVIGTGDKALRINWYKKGSSIGK |
| ED3-DV4/Venezuela08 | 65 | MRIKGMSYTMCSGKFSIDKEMAETQHGTTVVKVKYE GAGAPCKVPIEIRDVNKEKVVGRVISATPLAENTNSVT NIELEPPPFGDSYIVIGVGNSALTLHWFRKGSSIGK |
| ED3-DV4/Sing10 | 66 | MRIKGMSYTMCSGKFSIDKEMAETQHGTTVVKVKYE GAGAPCKVPIEIRDVNKEKVVGRIISSTPFAENTNSVTNI ELEPPPFGDSYIVIGVGDSALTLHWFRKGSSIGK |
| ED3-DV4/NewCal09 | 67 | MRIKGMSYTMCSGKFSIDKEMAETQHGTTVVKVKYE GAGAPCKIPIEIRDVNKEKVVGRIISSTPFAENTNSVINIE LEPPPFGDSYIVIGVGDSALTLHWFRKGSSIGK |
| ED3-DV4/Brazil11 | 68 | MRIKGMSYTMCSGKFSIDKEMAETQHGTTVVKIKYEG TGAPCKVPIEIRDVNKEKVVGRIISSTPFAENTNSVTNIE LEPPPFGDSYIVIGVGDSALTLHWFRKGSSIGK |
| ED3-DV4/Thai97 | 69 | MRIKGMSYTMCSGKFSIDREMAETQHGTTVVKVKYEG TGAPCKVPIEIRDVNKEKVVGRIISSTPFAESTNSVTNIE LEPPPFGDSYIVIGVGDSALTLHWFRKGSSIGK |
| ED3-DV4/H241/Phil56 | 70 | MRIKGMSYTMCSGKFSIDKEMAETQHGTTVVKVKYE GAGAPCKVPIEIRDVNKEKVVGRIISSTPFAEYTNSVTNI ELEPPPFGDSYIVIGVGDSALTLHWFRKGSSIGK |
| Human germline sequences, heavy chain | | |
| Human germline = VH1-69, JH4 | 71 | QVQLVQSGAEVKKPGSSVKVSCKASGGTFSSYAISWV RQAPGQGLEWMGGIIPIFGTANYAQKFQGRVTITADES TSTAYMELSSLRSEDTAVYYCARYFDYWGQGTLVTVS S |
| Human germline = VH1-18, JH6 | 72 | QVQLVQSGAEVKKPGASVKVSCKASGYTFTSYGISWV RQAPGQGLEWMGWISAYNGNTNYAQKLQGRVTMTT DTSTSTAYMELRSLRSDDTAVYYCARYMDVWGKGTT VTVSS |
| Human germline = VH1-18, JH4 | 73 | QVQLVQSGAEVKKPGASVKVSCKASGYTFTSYGISWV RQAPGQGLEWMGWISAYNGNTNYAQKLQGRVTMTT DTSTSTAYMELRSLRSDDTAVYYCARYMDVWGQGTL VTVSS |
| Human germline = VH5-a*04, JH4 | 74 | EVQLVQSGAEVKKPGESLRISCKGSGYSFTSYWISWVR QMPGKGLEWMGRIDPSDSYTNYSPSFQGQVTISADKSI STAYLQWSSLKASDTAMYYCARYMDVWGQGTLVTV SS |
| Human germline = VH1-46, JH4 | 75 | QVQLVQSGAEVKKPGASVKVSCKASGYTFNSYYMHW VRQAPGQGLEWMGIINPSGGSTSYAQKFQGRVTMTRD TSTSTVYMELSSLRSEDTAVYYCARYFDYWGQGTLVT VSS |
| Human germline sequences, light chain | | |
| Human Germline VK3D-11, Jk2 | 76 | EIVLTQSPATLSLSPGERATLSCRASQGVSSYLAWYQQ KPGQAPRLLIYDASNRATGIPARFSGSGPGTDFTLTISSL EPEDFAVYYCQQRSNWHCTFGQGTKLEIK |
| Human Germline VK1-39, Jk4 | 77 | DIQMTQSPSSLSASVGDRVTITCRASQSISSYLNWYQQK PGKAPKLLIYAASSLQSGVPSRFSGSGSGTDFTLTISSLQ PEDFATYYCQQSYSFGGGTKVEIK |

TABLE 6-continued

Additional amino acid sequences.

| Description | SEQ ID NO | Sequence |
|---|---|---|
| Human Germline VK4-1, Jk2 | 78 | DIVMTQSPDSLAVSLGERATINCKSSQSVLYSSNNKNY LAWYQQKPGQPPKLLIYWASTRESGVPDRFSGSGSGT DFTLTISSLQAEDVAVYYCQQYYSFGQGTKLEIK |
| Human Germline VK7-3 (pseudogene), Jk1 | 79 | DIVLTQSPASLAVSPGQRATITCRASESVSFLGINLIHWY QQKPGQPPKLLIYQASNKDTGVPARFSGSGSGTDFTLTI NPVEANDTANYYCLQSKNFPWTFGQGTKVEIK |

In some embodiments, the antibody molecule comprises a VH T33V mutation relative to A11. More specifically, in some embodiments, the anti-dengue antibody molecule comprises the CDR1 of the VH region of an antibody of Table 1 (e.g., D88, F38, F108, or C88), using the Kabat or Chothia definitions of CDRs. In some embodiments, the anti-dengue antibody molecule comprises the CDR1 and one or both of CDR2 and CDR3 of the VH region of an antibody of Table 1 (e.g., D88, A48, F38, F108, or C88), using the Kabat or Chothia definitions of CDRs. In some embodiments, the anti-dengue antibody molecule comprises CDR1 of the VH region of an antibody of Table 1 (e.g., D88, A48, F38, F108, or C88) in combination with another 1, 2, 3, 4, or 5 (e.g., collectively 6) CDRs found in a VH and/or VL region of Table 2, using the Kabat of Chothia definitions of CDRs. In some embodiments, the anti-dengue antibody molecule comprises the VH CDR1 of SEQ ID NO: 3. For instance, the anti-dengue antibody molecule may comprise the VH CDR1 of SEQ ID NO: 3 in combination with a VH CDR2 and/or VHCDR3 of Table 3, e.g., VH CDR2 of SEQ ID NO: 4 and VH CDR3 of SEQ ID NO: 5. As a further example, the anti-dengue antibody molecule may comprises the VH CDR1 of SEQ ID NO: 3 in combination with another 1, 2, 3, 4, or 5 (e.g., collectively 6) CDRs found in a VH and/or VL region of Table 2.

In certain embodiments, the antibody molecule comprises a VH F65L mutation relative to A11. In a Kabat-defined CDR of A11, position 65 is a CDR residue, while in a Chothia-defined CDR of A11, position 65 is a framework residue. In some embodiments, an antibody molecule's affinity for dengue virus is unaffected by the F65L mutation. In some embodiments, the anti-dengue antibody molecule comprises the CDR2 of the VH region of an antibody of Table 1 (e.g., D88, A48, F38, F108, or C88), using the Kabat or Chothia definitions of CDRs. In some embodiments, the anti-dengue antibody molecule comprises the CDR2 and one or both of CDR1 and CDR3 of the VH region of an antibody of Table 1 (e.g., D88, A48, F38, F108, or C88), using the Kabat or Chothia definitions of CDRs. In some embodiments, the anti-dengue antibody molecule comprises CDR2 of the VH region of an antibody of Table 1 (e.g., D88, A48, F38, F108, or C88) in combination with another 1, 2, 3, 4, or 5 (e.g., collectively 6) CDRs found in a VH and/or VL region of Table 2, using the Kabat of Chothia definitions of CDRs. In some embodiments, the anti-dengue antibody molecule comprises the VH CDR2 of SEQ ID NO: 4. For instance, the anti-dengue antibody molecule may comprise the VH CDR2 of SEQ ID NO: 4 in combination with a VH CDR1 and/or VH CDR3 of Table 3, e.g., VH CDR1 of SEQ ID NO: 3 and VH CDR3 of SEQ ID NO: 5. As a further example, the anti-dengue antibody molecule may comprises the VH CDR2 of SEQ ID NO: 4 in combination with another 1, 2, 3, 4, or 5 (e.g., collectively 6) CDRs found in a VH and/or VL region of Table 2. In certain embodiments, the antibody molecule comprises a VH F65L mutation and a VH T33V mutation relative to A11.

In some embodiments, the anti-dengue antibody molecule comprises a deletion of the S (del26) at position 26 in the VH relative to A11. In some embodiments, the antibody molecule comprises del26 mutation in combination with a VH T33V mutation and/or a VH F65L mutation. In certain embodiments, the antibody molecule comprises a del26 mutation and one or more CDRs of Table 3. In certain embodiments, the antibody molecule comprises a del26 mutation in combination with 1, 2, 3, 4, 5, or 6 CDRs, in a VH and/or VL region of Table 2, using the Kabat of Chothia definitions of CDRs.

As shown in Example 4 below, the N-terminus of the heavy chain is tolerant to mutations. Accordingly, in some embodiments, positions 1-6 of the heavy chain sequence have 1, 2, 3, 4, 5, or 6 mutations relative to an antibody of Table 1. In some embodiments, an antibody molecule has a substitution, insertion, or deletion at one or more (e.g., all) of residues 2, 3, 5, or 6 of a heavy chain sequence in Table 2. In certain embodiments, the antibody molecule comprises a portion of a heavy chain sequence of Table 2, e.g., amino acid positions 2-117, 3-117, 4-117, 5-117, 6-117, 8-117, or 10-117.

As shown in Example 5 below, positions 27 and 28 in the VH are tolerant of mutations, and in some embodiments, a mutation to position 27 and/or 28 enhances binding. Accordingly, in some embodiments, one or both of positions 27 and 28 have a mutation relative to an antibody of Table 1.

Example 5 also shows that position 98 in the VH is tolerant of mutations, and in some embodiments, a mutation to position 98 enhances binding. Accordingly, in some embodiments, position 98 has a mutation relative to an antibody of Table 1.

In some embodiments, the anti-dengue antibody molecule comprises a heavy chain constant region, a light chain constant region, and heavy and light chain variable regions of Table 2. In certain embodiments, the anti-dengue antibody molecule comprises a heavy chain constant region, a light chain constant region, and variable regions that comprise 1, 2, 3, 4, 5, or 6 CDRs of Table 3.

In some embodiments, the heavy chain variable region is a heavy chain variable region of Table 1, wherein residue 98 in the VH can be any amino acid. In certain embodiments, residue 98 can be any uncharged amino acid. In some embodiments, position 98 can be A, V, or S. Example 5 below shows that antibodies having residue A, V, or S at position 98 have good binding to EDIII.

During the humanization process, various framework regions (e.g., VH FW1) can be back-mutated to contain residues from mouse antibodies A11 or B11. More broadly, in some embodiments, the anti-dengue antibody molecule comprises the sequence of all or a portion of a VH region of Table 1. For instance, in some embodiments, the anti-dengue antibody molecule comprises amino acids 5-117, 10-117, 15-117, 20-117, 25-117, 30-117, or 32-117 of a VH region of Table 1. In some embodiments, the anti-dengue antibody molecule comprises a VH FW1 region selected from a mouse VH FW1 region (e.g., that found in A11 or B11) or a human VH FW1 region (e.g., one found in an antibody of Table 1 or a human germline VH FW1 sequence). In some embodiments, the VH FW1 region has no more than 1, 2, 3, or 4 positions of non-identity relative to amino acids 1-31 of a VH sequence of Table 1.

In some embodiments, the anti-dengue antibody molecule comprises a VH FW2 region of an antibody of Table 1. In some embodiments, the VH FW2 region has no more than 1, 2, 3, or 4 positions of non-identity relative to amino acids 37-50 of a VH sequence of Table 1. An antibody molecule capable of cross-reacting with EDIII from more than one serotype of dengue virus has several advantageous properties. For example, one therapy can be used to treat or diagnose multiple serotypes of dengue. In addition, a physician need not determine which serotype infected a patient in order to determine the appropriate therapy. Accordingly, in some embodiments, the anti-dengue antibody molecule is capable of independently binding to two, three, four, or more dengue virus serotypes with high affinity. For instance, the antibody molecule may independently bind with high affinity to EDIII of DV-1 and DV-2; of DV-1 and DV-3; of DV-1 and DV-4; of DV-2 and DV-3; of DV-2 and DV-4; of DV-3 and DV-4; or DV-1 and DV-2 and DV-3; of DV-1 and DV-2 and DV-4; of DV-1 and DV-3 and DV-4; of DV-2 and DV-3 and DV-4; or of DV-1 and DV-2 and DV-3 and DV-4. In certain embodiments, the antibody molecule can independently bind with high affinity to EDIII of DV-4 and EDIII of one or more other DV serotypes.

Each serotype of dengue virus mentioned above is a class containing numerous strains. The antibody molecules described herein show a good breadth of reactivity, binding to multiple strains within different serotypes (see FIG. 11). Accordingly, in some embodiments, an antibody molecule as described herein binds to and/or neutralizes one or more (e.g., at least 2, 3, 4, 5, 10, 15, or 20, 25, or 30 or more) dengue virus strains, e.g., strains selected from: DENV-4 BC2, DENV-4-Sing10, DENV-4 NewCa109, DENV-4 Phil56, DENV-3 Sing09, DENV-3 Nic10, DENV-3 H87, DENV-2 Peru95, DENV-2 Sing08, DENV-2 NGC, DENV-1 Hawaii/1944, DENV-2 New Guinea/1944 (NGC), DENV-3 Philippines/1956 (H87), DENV-4 Mexico/1997 (BC287/97), and DENV-4 H241, the strains listed in the phylogenetic tree of FIG. 10A, the strains shown in FIGS. 10B and 19-21, the strains listed in Table 6 herein (e.g., those strains for which EDIII sequences are provided in Table 6), the strains deposited in the ATCC, the strains listed in the World Reference Center for Emerging Viruses and Arboviruses (WRCEVA) (available at www.niaid.nih.gov/labsandresources/resources/dmid/wrceva/Pages/default.aspx), and the strains listed in the CDC's Division or Vector Borne Infectious Diseases (available at www2a.cdc.gov/nczved/dvbid/misc/reg.asp).

In some embodiments, the antibody molecule binds with high affinity to one or more of DV-1, DV-2, DV-3, and DV-4. An EDIII amino acid sequence of the E protein of each of these serotypes is, in some embodiments, an E protein sequence provided in Table 6.

In some embodiments, an antibody molecule disclosed herein does not activate antibody-dependent enhancement (ADE). ADE is described in more detail in Balsitis et al., Lethal Antibody Enhancement of Dengue Disease in Mice Is Prevented by Fc Modification, *PLoS Pathog* 6(2): e1000790. doi:10.1371/journal.ppat.1000790. Briefly, ADE describes a situation in which a person experiences two sequential dengue infections with dengue viruses of different serotypes, and the occurrence of the first infection makes the second infection more severe (e.g., more likely to progress into dengue hemorrhagic fever). A mechanism for ADE may be that an anti-dengue antibody binds simultaneously to the virus and to an antibody Fc receptor on a host cell, increasing infectivity. As is clear from the FRNT experiments disclosed herein, this application provides numerous antibody molecules that reduce, rather than increase, infectivity. Accordingly, in certain embodiments, an antibody molecule as described herein does not activate ADE in a patient. In some embodiments, the antibody inhibits ADE that is induced by other antibodies (e.g., the patient's endogenous antibodies).

In certain embodiments, the antibody molecule binds to a linear or conformational epitope on EDIII.

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibodies disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In some embodiments, the following definitions are used: AbM definition of CDR1 of the heavy chain variable domain and Kabat definitions for the other CDRs. In certain embodiments, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an E protein, or an epitope thereof. With respect to proteins (or protein mimetics), the antigen-binding region typically includes one or more loops (of at least, e.g., four amino acids or amino acid mimics) that form an interface that binds to the E protein. Typically, the antigen-binding region of an antibody molecule includes at least one or two CDRs, or more typically at least three, four, five or six CDRs.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al., Hybridoma, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In some embodiments, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In certain embodiments, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are also contemplated. Antibodies generated in a non-human organism, e.g., a rat or mouse, and then modified, e.g., in the variable framework or constant region, to decrease antigenicity in a human are also contemplated.

Chimeric antibodies can be produced by any suitable recombinant DNA technique. Several are known in the art (see Robinson et al., International Patent Publication PCT/US86/02269; Akira, et al., European Patent Application 184,187; Taniguchi, M., European Patent Application 171, 496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to EDIII. In some embodiments, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In some embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has effector function and can fix complement. In other embodiments the antibody does not recruit effector cells or fix complement. In certain embodiments, the antibody has reduced or no ability to bind an Fc receptor. For example, it may be an isotype or subtype, fragment or other mutant, which does not support binding to an Fc receptor, e.g., it has a mutagenized or deleted Fc receptor binding region.

The antibody constant region is altered in some embodiments. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In some embodiments, the only amino acids in the anti-dengue antibody molecule are canonical amino acids. In some embodiments, the anti-dengue antibody molecule comprises naturally-occurring amino acids; analogs, derivatives and congeners thereof; amino acid analogs having variant side chains; and/or all stereoisomers of any of any of the foregoing. The anti-dengue antibody molecule may comprise the D- or L-optical isomers of amino acids and peptidomimetics.

A polypeptide of an anti-dengue antibody molecule may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The anti-dengue antibody molecule can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-dengue antibody can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-dengue antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., immunomodulatory, immunostimularoty, cytotoxic, or cytostatic) agent or moiety. Radioactive isotopes can be used in diagnostic or therapeutic applications. Radioactive isotopes that can be coupled to the anti-dengue antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh) sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh) Radioisotopes useful as labels, e.g., for use in diagnostics, include iodine ($^{131}$I or $^{125}$I), indium ($^{111}$In) technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In some embodiments, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include anti-viral agents.

In some aspects, this disclosure provides a method of providing an antibody molecule disclosed herein. The method includes: providing an antigen, e.g., a dengue virus E protein or portion thereof; obtaining an antibody molecule that specifically binds to the antigen; evaluating efficacy of the antibody molecule in modulating activity of the antigen and/or organism expressing the antigen, e.g., dengue virus. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes but is not limited to RNA, genomic DNA and cDNA.

Animal Models

The antibody molecules described herein can be evaluated in an animal model. For example, an animal model can be used to test the efficacy of an antibody molecule described herein in reducing dengue viral infection, replication and/or transmission. Exemplary animal models that can be used for evaluating an antibody molecule described herein include, but are not limited to, AG129 mouse models (e.g., as described in Tharakaraman et al., *Proc Natl Acad Sci USA*. 2013; 110(17):E1555-64; Johnson et al. *J Virol*. 1999; 73(1): 783-6); non-mouse adapted mouse models (e.g., non-mouse adapted DENV-2 D2Y98P mouse model as described in Tan et al. *PLoS Negl Trop Dis*. 2010; 4(4):e672); humanized mouse models (e.g., as described in Sridharan et al. *J Virol*. 2013; 87(21):11648-58); non-human primate models (e.g., as described in Goncalvez et al. *Proc Natl Acad Sci USA*. 2007; 104(22):9422-7); and mosquito models (e.g., as described in Vu et al. *PLoS Negl Trop Dis*. 2010; 4(7):e757).

The AG129 mouse strain, which lacks both type-I and type-II interferon receptors, is an animal model that replicates certain disease manifestations observed in clinical cases of dengue, including viremia and other signs of disease (Tharakaraman et al., *Proc Natl Acad Sci USA*. 2013; 110(17):E1555-64; Johnson et al. *J Virol*. 1999; 73(1):783-6). This model is useful in evaluation of antiviral treatments and can also be used in proof of principle studies. Briefly, the AG129 (which is deficient in IFN-α/β and IFN-γ receptors) mouse is challenged with dengue virus, and a candidate therapeutic antibody molecule is administered. Typically, viremia (virus titer in a blood sample) is the endpoint of the experiment. Viremia can be measured, e.g., with quantitative RT-PCR. An exemplary AG129 mouse model is described in Example 10.

Non-mouse adapted mouse models can be generated, e.g., using a non-mouse adapted DEN2 virus strain (D2Y98P) that is highly infectious in AG129 mice upon intraperitoneal administration (Tan et al. *PLoS Negl Trop Dis*. 2010; 4(4): e672). Infection with a high dose of D2Y98P can induce cytokine storm, massive organ damage, and severe vascular leakage, leading to haemorrhage and rapid death of the animals at the peak of viremia. Infection with a low dose of D2Y98P can lead to asymptomatic viral dissemination and replication in relevant organs, followed by non-paralytic death of the animals few days after virus clearance, similar to the disease kinetic in humans. Spleen damage, liver dysfunction and increased vascular permeability, but no hemorrhage, can be observed in moribund animals, suggesting intact vascular integrity, a cardinal feature in dengue shock syndrome.

Humanized mouse models can be generated, e.g., by adoptive transfer of human CD34$^+$ fetal liver cells into NOD-scid Il2rg$^{-/-}$ (NSG) mice that develop significant levels of human platelets, monocytes/macrophages, and hepatocytes (Sridharan et al. *J Virol*. 2013; 87(21):11648-58). Infection of these mice with dengue virus such as DENV serotype 2 (DENV-2) can recapture certain characteristic features of dengue viral infection in humans, e.g., transient leukopenia and thrombocytopenia.

Non-human primate models can be generated, e.g., in juvenile rhesus monkeys after DENV challenge, as described in Goncalvez et al. *Proc Natl Acad Sci USA*. 2007; 104(22):9422-7. The viremia titers of infected monkeys can be determined, e.g., by quantitative PCR or Focus Forming Units (FFU) assay.

Mosquito models can also be used to evaluate inhibitory activity of antibodies against dengue virus, e.g., neutralization of viral infection or reduction of transmission between infected subjects and mosquitoes. Dengue virus is a mosquito transmitted RNA virus. Certain dengue virus can develop in vivo fitness advantage, which may result in higher probability of human-to-mosquito transmission (Vu et al., *PLoS Negl Trop Dis*. 2010; 4(7):e757). To establish a mosquito model, blood containing virus and antibody can be fed to mosquitoes. Viral load in mosquitoes' abdomens can be measured by qRT-PCR. An exemplary mosquito model is described in Example 13.

Pharmaceutical Compositions and Kits

In some aspects, this disclosure provides compositions, e.g., pharmaceutically acceptable compositions, which include an anti-dengue antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In some embodiments, the level of antibody aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods. Several are known in the art, and for many therapeutic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic compositions can also be administered with medical devices, and several are known in the art.

Dosage regimens are adjusted to provide the desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic effect to be achieved, and (b) the limitations inherent in the art of compounding such an antibody molecule for the treatment of sensitivity in individuals.

An exemplary, non-limiting range for a therapeutically or prophylactically effective amount of an antibody molecule is 0.1-20 mg/kg, more preferably 1-10 mg/kg. The antibody molecule can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount" or a "prophylactically effective amount" of an antibody molecule. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the antibody molecule is outweighed by the therapeutically beneficial effects. A "therapeutically effective dosage" preferably inhibits a measurable parameter by at least about 20%, more preferably by at least about 40%, even more preferably by at least about 60%, and still more preferably by at least about 80% relative to untreated subjects. The measurable parameter may be, e.g., viral load, fever, headache, muscle or joint pains, skin rash, bleeding, reduced platelet levels, and reduced blood pressure. The ability of an antibody molecule to inhibit a measurable parameter can be evaluated in an animal model system predictive of efficacy in dengue fever. Alternatively, this property of a composition can be evaluated by examining the ability of the antibody molecule to neutralize dengue virus, e.g., by assaying focus formation in vitro.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within this disclosure is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject.

Nucleic Acids

The present disclosure also features nucleic acids comprising nucleotide sequences that encode heavy and light chain variable regions and CDRs of the anti-dengue antibody molecules, as described herein. For example, the present disclosure features a first and second nucleic acid encoding heavy and light chain variable regions, respectively, of an anti-dengue antibody molecule chosen from one or more of the antibody molecules disclosed herein, e.g., an antibody of Table 1, or a portion of an antibody, e.g., the variable regions of Table 2. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in Table 5 herein, a sequence substantially homologous thereto (e.g., a sequence at least about 85%, 90%, 95%, 99% or more identical thereto, and/or capable of hybridizing under the stringency conditions described herein). In some embodiments, the nucleic acid can comprise a nucleotide sequence encoding at least one, two, or three CDRs from a light chain variable region having the nucleotide sequence as set forth in Table 5 herein, or a sequence substantially homologous thereto (e.g., a sequence at least about 85%, 90%, 95%, 99% or more identical thereto, and/or capable of hybridizing under the stringency conditions described herein). In certain embodiments, the nucleic acid can comprise a nucleotide sequence encoding at least one, two, three, four, five, or six CDRs from heavy and light chain variable regions having the nucleotide sequence as set forth in Table 5 herein, or a sequence substantially homologous thereto (e.g., a sequence at least about 85%, 90%, 95%, 99% or more identical thereto, and/or capable of hybridizing under the stringency conditions described herein).

In certain embodiments, the nucleic acid comprises a nucleotide sequence as set forth in Table 5 herein or a sequence substantially homologous thereto (e.g., a sequence at least about 85%, 90%, 95%, 99% or more identical thereto, and/or capable of hybridizing under the stringency conditions described herein). In some embodiments, the nucleic acid comprises a portion of a nucleotide sequence as set forth in Table 5 herein or a sequence substantially homologous thereto (e.g., a sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

In some aspects, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In some embodiments, the vectors comprise nucleotides encoding an antibody molecule described herein. In some embodiments, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The present disclosure also provides host cells comprising a nucleic acid encoding an antibody molecule as described herein. For example, the host cells may comprise a nucleic acid of Table 5, a sequence substantially homologous thereto (e.g., a sequence at least about 85%, 90%, 95%, 99% or more identical thereto, and/or capable of hybridizing under the stringency conditions described herein), or a portion of one of said nucleic acids. Additionally, the host cells may comprise a nucleic acid encoding an amino acid sequence of Table 2 or Table 3, a sequence substantially homologous thereto (e.g., a sequence at least about 85%, 90%, 95%, 99% or more identical thereto), or a portion of one of said sequences.

In some embodiments, the host cells are genetically engineered to comprise nucleic acids encoding the antibody molecule.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses of Anti-Dengue Antibody Molecules

The antibody molecules disclosed herein have in vitro and in vivo diagnostic, as well as therapeutic and prophylactic utilities. In some embodiments, the antibody molecules neutralize dengue virus. For example, these molecules can be administered to cells in culture, in vitro or ex vivo, or to a subject, e.g., a human subject, e.g., in vivo, to neutralize dengue virus. Accordingly, in some aspects, the disclosure provides a method of treating a dengue virus infection in a subject, comprising administering to the subject an antibody molecule described herein, such that the dengue virus infection is treated. For example, these antibody molecules can be administered to cells in culture, e.g. in vitro or ex vivo, or in a subject, e.g., in vivo, to treat, prevent, and/or diagnose a dengue virus infection.

As used herein, the term "subject" is intended to include human and non-human animals. In some embodiments, the subject is a human subject, e.g., a human patient infected with dengue virus or at risk of being infected with dengue virus. The term "non-human animals" includes mammals and non-mammals, such as non-human primates. In some embodiments, the subject is a human. The methods and compositions described herein are suitable for treating human patients infected with dengue virus. Patients infected with dengue virus include those who have been exposed to the virus but are (at least temporarily) asymptomatic, patients having dengue fever, patients having dengue hemorrhagic fever, and patients having dengue shock syndrome.

Methods of Treating Dengue Virus

Dengue virus displays an E (envelope) protein on the viral surface. The E protein contributes to the attachment of the virus to a host cell. The E protein comprises a DI domain (a nine-stranded beta-barrel) a DII domain (a hydrophobic domain implicated in fusion with the host cell), and a DIII domain (an extracellular domain). While not wishing to be bound by theory, in some embodiments, the antibody molecules described herein can neutralize dengue virus by binding to its E protein DIII (EDIII) domain, e.g., by preventing the virus from fusing with a host cell, preventing the virus from binding to a host cell, disrupting the structure of the E protein, or destabilizing the virus.

Dengue fever is an infectious disease, usually mosquito-borne, caused by the dengue virus. The initial infection is often followed by a brief asymptomatic period, usually 4-7 days. Sometimes an infected patient does not develop any symptoms of dengue fever. However, in patients that manifest dengue fever, the characteristic symptoms are sudden-onset fever (sometimes over 40° C.), headache, muscle and joint pains, and rash. During the febrile phase of infection, fever, pain, and headache manifest. In some patients the febrile phase is followed by the critical phase (associated with dengue shock syndrome and dengue hemorrhagic fever), in which patients may suffer from fluid accumulation in the chest and abdominal cavity, depletion of fluid from circulation, an inadequate supply of blood to the vital organs, and bleeding. This is followed by a recovery phase. In some embodiments, the antibody molecules herein are administered to a patient in the asymptomatic period, the febrile phase, the critical phase, and/or the recovery phase.

Dengue virus is typically diagnosed based on a physical exam and the patient's reported symptoms. A probable diagnosis can be made when a patient displays a fever and at least two symptoms selected from nausea/vomiting, rash, generalized pain, reduced white blood cell levels, or positive tourniquet test. Additional tests that indicate dengue fever include a test for reduced white blood cell count, low platelet levels, metabolic acidosis, elevated level of aminotransferase from the liver, hemoconcentration, hypoalbuminemia, detection of fluid by ultrasound (suggests dengue shock syndrome), a pulse pressure below 20 mm Hg (indicates dengue shock syndrome), delayed capillary refill (indicates peripheral vascular collapse). Accordingly, in some embodiments the antibody molecules are administered to a patient that satisfies the aforementioned criteria.

Certain antibody molecules described herein are capable of treating at least two, three, or four serotypes of dengue virus. Accordingly, in certain embodiments, the antibody molecule is administered to a patient infected with or with a risk of being infected with dengue virus, when no test has been performed to determine the serotype of the dengue virus, e.g., the serotype of the dengue virus may be unknown. In some embodiments, the dengue virus is of serotype DV-1, DV-2, DV-3, or DV-4.

The antibody molecules are typically administered at a frequency that keeps a therapeutically effective level of antibodies in the patient's system until the patient recovers. For example, the antibody molecules may be administered at a frequency that achieves a serum concentration sufficient for at least about 1, 2, 5, 10, 20, 30, or 40 antibodies to bind each virion. In some embodiments, the antibody molecules are administered every 1, 2, 3, 4, 5, 6, or 7 days.

Methods of administering various antibody molecules are known in the art and are described below. Suitable dosages of the antibody molecules used will depend on the age and weight of the subject and the particular drug used.

The antibody molecules can be used by themselves or conjugated to a second agent, e.g., an antiviral agent, toxin, or protein, e.g., a second anti-dengue antibody. This method includes: administering the antibody molecule, alone or conjugated to a second agent, to a subject requiring such treatment. The antibody molecules can be used to deliver a variety of therapeutic agents, e.g., a toxin or anti-viral agent, or mixtures thereof.

Combination Therapies

The anti-dengue antibody molecules can be used in combination with other therapies. For example, the combination therapy can include an anti-dengue antibody molecule co-formulated with, and/or co-administered with, one or more additional therapeutic agents, e.g., anti-viral agents (including other anti-dengue antibodies), vaccines (including dengue virus vaccines), or agents that enhance an immune response. In other embodiments, the antibody molecules are administered in combination with other therapeutic treatment modalities, such as intravenous hydration, fever-reducing agents (such as acetaminophen), or blood transfusion. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with the disease. In one embodiment, two or more treatments are delivered prophylactically, e.g., before the subject is infected or diagnosed with dengue virus. In another embodiment, the two or more treatments are delivered after the subject has been diagnosed with the dengue virus. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The anti-viral agent may be, e.g., balapiravir, chloroquine, celgosivir, ivermectin, or *Carica folia*.

The vaccine may be, e.g., live, attenuated, recombinant dengue serotypes 1, 2, 3, and 4 virus (e.g., clinical trial NCT01488890 by Sanofi Pasteur); CYD Tetravalent Dengue Vaccine (e.g., clinical trial NCT01943825, by Sanofi Pasteur), Chimeric dengue serotype (1, 2, 3, 4) (e.g., clinical trial NCT00730288 by Sanofi), CYD Dengue Vaccine (e.g., clinical trial NCT00993447 by Sanofi), tetravalent live attenuated dengue vaccine (e.g., clinical trial NCT00322049 by GlaxoSmithKline), Tetravalent Dengue Vaccine (TVDV) (e.g., clinical trial NCT01502358 by U.S. Army Medical Research and Materiel Command), Chimeric tetravalent dengue (serotype 1, 2, 3, 4) (e.g., clinical trial NCT00842530 by Sanofi Pasteur), dengue lyophilized vaccine (e.g., clinical trial NCT01696422 by Butantan Institute), ChimeriVax™ Tetravalent Dengue Vaccine (e.g., clinical trial NCT00617344 by Sanofi), Bivalent CYD-1,3 Dengue (Vero) (e.g., clinical trial NCT00740155 by Sanofi Pasteur), Bivalent CYD-2,4 Dengue (Vero) (e.g., clinical trial NCT00740155 by Sanofi Pasteur), Tetravalent blending VDV-2/CYD-1,3,4 Dengue (Vero) (e.g., clinical trial NCT00740155 by Sanofi Pasteur), Tetravalent CYD-1,2,3,4 Dengue (Vero) (e.g., clinical trial NCT00740155 by Sanofi Pasteur), rDEN1delta30 or rDEN2/4delta30(ME) (e.g., clinical trial NCT00458120 by National Institute of Allergy and Infectious Diseases), Modified Live Tetravalent Chimeric Dengue Vaccine (SC or ID) (e.g., clinical trial NCT01110551 by National Institute of Allergy and Infectious Diseases), Dengue vaccine (e.g., clinical trial NCT00384670 by United States Army Medical Materiel Development Activity), Investigational Vaccine for Dengue Virus Subtype 2 (e.g., NCT01073306 by National Institute of Allergy and Infectious Diseases), F17 (e.g., NCT01843621 by U.S. Army Medical Research and Materiel Command), Post-Transfection F17 or Post-Transfection F19 (e.g., clinical trial NCT00468858 by U.S. Army Medical Research and Materiel Command), DENVax (e.g., clinical trial NCT01511250 by Inviragen Inc.), DIME (dengue-1 premembrane/envelope DNA vaccine) (e.g., clinical trial NCT00290147 by U.S. Army Office of the Surgeon General), Investigational Vaccine for DEN1 (e.g., clinical trial NCT01084291 by National Institute of Allergy and Infectious Diseases), Live attenuated tetravalent dengue vaccine (e.g., clinical trial NCT00350337 by Walter Reed Army Institute of Research), rDEN4delta30-200,201 (e.g., clinical trial NCT00270699 by National Institute of Allergy and Infectious Diseases), TetraVax-DV-TV003 or rDEN2430-7169 (e.g., clinical trial NCT02021968 by National Institute of Allergy and Infectious Diseases), TetraVax-DV, optionally in admixture (e.g., clinical trial NCT01436422 by National Institute of Allergy and Infectious Diseases), DEN4 Vaccine Candidate (e.g., clinical trial NCT00919178 by National Institute of Allergy and Infectious Diseases), rDEN4delta30-4995 (e.g., clinical trial NCT00322946 by National Institute of Allergy and Infectious Diseases), rDEN3delta30/31-7164 (e.g., clinical trial NCT00831012 by National Institute of Allergy and Infectious Diseases), TDENV-PIV (e.g., clinical trial NCT01702857 by U.S. Army Medical Research and Materiel Command), DENV-1 PIV (e.g., clinical trial NCT01502735 by U.S. Army Medical Research and Materiel Command), rDEN3-3'D4delta30 (e.g., clinical trial NCT00712803 by National Institute of Allergy and Infectious Diseases), V180 (e.g., clinical trial NCT01477580 by Merck Sharp & Dohme Corp.), or DEN1-80E (e.g., clinical trial NCT00936429 by Hawaii Biotech, Inc.).

The other therapy may be, for example, hypertonic sodium lactate, activated recombinant human factor VII, or anti-d (e.g., clinical trial NCT01443247 by Postgraduate Institute of Medical Education and Research).

In certain embodiments, the additional antiviral agent is a second anti-dengue antibody molecule, e.g., an anti-dengue antibody molecule different from a first anti-dengue antibody molecule. Exemplary anti-dengue antibody molecules that can be used in combination include, but are not limited to, any combination of the antibodies listed in Table 1 (for example, any combination of two of more of D88, F38, A48, C88, F108, B48, A68, A100, C58, C78, C68, D98, A11 (also known as monoclonal antibody 4E5A (Tharakaraman et al., *Proc Natl Acad Sci USA*. 2013; 110(17):E1555-64)) or B11;

monoclonal antibody 4E11 (Thullier et al., *J Biotechnol.* 1999; 69(2-3):183-90); human antibody 14c10 (HM14c10) (Teoh et al. *Sci Transl Med.* 2012 Jun. 20; 4(139):139ra83); human monoclonal antibodies 1F4, 2D22, and 5J7 (de Alwis et al., *Proc Natl Acad Sci USA.* 2012; 109(19):7439-44); human monoclonal antibodies DV1.1, DV1.6, DV3.7, DV4.4, DV5.1, DV6.1, DV7.5, DV8.1, DV10.16, DV13.4, DV13.8, DV14.5, DV14.5, DV15.7, DV16.5, DV16.8, DV17.6, DV18.21, DV18.4, DV19.3, DV20.1, DV21.1, DV21.5, DV22.3, DV22.3 LALA, DV23.13, DV25.5, DV27.2, DV28.1, DV28.8, DV34.4, DV35.3, DV38.1, DV51.6, DV52.1, DV53.4, DV54.7, DV55.1, DV56.12, DV54.7, DV57.4, DV59.3, DV60.3, DV61.2, DV62.5, DV63.1, DV64.3, DV65.5, DV66.1, DV67.9, DV68.2, DV69.6, DV70.1, DV71.1, DV74.4, DV75.9, DV76.5, DV77.5, DV78.6, DV79.3, DV82.11, DV82.11 LALA, DV86.2, DV87.1, DV87.1 LALA, DV90.3, DV257.13, DV291.7, DV415.8, and DV470.12 (Beltramello et al., *Cell Host Microbe.* 2010; 8(3):271-83); human monoclonal antibodies 3-147, 58/5, 2F5, 2G4, 5F9, and 135.3 (Dejnirattisai et al., *Science.* 2010; 328(5979):745-8); mAb 2H12 (Midgley et al. *J Immunol.* 2012; 188(10):4971-9); humanized monoclonal antibody 1A5 (Goncalvez et al., *Proc Natl Acad Sci USA.* 2007; 104(22):9422-7); and human monoclonal antibody 1C19 (Smith et al., *MBio.* 2013; 4(6):e00873-13); or any of the antibodies disclosed in: WO 05/056600 by Lai, C. and Purcell, R. (e.g., antibodies 1A5 and 5H2; WO2010/043977 by Lanzavecchia, A. et al.; WO2013/173348 by Dimitrov et al.; US2013/0259871 by Macary et al.; WO 2013/089647 by Fink et al.; WO 2013/035345 by Setthapramote et al.; U.S. Pat. No. 8,637,035 by Han-Chung Wu et al.; or WO 2014/025546 by Sasisekharan, R. et al.; or a derivative of any of the aforesaid antibodies (e.g., a human or humanized form thereof).

Other therapeutic agents that can be used in combination with an anti-dengue antibody described herein also include, but are not limited to, for example, alpha-glucosidase I inhibitors (e.g., celgosivir as described in Rathore et al., *Antiviral Res.* 2011; 92(3):453-60); adenosine nucleoside inhibitors (e.g., NITD008 as described in Yin et al., *Proc Natl Acad Sci USA.* 2009; 106(48):20435-9); inhibitors of NS3 and/or its cofactor NS2B (e.g., compounds that block the NS2B binding pocket within NS3, e.g., [5-amino-1-(phenyl)sulfonyl-pyrazol-3-yl] compounds, as described in Lescar et al., *Antiviral Res.* 2008; 80(2):94-101); RNA-dependent RNA polymerase (RdRp) inhibitors (e.g., NITD107 as described in Noble et al., *J Virol.* 2013; 87(9):5291-5); inhibitors of host pyrimidine biosynthesis, e.g., host dihydroorotate dehydrogenase (DHODH) (e.g., NITD-982 and brequinar as described in Wang et al., *J Virol.* 2011; 85(13):6548-56); inhibitors of viral NS4B protein (e.g., NITD-618 as described in Xie et al., *J Virol.* 2011; 85(21):11183-95); and iminosugars (e.g., UV-4 as described in Perry et al., *Antiviral Res.* 2013; 98(1):35-43).

Methods of Diagnosis

In some aspects, the present disclosure provides a diagnostic method for detecting the presence of a dengue virus E protein in vitro (e.g., in a biological sample, such as a blood sample) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma or blood) or a control subject with an antibody molecule described herein; and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of dengue virus in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids such as blood, or tissue samples.

Complex formation between the antibody molecule and a dengue virus protein can be detected by measuring or visualizing either the antibody molecule bound to the dengue virus protein or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of a dengue virus protein can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of a dengue virus protein in the sample is inversely proportional to the amount of labeled standard bound to the antibody molecule.

EXAMPLES

Example 1: Structure-Guided Design of Anti-Dengue Antibodies

Epitope and Template Identification

Various neutralizing epitopes exist in dengue virus E protein dimer. These epitopes include regions, e.g., in EDI, EDII, EDIII, fusion loop, EDI/II hinge, and the EDIII "A" β-strand. EDI and EDII are immunodominant in humans and can induce weakly neutralizing but highly cross-reactive antibodies. EDIII can induce potent neutralizing antibodies. Antibodies directed against the fusion loop, located in EDII, often exhibit cross-serotype reactivity but weak neutralizing activity. Antibodies directed against the EDI/II hinge region can exhibit potent neutralization but are typically serotype-specific due to low conservation of the epitope region. Antibodies directed against the EDIII A-strand often exhibit high potency due in part to the greater accessibility of this region to antibodies, but often have limited cross-serotype reactivity.

To engineer a broadly reactive and highly potent neutralizing antibody to dengue virus, mouse mAb 4E11 was identified as a template antibody, as it binds to the EDIII A-strand epitope region and exhibits strong neutralization to DENV-1, DENV-2, and DENV-3 but not DENV-4. 4E11 has very low (µM) binding to DENV-4. An approach was utilized to increase molecular contacts of 4E11 to DENV-4 in order to increase affinity and thereby neutralization potency to DENV-4. To do this, a structural model of 4E11 with EDIII was generated and then analyzed to identify serotype-specific binding determinants of 4E11.

Technology and Tool Development

Conventional computational approaches for protein engineering typically rely on energetic-based methods. Results from these methods are generally highly sensitive to the precise atom locations in a structure or model, and therefore these methods typically require a crystal structure or similar data of high-resolution and quality of the protein-protein complex for accurate modeling and beneficial-mutation predictions. Additionally, conventional energetics-based approaches to protein engineering typically do not incorporate antibody-specific properties and knowledge.

A different approach is to use empirical informatics, and specifically residue pairwise propensity methods (Tharakaraman K. et al. (2013) *Proc Natl Acad Sci USA.* 23; 110(17):E1555-64). Engineering of a broadly cross-reactive antibody to dengue virus with broad-spectrum activity and increased in vivo potency was performed by evaluating the pairwise propensity ("fitness") for paratope residues given the epitope environment. This fitness metric is based on empirical data of antibody-antigen structures and is less sensitive to precise atom locations as compared to other approaches. Thus, this approach can be effectively used to enhance accuracy of antibody-antigen computational molecular docking and to augment prediction of affinity-enhancing mutations and identification of positions for affinity maturation.
Application: Engineer Template mAb for pM-nM Binding to all Four DENY Serotypes A 4E11-EDIII structural model was generated and affinity-enhancing mutations/positions were predicted. For example, individual mutations were predicted at specific sites and positions were selected for the creation of rational, focused combinatorial libraries. As shown in FIG. 23, the resulting humanized antibody D88 demonstrates, relative to antibody 4E11, a 10,000-fold affinity gain to DENV-4 with concurrent improved affinity to DENV1-3.
Comparison of mAb A11 with mAb 4E11

A comparison between anti-dengue antibodies 4E11 (which antibody is described in Thullier et al., *J Biotechnol.* 1999 Apr. 15; 69(2-3):183-90) and A11 (4E5A) is provided in Tharakaraman et al., *Proc Natl Acad Sci USA.* 2013; 110(17):E1555-64. 4E5A has five point mutations relative to 4E11, at A55E (VH), R31K (VL), N57E (VL), E59Q (VL), and S60W (VL) (Tharakaraman et al., 2013, *Proc Natl Acad Sci USA.* 2013; 110(17):E1555-64).

Example 2. Del26 Improves DV-4 Neutralization Activity

B11 is an anti-dengue antibody with a heavy chain deletion of S26 in framework 1 (FR1) relative to A11 (4E5A). 4G2 is a control anti-dengue antibody. The neutralization activity of each antibody for EDIII from four dengue virus serotypes was tested by a Focus Reduction Neutralization test (FRNT).

The focus reduction neutralization test detects foci formed when dengue virus infects host Vero cells. Briefly, dilutions of antibody are mixed with an equal volume of diluted virus, and the mixture is transferred to Vero cell monolayers, and foci are detected. Data are expressed as the relative infectivity. The FRNT50 represents the concentration of antibody required to achieve 50% virus neutralization. A more detailed protocol for the focus neutralization reduction test can be found in Tharakaraman et al., 2013, *Proc Natl Acad Sci USA.* 2013; 110(17):E1555-64.

Figure 3:
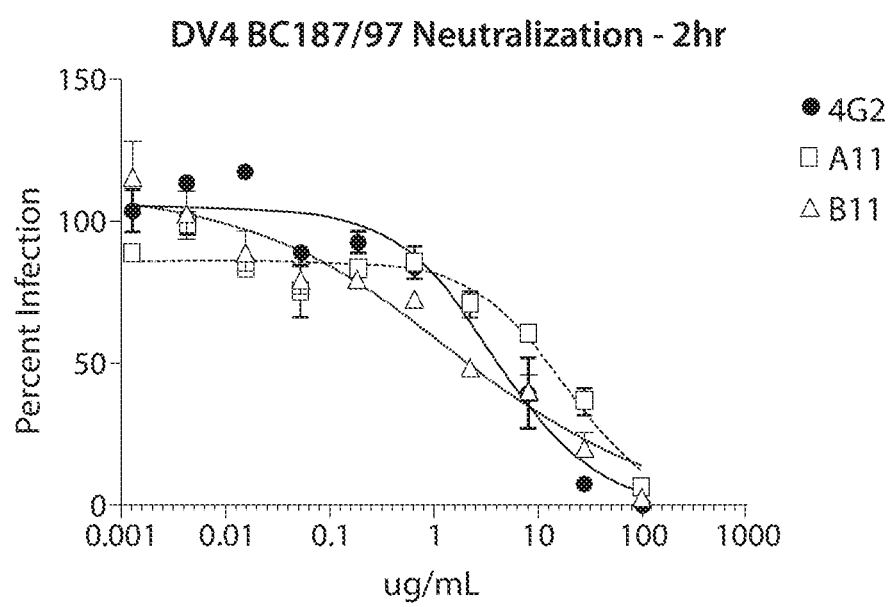
FIG. 3 shows a repeated assay of antibodies A11 and B11 neutralizing DV4.
Figure 10A:
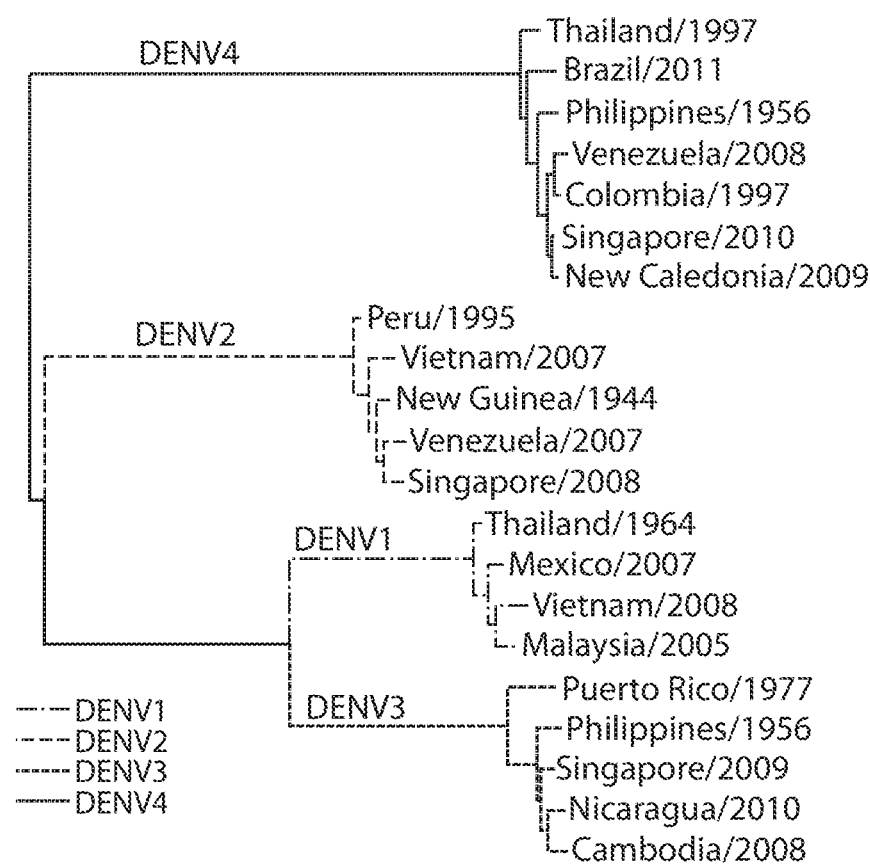
FIG. 10A summarizes the phylogenetic relationship of the EDIII amino acid sequences of selected dengue virus isolates. "DENV" is an abbreviation for dengue virus, and DENV-2 represents serotype DV-2, DENV-3 represents serotype DV-3, and DENV-4 represents serotype DV-4.
Figure 12:
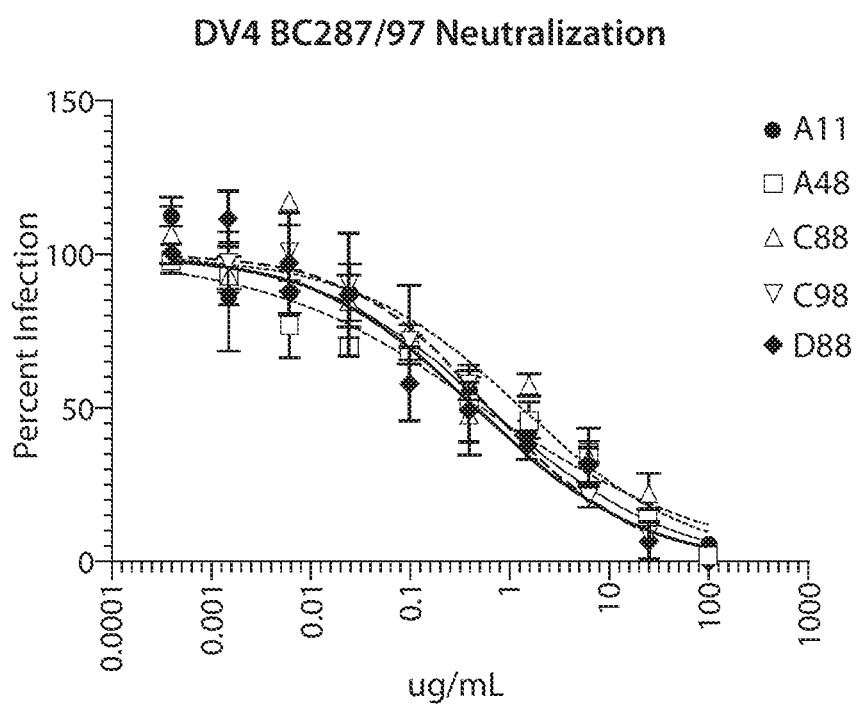
FIG. 12 shows the ability of several anti-dengue antibodies to neutralize dengue virus serotype DV-4 in a focus reduction neutralization test.
Figure 13:
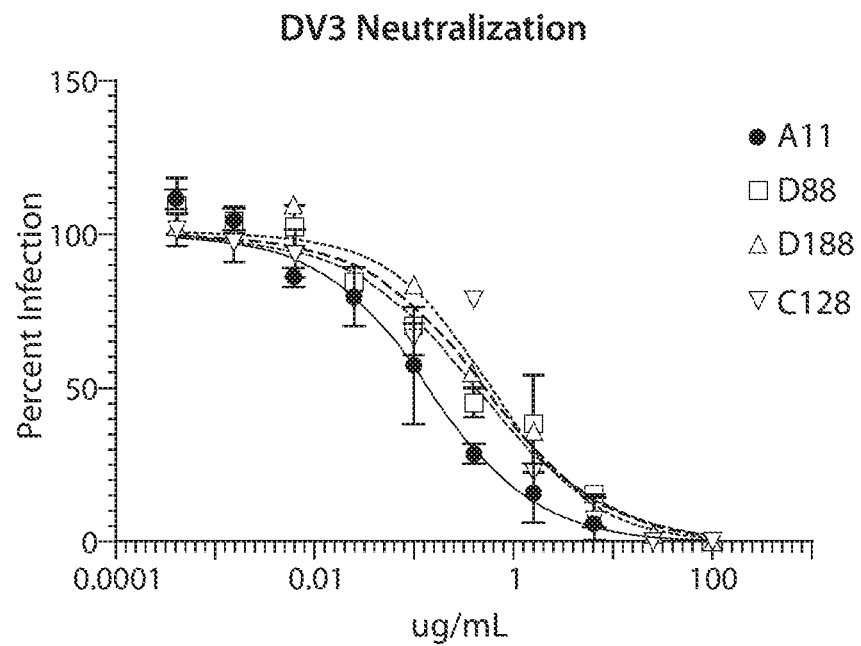
FIG. 13 shows the ability of several anti-dengue antibodies to neutralize dengue virus serotype DV-3 in a focus reduction neutralization test. DV-3 H87 was used in this test.
Figure 14:
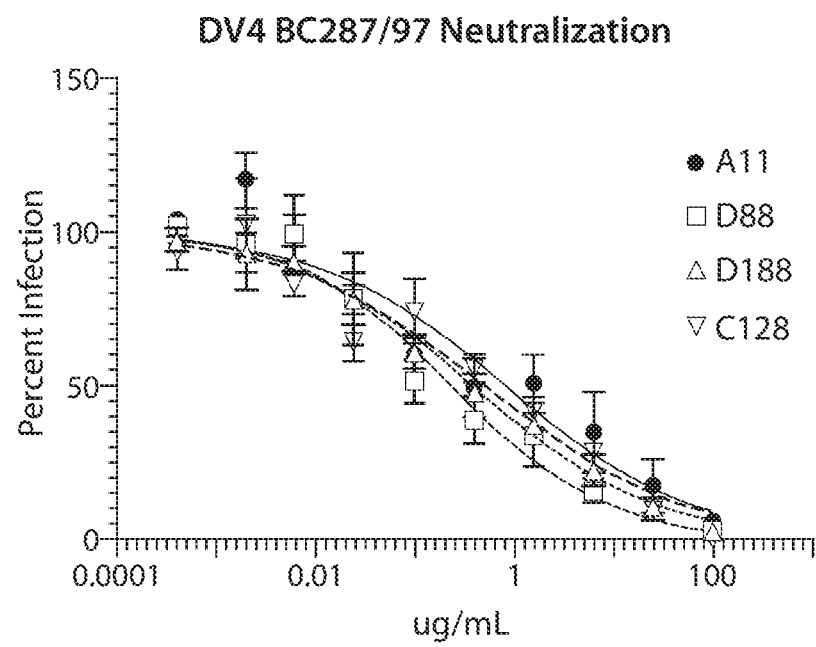
FIG. 14 shows the ability of several anti-dengue antibodies to neutralize dengue virus serotype DV-4 in a focus reduction neutralization test.

The four graph panels of FIG. 2 show the neutralization activities of each antibody against representative strains from dengue virus serotypes. FIG. 3 is a repeated assay of each antibody against dengue virus serotype DV-4. The results are summarized in the table at the bottom of FIG. 2, which shows the IC50 of each antibody against the virus (in μg/ml).

Unexpectedly, the deletion of one amino acid in the framework 1 region confers improved DV-4 neutralization activity on B11. More specifically, compared to A11 which has an IC50 of 4.0-17.6 μg/mL, the antibody B11 improves neutralization of DV-4, achieving an IC50 of 0.50-1.4 μg/mL. These results indicate that B11 achieves an about 8 to about 12-fold lower IC50 than A11. Based on B11's superior neutralization activity, humanized variants of B11 were created.

Example 3. Humanized Anti-Dengue Antibodies

FIG. 4 describes some humanized antibodies related to A11 and B11. Various humanization frameworks were tested. The rightmost four columns show the affinity of each antibody for EDIII of dengue virus serotypes DV-1, DV-2, DV-4, and DV-4. An A98V mutation in the heavy chain FW3 (compare antibody B48+A98V to antibody B48) improved binding to DV-4 by about 5-fold, while retaining or improving binding to the other serotypes.

Example 4. Back-Mutations of Humanized Anti-Dengue Antibodies

To improve antibody affinity for EDIII, especially in DV-4, various back-mutations were made to the heavy chain N-terminus of selected humanized antibodies. FIG. 5 shows that D48, which is a full mouse reversion of the N-terminus, has an about two-fold improvement in affinity relative to an antibody with a fully humanized N-terminus. In other cases, back-mutation resulted in a similar, slightly lower, or slightly higher affinity for EDIII-DV-4.

The rightmost column in the upper and lower table of FIG. 5 shows that humanized antibodies' affinity for DV-4 are between 7.494 and 26.89 nM. This retention of binding activity indicates that there is a fair amount of tolerance for mutation in the N-terminal region, e.g., in positions 1-6 of the heavy chain.

Example 5. Improvement in Antibody Affinity Through a Combination of Affinity-Enhancing Mutations To further improve the affinity of the humanized antibodies for DV-4, various affinity-enhancing mutations were tested alone or in combination. In FIG. 6, the following mutations were tested: T33V, del26, G27A, G27Y, F28W, F28G, F28A, and F28Y, all in the VH. Del26 and T33V together (in antibody D88) was found to improve affinity for EDIII-DV-4 by about 4-fold compared to the T33V mutation alone (in antibody C88). The double del26 and T33V mutation found in antibody D88 also improves affinity over an antibody having the del26 mutation alone. This additive or synergistic improvement in binding was unexpected.

From FIG. 6, it is also apparent that several mutations can be combined without reducing affinity or with only a modest reduction in affinity (e.g., F28W and T33V in antibody D118, G27A and T33V in antibody D98, G27Y and T33V in antibody D148, G27Y and F28W and T33V in antibody D108, and G27A and F28W and T33V in antibody D128). This experiment indicates that the antibody has some tolerance for substitutions at positions 27 and 28.

Next, mutations at position 98 in the VH were tested in combination with other mutations. The original humanized sequence has A at position 98. FIG. 7 shows that 98V improves binding to DV-4 about two-fold relative to 98S or 98A, in the context of a T33V mutation (see top three rows of the table). The bottom three rows of the table show that mutations to position 98 do not have a strong effect in the context of the double mutation del26+T33V. Accordingly, the antibody molecule has some tolerance to mutations to residue 98.

Example 6. Additional Binding Studies on Humanized Anti-Dengue Antibodies

Several humanized anti-dengue antibodies were tested for their ability to bind EDIII from dengue virus serotypes DV-1, DV-2, DV-3, and DV-4. FIG. 8 shows the antibodies' affinity as determined by a competition ELISA assay, and FIG. 9 shows antibodies' affinity as determined by SPR. While all the humanized antibodies have strong affinity (e.g., all are less than or equal to 24.35 nM and many are in the sub-nanomolar range), some antibodies have particularly strong binding. For example, C88 and D88 bind to DV-1 with about 20-fold greater affinity than C98 does. A11 three antibodies of FIG. 9 have about equal affinity for DV-2 and for DV-3. Of the antibodies in FIG. 9, D88 has the strongest affinity for DV-4.

Genetic and antigen diversity of dengue virus exists not only between serotypes but also within serotypes. To investigate more completely the breadth of binding by anti-dengue virus antibodies, a set of analyses were performed to identify a panel of strain sequences that further captures dengue virus sequence diversity, specifically in EDIII. First, >3,500 E protein sequences of dengue virus isolates from NCBI GenBank were analyzed for amino acid diversity in EDIII. From this analysis, a set of 21 strain EDIII sequences were identified and selected to more completely represent dengue virus diversity. More specifically, those sequences represent all genotypes having evidence of recent circulation and recent isolates from major endemic regions (clinically relevant strains). Challenging isolates, e.g., those having positions of diversity near or in the epitope region, were selected whenever possible. Additionally, prototypic strains were included. The phylogenetic relationship of the EDIII amino acid sequences of the selected panel of 21 dengue virus isolates is summarized in FIG. 10A. The results of antibody D88 binding to a panel of EDIII proteins of twenty-one diverse dengue strains are shown in FIG. 10B. As shown in FIG. 10B, antibody D88 exhibits full spectrum binding to dengue viruses.

Example 7. Humanized Anti-Dengue Antibodies Bind to EDIII from a Number of Strains of Serotypes DV-2, DV-3, and DV-4

D88 (FIG. 11, rightmost column) and C88 (second column from the right) were tested for the ability to bind EDIII isolated from various strains of dengue virus. The serotype and geographical location of the strain are indicated in the leftmost two columns. In general, the antibodies displayed a good breadth of binding, indicating that they are likely effective against a wide range of dengue virus strains.

Example 8. Humanized Anti-Dengue Antibodies Neutralize Dengue Virus in a Focus Reduction Neutralization Test Humanized antibodies have the capacity to neutralize DV-1, DV-2, DV-3 and DV-4 in a focus reduction neutralization test. The assay is described above in Example 2. FIGS. 12, 13, and 14 show the results of these experiments with representative DV-3 and DV-4 strains. Humanized antibodies are effective in neutralizing dengue virus in this assay. For instance, A48, C98, and D88 achieve a lower EC50 for DV-4 than the mouse anti-dengue antibody A11 (FIG. 12). FIG. 13 shows that antibodies D88, D188, and D128 have an EC50 in the range of 426-506 ng/ml for this strain of DV-3. In addition, D88, D188, and D128 had a lower EC50 for DV-4 than the mouse anti-dengue antibody A11 (FIG. 14). Humanized antibodies also have the capacity to neutralize DV-1 and DV-2 (data not shown). It was unexpected that humanized antibodies would achieve a higher activity than a mouse anti-dengue antibody. Based at least in part, on binding data shown herein and sequence analysis of known dengue isolates, humanized anti-dengue antibody molecules as described herein are likely to have broad neutralization capacity across all serotypes and genotypes with those strains listed herein representatives of the diversity of Dengue virus.

Example 9. Thermal Stability of Humanized Antibodies was Tested by Thermal Shift Analysis Selected humanized antibodies were assayed for stability by thermal shift analysis using the reagent Sypro Orange. Results of the experiments are shown in FIGS. 15A, 15B, and 15C. In general, the humanized antibodies showed good stability, often having a Tm between about 64 and 68.

Example 10. Mouse Models for Dengue Virus

The antibody molecules described herein can be tested for efficacy in an animal model. One such model, the AG129 mouse model, is described in Tharakaraman et al., 2013, *Proc Natl Acad Sci USA*. 2013; 110(17):E1555-64. The AG129 mouse strain, which lacks both type-I and type-II interferon receptors, is a commonly used animal model that replicates some of the disease manifestations observed in clinical cases of dengue, including viremia and other signs of disease. Infected AG129 mice may experience neurological impairment associated with DENV replication in the brain, which is only very rarely observed in human patients infected with the virus. This often leads to death of infected AG129 mice around 18 days after virus challenge (Stein, D. A., et al., *J Antimicrob Chemother,* 2008. 62(3): p. 555-65.; Johnson A J, Roehrig J T. *J Virol.* 1999 January; 73(1):783-6. Despite the lack of similarities to human infection, this model is useful in evaluation of antiviral treatments and can be used in proof of principle studies. Briefly, the AG129 (which is deficient in IFN-$\alpha/\beta$ and IFN-$\gamma$ receptors) mouse is challenged with dengue virus, and a candidate therapeutic antibody molecule is administered. Typically, viremia (virus titer in a blood sample) is the endpoint of the experiment. Viremia can be measured, e.g., with quantitative RT-PCR. In this study, viremia, weight change, and survival were used as disease signs after infection with the New Guinea C (NGC) strain of DENV-2. The results shown in this Example demonstrate a strong in vivo inhibitory activity of antibody D88 in a DENV-2 mouse model.

Animals were block-randomized according by cage to groups, with 10 included in each. Animals were treated with antibody D88, an irrelevant isotype-matched control mAb (CmAb), or placebo one day prior to virus challenge. A group of mice, which were not challenged with virus, were treated with D88 and served as toxicity controls. A group of mice was also included as normal controls, and were not treated or challenged with virus to monitor handling and caging techniques for effects on the immunocompromised AG129 mice. A $10^{-1}$ dilution ($10^{6.8}$ CCID$_{50}$ (cell culture infectious dose 50%)/ml) of the virus was prepared in minimal essential media. Mice were injected intraperitoneally (i.p.) with 0.4 ml of the diluted virus ($10^{6.4}$ CCID$_{50}$/animal). Mortality was observed daily for 31 days. Mice were weighed on day 0 and every other day beginning at 1 dpi (day post infection). Serum was collected from all animals on 3 dpi for quantification of viremia by qRT-PCR.

Figure 16:
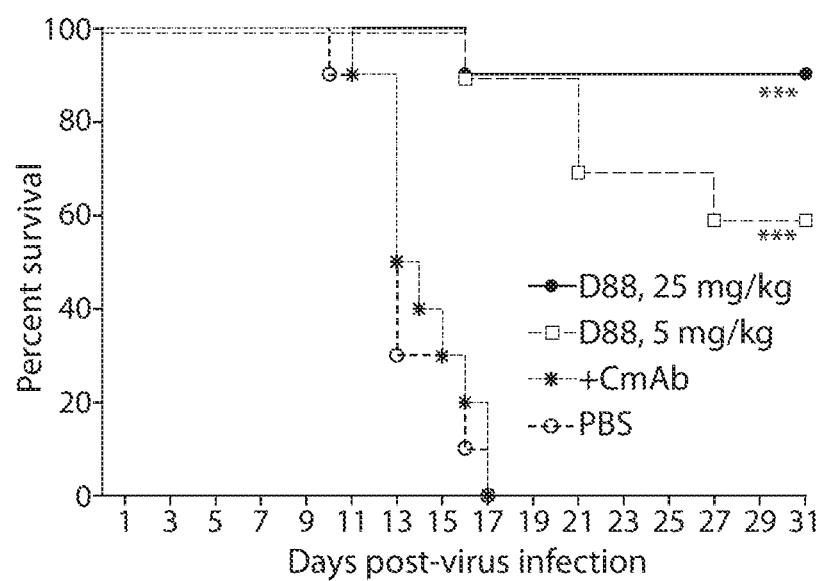
FIG. 16 shows the effect of antibody D88 on survival of mice infected with dengue virus in an AG129 mouse model.

FIG. 16 shows the survival percentage of mice administered D88 (25 mg/kg), D88 (5 mg/kg), CmAb, or PBS, after infection with dengue virus. As shown in FIG. 16, about 90% of the mice treated with 25 mg/kg of D88 and about 60% of the mice treated with 5 mg/kg of D88 survived until Day 31, whereas control mice treated with CmAb or PBS all died on or before Day 17.

Figure 17:
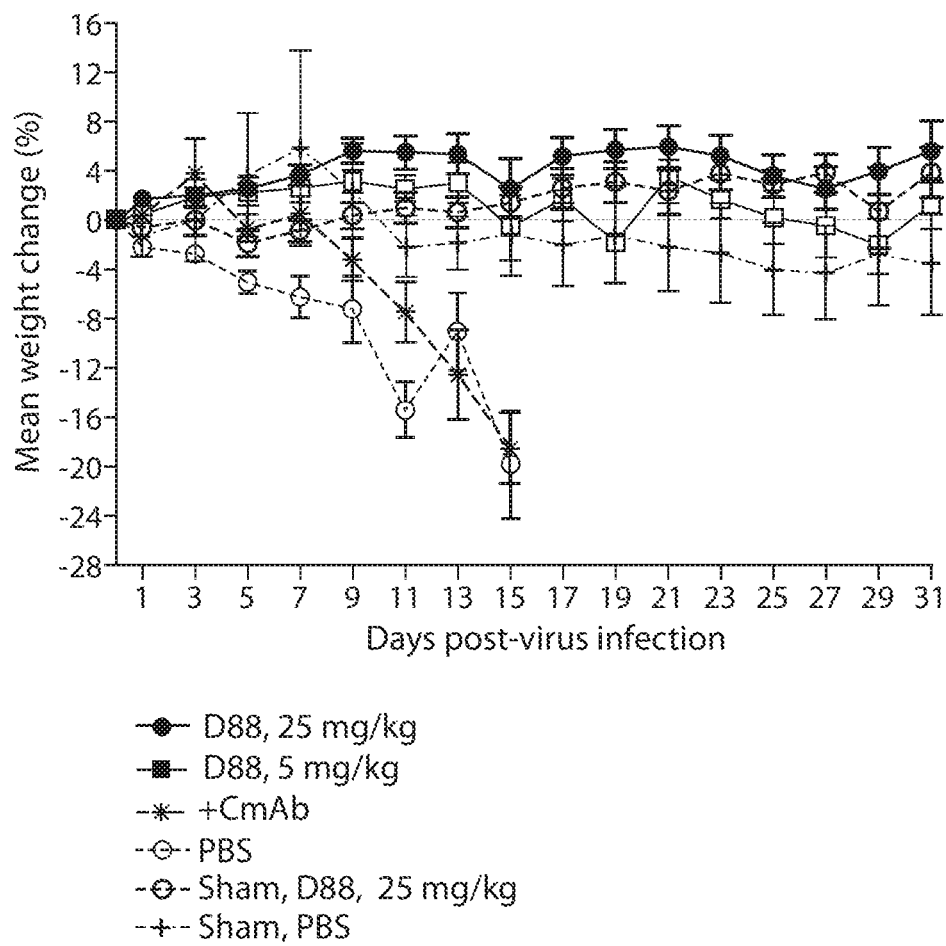
FIG. 17 shows the effect of antibody D88 on weight change of mice infected with dengue virus in an AG129 mouse model.

FIG. 17 shows the mean weight change of mice administered D88 (25 mg/kg), D88 (5 mg/kg), CmAb, or PBS, after infection with dengue virus. Mice treated with D88 (25 mg/kg) or PBS but not infected with dengue virus (sham) were also tested. As shown in FIG. 17, mice administered antibody D88 had no significant weigh change even 31 days post infection, whereas mice administered CmAb or PBS had significant weight loss at Day 15. As a control, mice treated with D88 or PBS but not infected with dengue virus did not exhibit apparent weight change.

Figure 18:
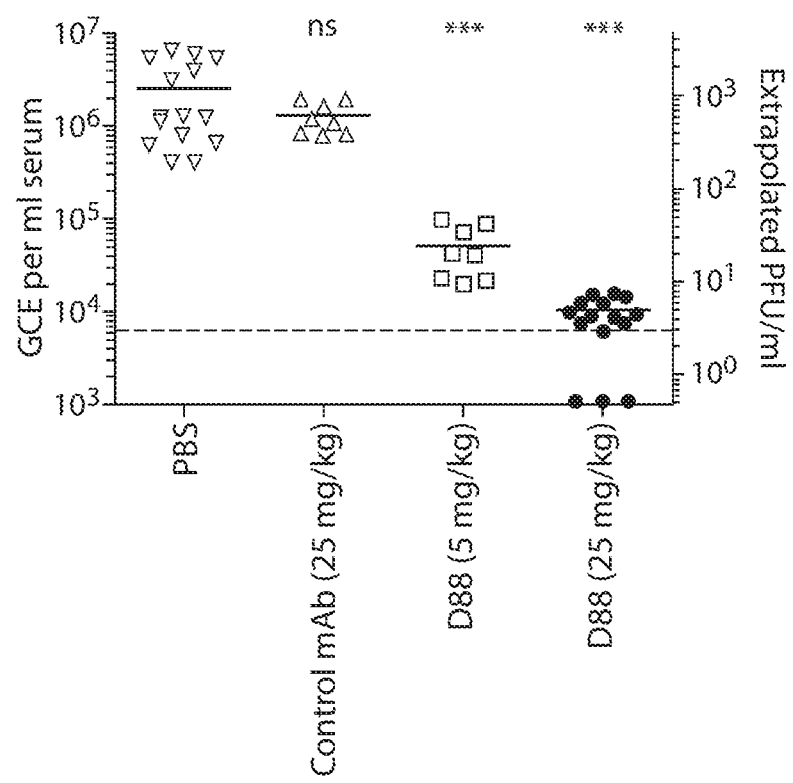
FIG. 18 shows the effect of antibody D88 on viremia in mice infected with dengue virus serotype 2 (strain NGC) in an AG129 mouse model.

FIG. 18 shows the viremia titer in mice administered D88 (25 mg/kg), D88 (5 mg/kg), CmAb, or PBS, after infection with dengue virus. The results are expressed as extrapolated PFU per ml and genome copy equivalents (GCE)/mL. Significance with a p value <0.001 is shown by the symbols ***. As shown in FIG. 18, mice administered CmAb (isotype control) or PBS had higher viremia titer compared to mice treated with 25 mg/kg of D88 or 5 mg/kg of D88.

These results demonstrate that a single systemic administration of antibody D88 resulted in rapid reduction of circulating viral titers. Antibody D88 provided strong protection, with 9/10 and 6/10 animals at 25 and 5 mg/kg, respectively, surviving DENV-2 lethal challenge. Antibody D88 demonstrated a significant and dose-dependent reduction in viral titer on day 3 post-infection, the day of peak viremia.

Example 11. Protection Against ADE In Vivo

The antibody molecules described herein can be tested for efficacy in animal models. One such model, antibody-enhanced severe dengue virus infection in AG129 mice, is described in Balsitis et al., 2010 (Lethal antibody enhancement of dengue disease in mice is prevented by Fc modification, PLoS Pathogens, 2010 Feb. 12; 6(2):e1000790). Briefly, AG129 mice are administered dengue virus enhancing antibody (e.g., DV1 antiserum or 4G2 monoclonal antibody) 1 day prior to challenge with dengue virus (e.g., D2S10). Candidate antibody molecule is administered 1 day prior to challenge (prophylaxis) or 1 or 2 days after challenge (therapeutic). Typically, mortality is the endpoint of the experiment; viremia and inflammatory cytokine (e.g., TNF-α) levels in the serum may also serve as endpoints.

Example 12. Neutralization of Dengue Virus Serotypes Propagated in Insect and Mammalian Cells The neutralization activity of humanized antibodies against four dengue virus serotypes was examined by a Focus Reduction Neutralization test (FRNT) as described above in Example 2. Four dengue virus serotypes (DENV-1, DENV-2, DENV-3 and DENV-4) were propagated in either insect cells or mammalian cells and were used to infect host Vero (monkey) cells. FIGS. 16-18 show the results of these experiments with representative DENV-1-4 strains. Data are expressed as the relative infectivity. For example, the EC50 or FRNT50 values represent the concentrations of antibody required to achieve 50% virus neutralization. As shown in FIGS. 16-18, the tested antibodies are effective in neutralizing DENV-1, DENV-2, DENV-3 and DENV-4 strains propagated in insect and mammalian cells.

Figure 19:
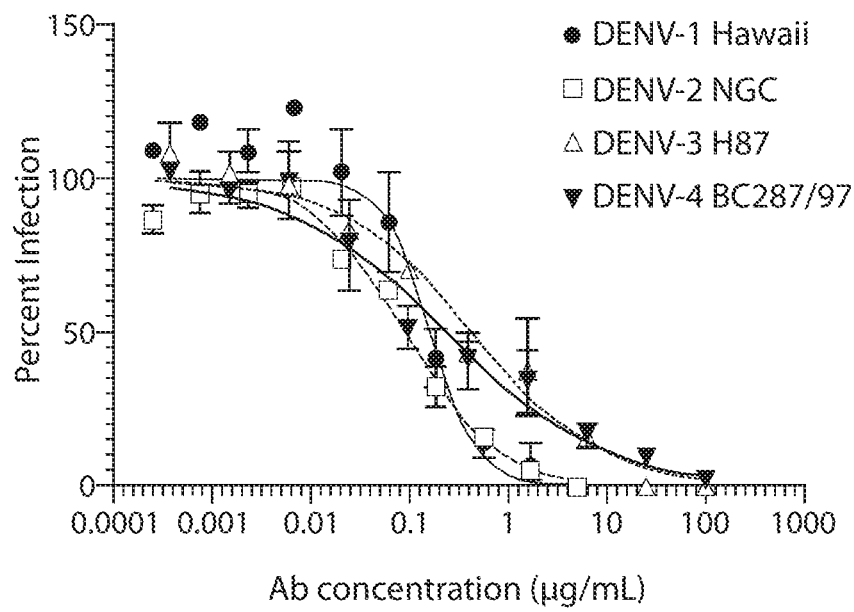
FIG. 19 shows the ability of antibody D88 to neutralize dengue virus serotypes DENV-1, DENV-2, DENV-3, and DENV-4 propagated in C6/36 insect cells in a focus reduction neutralization test (FRNT).

FIG. 19 shows that antibody D88 neutralized DENV-1, DENV-2, DENV-3 and DENV-4 strains propagated in C6/36 insect cells. The results are summarized in the table at the bottom of FIG. 19, which shows the EC50 values against representative DENV-1, DENV-2, DENV-3 and DENV-4 strains (in ng/ml). DENV-1 strain Hawaii/1944, DENV-2 strain New Guinea/1944 (NGC), DENV-3 strain Philippines/1956 (H87), and DENV-4 strain Mexico/1997 (BC287/97) were tested.

FIG. 20 shows that antibody D88 neutralized DENV-1, DENV-2, DENV-3 and DENV-4 strains propagated in Vero cells. The results are shown as the FRNT50 values against representative DENV-1, DENV-2, DENV-3 and DENV-4 strains (in ng/ml). DENV-1 strain Hawaii/1944, DENV-2 strain New Guinea/1944 (NGC), DENV-3 strain Philippines/1956 (H87), and DENV-4 strain Mexico/1997 (BC287/97) were tested.

Figure 21:
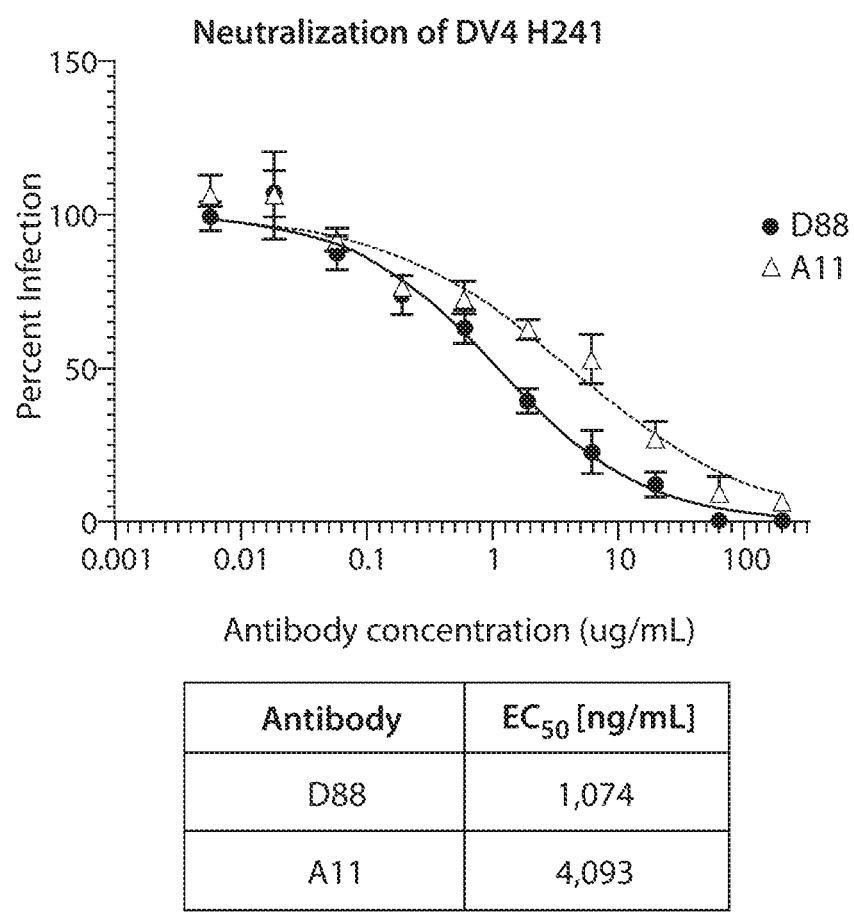
FIG. 21 shows the ability of antibody D88 and A11 to neutralize dengue virus DENV-4 strain H241 propagated in Vero (monkey) cells in a focus reduction neutralization test (FRNT).

FIG. 21 shows that antibodies D88 and A11 neutralized DENV-4 strain H241 propagated in Vero cells. The results are summarized in the table at the bottom of FIG. 21, which shows the EC50 values of the antibodies against DENV-4 strain H241 (in ng/ml).

These results demonstrate that antibody D88 potently neutralized all four DENV serotypes with EC50 values of <1 µg/ml. Antibody D88 efficiently neutralized the challenging DENV-4 strain H241, to which it bound with 100 nM affinity.

Example 13. Mosquito Models for Dengue Virus to Evaluate Inhibitory Activity of Antibodies The antibody molecules described herein can be tested for efficacy in a mosquito model. Dengue virus is a mosquito transmitted RNA virus. Certain dengue virus can develop in vivo fitness advantage, which may result in higher probability of human-to-mosquito transmission (Vu et al., PLoS Negl Trop Dis. 2010; 4(7):e757). To establish a mosquito model to evaluate inhibitory activity of antibodies against dengue virus, blood containing virus is mixed with antibody at various dilutions and incubate at 37° C. for 30 minutes. Antibody-spiked blood is added to a mosquito feeder and mosquitoes are fed for about 1 hour. Mosquitoes are cold-anaesthetized and engorged ones are selected. Mosquitoes' abdomens are collected at day 7 after blood feeding. Viral load can be measured by qRT-PCR. The proportion of mosquitoes with abdomen infection can be calculated as the number of infected abdomens divided by the total number of abdomens tested by PCR.

Example 14. HP-SEC Evaluation of Anti-Dengue Antibodies

High performance size exclusion chromatography (HP-SEC) was performed to evaluate aggregation propensity of anti-dengue antibodies under native, non-stressed conditions. This method allows for discrimination of antibody dimers and aggregates from monomers. Dimers and aggregates may lead to increased risk of immunogenicity.

In this study, antibodies were purified to 1 mg/ml and evaluated by a size exclusion column, e.g., Phenomenex BioSep s3000, using PBS as a mobile phase with a flow rate of 1 ml/min.

Figure 22:
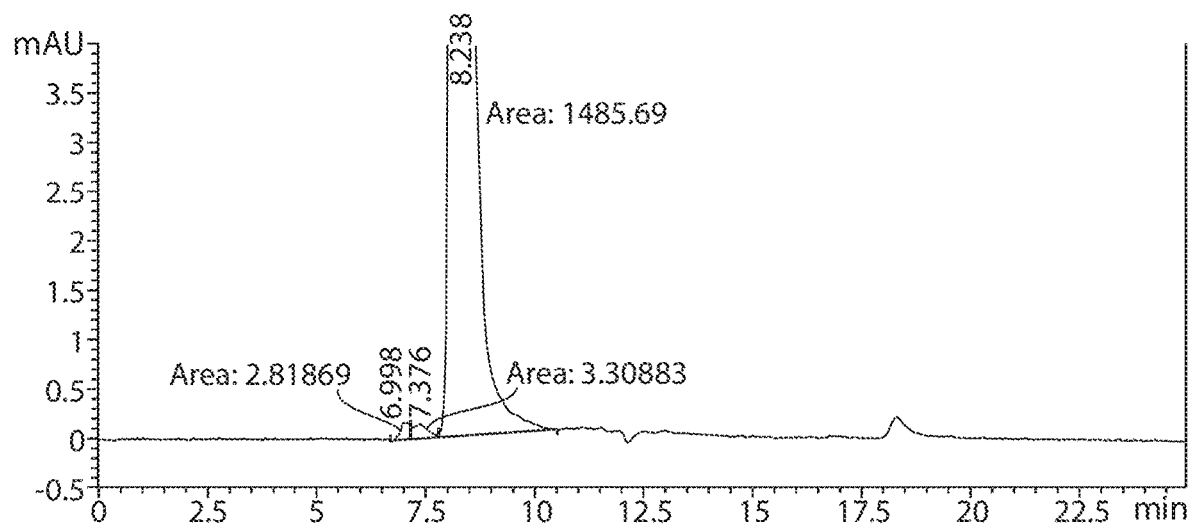
FIG. 22 shows the aggregation propensity of antibodies A48, C88 and D88 as evaluated by high performance size exclusion chromatography (HP-SEC).

FIG. 22 shows a representative chromatogram of antibody D88, which displays greater than 98% of antibody (purified only by Protein A chromatography) present as monomer. As summarized in the table at the bottom of FIG. 22, 99.15% of antibody A48, 98.37% of antibody C88, and 99.59% of antibody D88, were present as monomers in the samples.

INCORPORATION BY REFERENCE

All publications, patents, and accession numbers mentioned herein are hereby incorporated by reference in their entirety as if each individual publication or patent was specifically and individually indicated to be incorporated by reference.

EQUIVALENTS

While specific embodiments of the compositions and methods herein have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating dengue virus, comprising administering to a subject in need thereof an isolated antibody molecule in an amount effective to treat the virus, wherein the antibody molecule comprises:
   (a) a heavy chain immunoglobulin variable region segment comprising:
      a CDR1 comprising the sequence DVYMS (SEQ ID NO: 3),
      a CDR2 comprising the sequence RIDPENGDT-KYDPKLQG (SEQ ID NO: 4), and
      a CDR3 comprising the sequence GWEGFAY (SEQ ID NO: 5); and
   (b) a light chain variable region segment comprising:
      a CDR1 comprising the sequence RASENVDKYG-NSFMH (SEQ ID NO: 6),
      a CDR2 comprising the sequence RASELQW (SEQ ID NO: 7), and
      a CDR3 comprising the sequence QRSNEVPWT (SEQ ID NO: 8).

2. The method of claim 1, wherein the dengue virus is of serotype DV-1, DV-2, DV-3, and DV-4.

3. The method of claim 1, wherein the antibody molecule neutralizes dengue virus serotypes DV-1, DV-2, DV-3, and DV-4.

4. The method of claim 1, wherein the subject is infected with dengue virus.

5. The method of claim 1, wherein the antibody molecule is administered to the subject prior to the subject being exposed to dengue virus.

6. The method of claim 1, wherein the antibody molecule is administered to the subject prior to onset of one or more manifestations of dengue virus.

7. The method of claim 1, wherein the antibody molecule comprises a VH FW1 having the sequence QVQLVQS-GAEVKKPGASVKVSCKAGFNIK (SEQ ID NO: 11) or a FW1 of the VH amino acid sequence of SEQ ID NO: 36.

8. The method of claim 1, wherein the antibody molecule comprises a VH FW2 having the sequence WVRQAPGQ-GLEWMG (SEQ ID NO: 84) or WVRQAPEQGLEWMG (SEQ ID NO: 85).

9. The method of claim 1, wherein the antibody molecule comprises the VH amino acid sequence of SEQ ID NO: 1.

10. The method of claim 1, wherein the antibody molecule comprises the VL amino acid sequence of SEQ ID NO: 2.

11. The method of claim 1, wherein the antibody molecule comprises the VH amino acid sequence of SEQ ID NO: 1 and the VL amino acid sequence of SEQ ID NO: 2.

12. The method of claim 1, wherein the antibody molecule is a Fab, F(ab')2, Fv, or a single chain Fv fragment (scFv).

13. The method of claim 1, wherein the antibody molecule comprises a heavy chain constant region chosen from IgG1, IgG2, IgG3, or IgG4.

14. The method of claim 1, wherein the antibody molecule comprises a light chain constant region chosen from the light chain constant regions of kappa or lambda.

15. The method of claim 1, wherein the antibody molecule comprises one or more framework regions derived from a human framework germline sequence.

16. The method of claim 1, wherein the antibody molecule is capable of binding to dengue virus EDIII (E protein domain III).

17. The method of claim 16, wherein the antibody molecule is capable of binding to dengue virus EDIII with a dissociation constant ($K_D$) of less than about 30 nM.

18. The method of claim 16, wherein the antibody molecule is capable of binding to dengue virus serotype DV-4 EDIII with a dissociation constant ($K_D$) of less than about 10 nM.

19. The method of claim 16, wherein the antibody molecule is capable of binding to DV-3 or DV-4 EDIII domain with at least a 6-fold greater affinity than an antibody comprising the VH amino acid sequence of SEQ ID NO: 33 and the VL amino acid sequence of SEQ ID NO: 34 or antibody 4E11.

20. The method of claim 1, wherein the antibody molecule is capable of binding to an EDIII polypeptide from a dengue virus strain chosen from DENV-1/Vietnam/2008, DENV-1/Malaysia/2005, DENV-1/Mexico/2007, DENV-2/Singapore/2008, DENV-2/Venezuela/2007, DENV-2/Peru/1995, DENV-2/Vietnam/2007, DENV-3/Cambodia/2008, DENV-3/Singapore/2009, DENV-3/Nicaragua/2010, DENV-3/Puerto Rico/1977, DENV-4/Venezuela/2008, DENV-4/Singapore/2010, DENV-4/New Caledonia/2009, DENV-4/Brazil/2011, DENV-4/Thailand/1997, or DENV-4/Philippines/1956 (H241), with at least 2-fold greater affinity than an antibody comprising the VH amino acid sequence of SEQ ID NO: 33 and the VL amino acid sequence of SEQ ID NO: 34 or antibody 4E11.

21. The method of claim 1, wherein the antibody molecule is capable of neutralizing dengue virus in a focus reduction neutralization test.

22. The method of claim 1, wherein the antibody molecule is capable of neutralizing dengue virus with an IC50 that is at least 2-fold lower than an antibody comprising the VH amino acid sequence of SEQ ID NO: 33 and the VL amino acid sequence of SEQ ID NO: 34 or antibody 4E11 in a focus reduction neutralization test.

23. The method of claim 1, further comprising administering an anti-viral agent to the subject.

24. The method of claim 23, wherein the anti-viral agent is chosen from one or more of balapiravir, chloroquine, celgosivir, ivermectin, or *Carica folia*.

25. The method of claim 23, wherein the anti-viral agent is an anti-dengue antibody different from the antibody molecule comprising:
(a) a heavy chain immunoglobulin variable region segment comprising:
 a CDR1 comprising the sequence DVYMS (SEQ ID NO: 3),
 a CDR2 comprising the sequence RIDPENGDT-KYDPKLQG (SEQ ID NO: 4), and
 a CDR3 comprising the sequence GWEGFAY (SEQ ID NO: 5); and
(b) a light chain immunoglobulin variable region segment comprising:
 a CDR1 comprising the sequence RASENVDKYG-NSFMH (SEQ ID NO: 6),
 a CDR2 comprising the sequence RASELQW (SEQ ID NO: 7), and
 a CDR3 comprising the sequence QRSNEVPWT (SEQ ID NO: 8).

26. The method of claim 23, wherein the anti-viral agent is chosen from one or more of an alpha-glucosidase I inhibitor, an adenosine nucleoside inhibitor, an inhibitor of NS3 and/or its cofactor NS2B, an RNA-dependent RNA polymerase (RdRp) inhibitor, an inhibitor of host pyrimidine biosynthesis, an inhibitor of viral NS4B protein, or an iminosugar.

27. The method of claim 26, wherein the alpha-glucosidase I inhibitor is celgosivir, the adenosine nucleoside inhibitor is NITD008, the inhibitor of NS3 and/or its cofactor NS2B is a [5-amino-1-(phenyl)sulfonyl-pyrazol-3-yl] compound, the RNA-dependent RNA polymerase (RdRp) inhibitor is NITD107, the inhibitor of host pyrimidine biosynthesis is an inhibitor of host dihydroorotate dehydrogenase (DHODH) selected from NITD-982 or brequinar, the inhibitor of viral NS4B protein is NITD-618, or the iminosugar is UV-4.

28. The method of claim 1, further comprising administering a vaccine to the subject.

29. The method of claim 1, wherein administration is parenteral or intravenous.

30. A method of treating a dengue virus infection, comprising administering to a subject in need thereof an effective amount of an isolated antibody molecule comprising the VH amino acid sequence of SEQ ID NO: 1 and the VL amino acid sequence of SEQ ID NO: 2.

* * * * *